(12) United States Patent
Li et al.

(10) Patent No.: US 11,026,889 B2
(45) Date of Patent: Jun. 8, 2021

(54) POLYMERIC DRUG DELIVERY SYSTEMS FOR TREATMENT OF DISEASE

(71) Applicant: Board of Regents, The University of Texas System, Austin, TX (US)

(72) Inventors: Chun Li, Missouri City, TX (US); Jun Zhao, Houston, TX (US); Jason Fleming, Tampa, FL (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/780,799

(22) PCT Filed: Dec. 9, 2016

(86) PCT No.: PCT/US2016/065763
§ 371 (c)(1),
(2) Date: Jun. 1, 2018

(87) PCT Pub. No.: WO2017/100533
PCT Pub. Date: Jun. 15, 2017

(65) Prior Publication Data
US 2020/0246264 A1    Aug. 6, 2020

Related U.S. Application Data

(60) Provisional application No. 62/265,167, filed on Dec. 9, 2015.

(51) Int. Cl.
| | | |
|---|---|---|
| A61P 35/00 | (2006.01) | |
| C08F 8/42 | (2006.01) | |
| A61K 9/107 | (2006.01) | |
| A61K 9/127 | (2006.01) | |
| A61K 31/337 | (2006.01) | |
| A61K 31/395 | (2006.01) | |
| A61K 31/438 | (2006.01) | |
| A61K 31/59 | (2006.01) | |
| C08F 293/00 | (2006.01) | |

(52) U.S. Cl.
CPC ............ *A61K 9/107* (2013.01); *A61K 9/1273* (2013.01); *A61K 31/337* (2013.01); *A61K 31/395* (2013.01); *A61K 31/438* (2013.01); *A61K 31/59* (2013.01); *A61P 35/00* (2018.01); *C08F 293/005* (2013.01)

(58) Field of Classification Search
None
See application file for complete search history.

(56) References Cited

U.S. PATENT DOCUMENTS

2014/0298591 A1* 10/2014 Hazenkamp ......... C11D 3/3788
8/137

OTHER PUBLICATIONS

Yuan et al., Macromolecules, 2007, 40(25), pp. 9094-9102 (Year: 2007).*

(Continued)

*Primary Examiner* — Brian Gulledge
(74) *Attorney, Agent, or Firm* — Parker Highlander PLLC

(57) ABSTRACT

Provided are compositions and nanoparticle formulations that may be used, e.g., to deliver a therapeutic compound to a subject. In some embodiments, the nanoparticles may be used to deliver one or more chemotherapeutic agents to treat a cancer such, e.g., as a pancreatic ductal adenocarcinoma.

22 Claims, 32 Drawing Sheets

(56) References Cited

OTHER PUBLICATIONS

Du et al., Biomacromol., 2009, 10(8), pp. 2169-2174 (Year: 2009).*
Zhang et al., Biomacromol., 2010, 11(5), pp. 1331-1338 (Year: 2010).*
Chen et al., Chem. Commun., 2014, vol. 50, p. 14482-14493 (Year: 2014).*
Office Action issued in Chinese Application No. 201680081255.2, dated Apr. 23, 2020, and English language translation thereof.
Zhao et al., "Cyclopamine-loaded core-cross-linked polymeric micelles enhance radiation response in pancreatic cancer and pancreatic stellate cells," *Mol Pharmaceutics*, 12(6):2093-2100, 2015.
Bee et al., The development of a high-content screening binding assay for the smoothened receptor. J Biomol Screen, 17 (7), 900-11, 2012.
Chen et al., "The Influence of Polymer Topology on Pharmacokinetics: Differences Between Cyclic and Linear PEGylated Poly(acrylic Acid) Comb Polymers", *J. Control. Rel.*, 140(3):203-209, 2009.
Chen et al., Small molecule modulation of Smoothened activity. Proceedings of the National Academy of Sciences of the United States of America, 99 (22), 14071-6, 2002.
Chitkara et al., Micellar Delivery of Cyclopamine and Gefitinib for Treating Pancreatic Cancer. Molecular Pharmaceutics, 9 (8), 2350-2357, 2012.
Cho et al., "Poly(ethylene glycol)-block-poly(ε-caprolactone) Micelles for Combination Drug Delivery: Evaluation of Paclitaxel, Cyclopamine and Gossypol in Intraperitoneal Xenograft Models of Ovarian Cancer", *J. Control. Rel.*, 16(1):1-9, 2013.
Du et al., "Evaluation of Polymeric Micelles from Brush Polymer with Poly(E-caprolactone)-b-Poly(ethylene glycol) Side Chains as Drug Carriers", *Biomacromolecules*, 10:2169-2174, 2009.
Estrella et al., Acidity generated by the tumor microenvironment drives local invasion. Cancer Res, 73 (5), 1524-35, 2013.
Feig et al., The pancreas cancer microenvironment. Clin Cancer Res, 18 (16), 4266-76, 2012.
Feldmann et al., Blockade of hedgehog signaling inhibits pancreatic cancer invasion and metastases: a new paradigm for combination therapy in solid cancers. Cancer Res, 67 (5), 2187-96, 2007.
Geng et al., Hedgehog signaling in the murine melanoma microenvironment. Angiogenesis 2007, 10 (4), 259-67, 2007.
International Preliminary Report on Patentability issued in corresponding PCT Application No. PCT/US2016/065763, dated Jun. 12, 2018.
International Search Report and Written Opinion issued in corresponding PCT Application No. PCT/US2016/065763, dated Apr. 13, 2017.
Kelleher, Hedgehog signaling and therapeutics in pancreatic cancer. Carcinogenesis 32 (4), 445-51, 2011.
Kim et al., Pilot clinical trial of hedgehog pathway inhibitor GDC-0449 (vismodegib) in combination with gemcitabine in patients with metastatic pancreatic adenocarcinoma. Clinical Cancer Research, 20 (23), 5937-45, 2014.
Onishi and Katano, Hedgehog signaling pathway as a new therapeutic target in pancreatic cancer. World J Gastroenterol, 20 (9), 2335-42, 2014.
Rucki and Zheng, Pancreatic cancer stroma: understanding biology leads to new therapeutic strategies. World J Gastroenterol, 20 (9), 2237-46, 2014.
Shafaee et al., "Cyclopamine increases the cytotoxic effects of paclitaxel and radiation but not cisplatin and gemcitabine in Hedgehog expressing pancreatic cancer cells", *Cancer Chemother. Pharmacol.*, 58(6):765-770, 2006.
Sorkin and von Zastrow, kinds Nat Rev Mol Signal transduction and endocytosis: close encounters of many Cell Biol, 3 (8), 600-614, 2002.
Steg et al., Gli3 mediates cell survival and sensitivity to cyclopamine in pancreatic cancer. Cancer Biol Ther, 10 (9), 893-902, 2010.
Tempero et al., Pancreatic cancer treatment and research: an international expert panel discussion. Ann Oncol, 22 (7), 1500-6, 2011.
Thayer et al., Hedgehog is an early and late mediator of pancreatic cancer tumorigenesis. Nature, 425 (6960), 851-856, 2003.
Watkins and Peacock, Hedgehog signaling in foregut malignancy. Biochem Pharmacol, 68 (6), 1055-60, 2004.
Yoshida et al., "pH- and ion-sensitive polymers for drug delivery", *Expert Opin. Drug Deliv.*, 10(11):1497-1513, 2013.
You et al., Chemoradiation therapy using cyclopamine-loaded liquid-lipid nanoparticles and lutetium-177-labeled core-crosslinked polymeric micelles. J Control Release, 202, 40-8, 2015.
Zhou et al., "Selective inhibitory effect of HPMA copolymer-cyclopamine conjugate on prostate cancer stem cells", *Biomaterial*, 33(6):1863-1872, 2012.
Office Action issued in Chinese Application No. 201680081255.2, dated Dec. 9, 2020.
Ramasamy et al., "pH sensitive polyelectrolyte complex micelles for highly effective combination chemotherapy," *Journal of Materials Chemistry B*, 2(37):6324-6333, 2014.

\* cited by examiner

Untreated CTL

Treated (6 doses of M-CPA/PTX in 2 weeks)

POLYMERIC DRUG DELIVERY SYSTEMS FOR TREATMENT OF DISEASE

This application is a national phase application under 35 U.S.C. § 371 of International Application No. PCT/US2016/065763, filed Dec. 9, 2016, which claims the benefit of U.S. Provisional Patent Application No. 62/265,167, filed Dec. 9, 2015, the entirety of each of which is incorporated herein by reference.

BACKGROUND OF THE INVENTION

1. Field of the Invention

The present invention relates generally to the field of drug delivery and nanoparticles. More particularly, it concerns polymers and polymeric micelles thereof for the delivery of chemotherapeutic compounds.

2. Description of Related Art

Pancreatic cancer remains one of the most lethal types of cancer despite vigorous research on this disease during the past several decades. The overall 5-year survival rate of patients with pancreatic cancer is below 5%; therefore, there is a dire need to develop an effective therapy for this disease (Tempero et al., 2011). Pancreatic tumors are characterized by excessive desmoplastic stroma (Feig et al., 2012), a fibrotic deposition produced by pancreatic stellate cells, also called fibroblasts. The desmoplastic stroma protects tumor cells against radiation, restricts the delivery of chemotherapy drugs into tumors, and promotes tumor progression and metastasis (Rucki and Zheng, 2014). Thus, stroma depletion has been investigated as a potential treatment for pancreatic cancer. However, stroma depletion alone has not been successful thus far.

The sonic hedgehog (SHH) signaling pathway plays a critical role in the initiation and progression of pancreatic cancer, and sustained activation of this pathway contributes to excessive deposition of tumor stroma and maintenance of tumor-initiating cells (Thayer et al., 2003; Geng et al., 2007; Watkins and Peacock, 2004; Onishi and Katano, 2014). Many preclinical studies have shown that inhibitors of SHH pathway, such as cyclopamine (CPA), saridegib, and vismodegib, are effective against pancreatic cancer (Chen et al., 2002; Kim et al., 2014). CPA is a natural plant product with potent antagonist activity against the smoothened (SMO) receptor in the SHH pathway. CPA can deplete cancer stem cells (CSCs), disrupt tumor stroma, and enhance the tumor response to ionizing radiation (Shafaee et al., 2006; Kelleher, 2011). CPA also increases the cytotoxic effects of paclitaxel (PTX) in SHH-expressing pancreatic cancer cells (Shafaee et al., 2006). However, in many cases, CPA monotherapy only delayed pancreatic tumor growth (Chitkara et al., 2012; You et al., 2015). Moreover, both CPA and PTX are water insoluble and are highly toxic which presents potential co-administration problems. Several polymer-based nanoformulations have been prepared by covalent conjugation or physical encapsulation of CPA (Chitkara et al., 2012; You et al., 2015; Cho et al., 2013; Zhou et al., 2012), and such formulations have shown promising anti-tumor efficacy against different tumor types. However, these formulations displayed undesirable burst release effects or fast release profiles over a 24-h incubation period under physiological conditions. It was also difficult to achieve CPA payload greater than 5% by weight. These shortcomings could limit further development of these CPA nanoparticle formulations. Therefore, there remains a need for improved methods of delivery CPA and other chemotherapeutics for administration to cancers such as pancreatic cancer.

SUMMARY OF THE INVENTION

In some aspects, the present disclosure provides polymers and polymeric micelles thereof for use in the delivery of therapeutic agents. In some embodiments, these drug delivery systems may be used in the treatment of cancers such as pancreatic cancer.

An aspect of the present invention relates to a polymer, wherein the polymer is a block copolymer comprising a polyacrylic acid backbone with a plurality of PEG sidechains and a plurality of ε-caprolactone sidechains. The PEG sidechain component may comprises from 5 to 50, from 3 to 40, from 3 to 20, or 3, 4, 5, 6, 7, 8, 9, 10, 11, 12, 13, 14, 15, 16, 17, 18, 19, 20, 25, 30, 35, or 40, or any range derivable therein of ethylene glycol monomers. In some embodiments, the PEG sidechain is capped with a methyl group. In some embodiments, the ε-caprolactone sidechain comprises from 2 to 20, from 2 to 15, or 2, 3, 4, 5, 6, 7, 8, 9, 10, 11, 12, 13, 14, 15, 16, 17, 18, 19, 20, or any range derivable therein of ε-caprolactone repeating units. In some embodiments, the ε-caprolactone sidechain is esterified with a succinate group. The ε-caprolactone sidechain may be linked to the polyacrylic acid backbone by an ethylene glycol linker. In some embodiments, the polyacrylic acid backbone is capped with an benzyl N-(2-hydroxylethyl)carbamate or ethanolamine group. In some embodiments, the polyacrylic acid backbone is terminated with a halogen group. In some embodiments, the polymer is further defined by the formula:

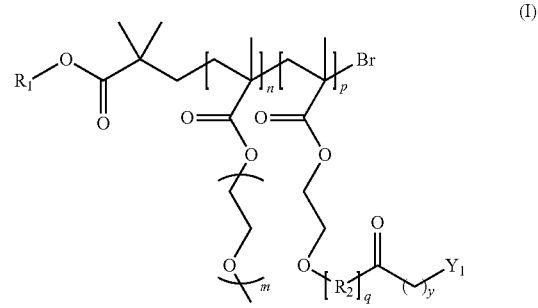

wherein: $R_1$ is alkyl$_{(C1-18)}$, cycloalkyl$_{(C1-18)}$, aryl$_{(C1-18)}$, or a substituted version of any of these groups; or an alkyl$_{(C1-18)}$ substituted with a protected amine group; $R_2$ is a group of the formula:

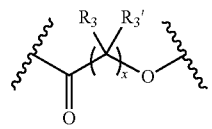

wherein: $R_3$ and $R_3'$ are each independently hydrogen, alkyl$_{(C1-6)}$, or substituted alkyl$_{(C1-6)}$; and x is 1-10; m is 5-40 or 10-40; n is 10-40; p is 5-40 or 5-20; q is 1-20 or 1-10; y is 1-10; and $Y_1$ is carboxy, phosphonate, or hydroxysulfonyl; or a pharmaceutically acceptable salt thereof.

In some embodiments, the polymer further comprises a second polymer of the formula:

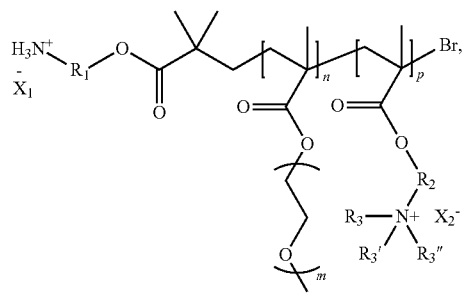

(II)

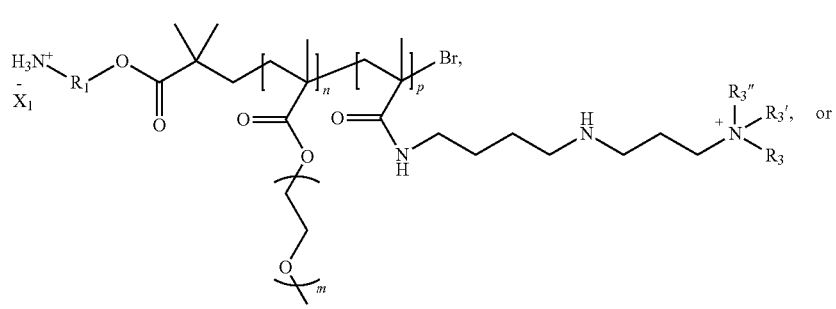

(III)

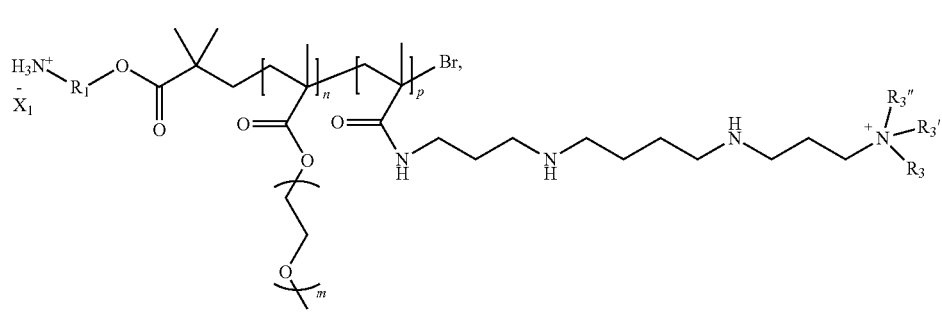

(IV)

wherein: m is 5-40 or 10-40; n is 10-40; p is 5-30; $R_1$ and $R_2$ are each independently alkanediyl$_{(C1-8)}$, arenediyl$_{(C6-12)}$, or a substituted version of either of these groups; $R_3$, $R_3'$, and $R_3''$ are each independently alkyl$_{(C1-8)}$, aryl$_{(C3-12)}$, or a substituted version of any of these groups; and $X_1$ and $X_2$ are each independently a monovalent anion; or a pharmaceutically salt thereof. In some embodiments, m is 5-25, 15-25, 8-10, or any range derivable therein. In some embodiments, n is 15-25, 18-20, or any range derivable therein. In some embodiments, p is 5-25, 18-22, 5-15, or any range derivable therein. In some embodiments, q is 5-10. In some embodiments, x is 5-10, 5, 6, 7, 8, 9, or 10. In some embodiments, $R_3$ and $R_3'$ are hydrogen. In some embodiments, $R_3$ and $R_3'$ are hydrogen and x is 5. $R_1$ may be ethylene. $R_2$ may be ethylene. In some embodiments, $R_3$, $R_3'$, and $R_3''$ are each methyl. $X_1$ may be a halide (e.g., chloride). $X_2$ may be a halide (e.g., chloride).

In some embodiments, the polymer has the structure:

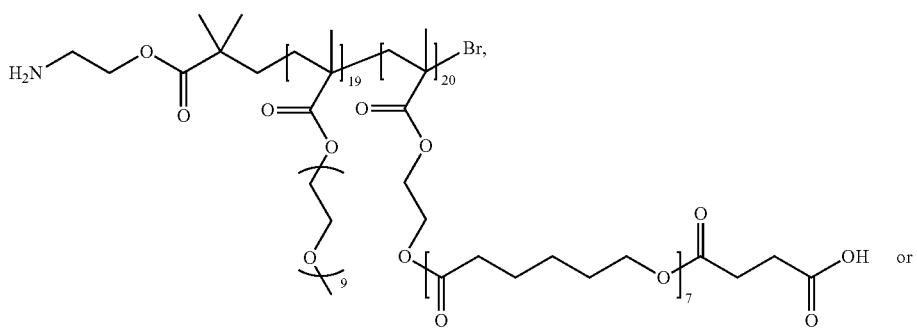

or

-continued

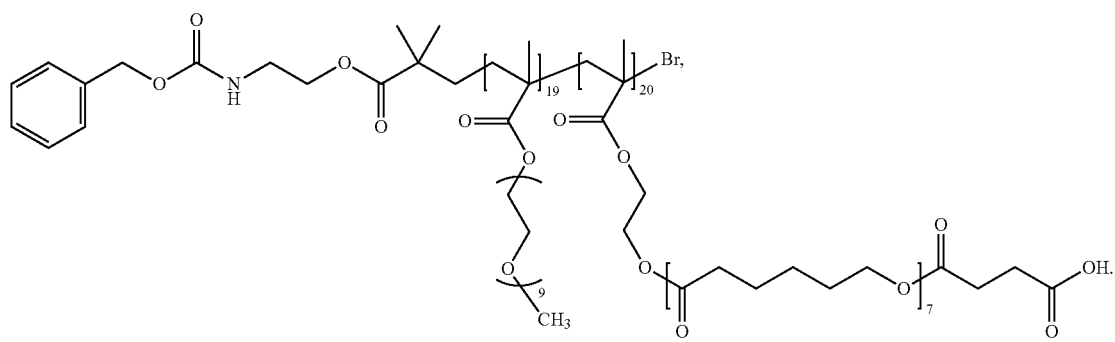

In some embodiments, the second polymer has the structure:

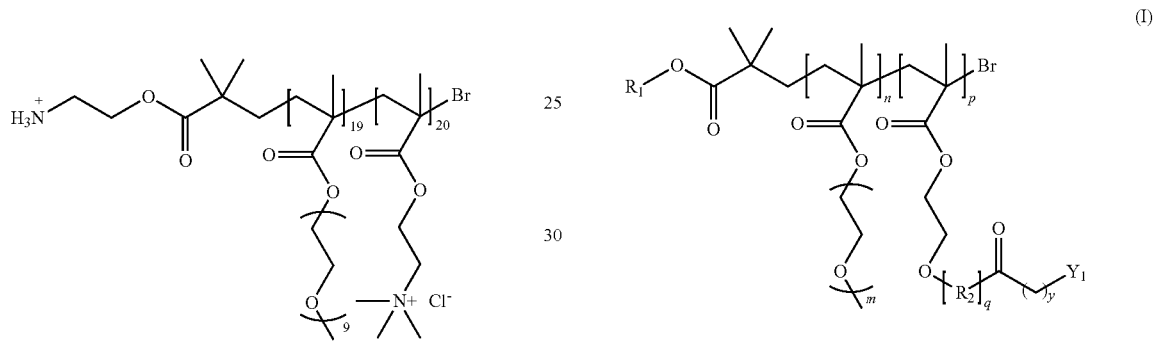

Another aspect of the present invention relates to a pharmaceutical composition comprising: (a) a micelle, liposome, or nanoparticle; and (b) a therapeutic agent (e.g., one or two therapeutic agents); wherein the micelle, liposome, or nanoparticle comprises a first polymer of the present invention or as defined above, and the micelle, liposome, or nanoparticle encapsulates the therapeutic agent. In some embodiments, the pharmaceutical composition further comprises an excipient such as, for example, a monosaccharide or a disaccharide (e.g., sucrose). The micelle, liposome, or nanoparticle further comprises a second polymer. In some embodiments, the first polymer comprises a net anionic charge. In some embodiments, the first polymer is further defined by the formula:

(I)

[Structure shown with $R_1$, $n$, $p$, Br, $m$, $R_2$, $q$, $Y_1$, $y$]

wherein: $R_1$ is alkyl$_{(C1-18)}$, cycloalkyl$_{(C1-18)}$, aryl$_{(C1-18)}$, or a substituted version of any of these groups; or an alkyl$_{(C1-18)}$ substituted with a protected amine group; $R_2$ is a group of the formula:

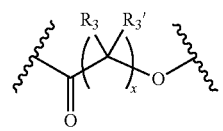

wherein: $R_3$ and $R_3'$ are each independently hydrogen, alkyl$_{(C1-6)}$, or substituted alkyl$_{(C1-6)}$; and x is 1-10; m is 5-40 or 10-40; n is 10-40; p is 5-40 or 5-20; q is 1-20 or 1-10; y is 1-10; and $Y_1$ is carboxy, phosphonate, or hydroxysulfonyl; or a pharmaceutically acceptable salt thereof. In some embodiments, the first polymer is:

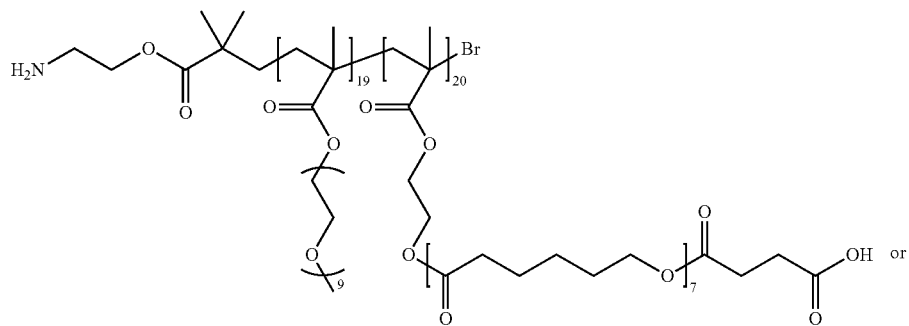

or

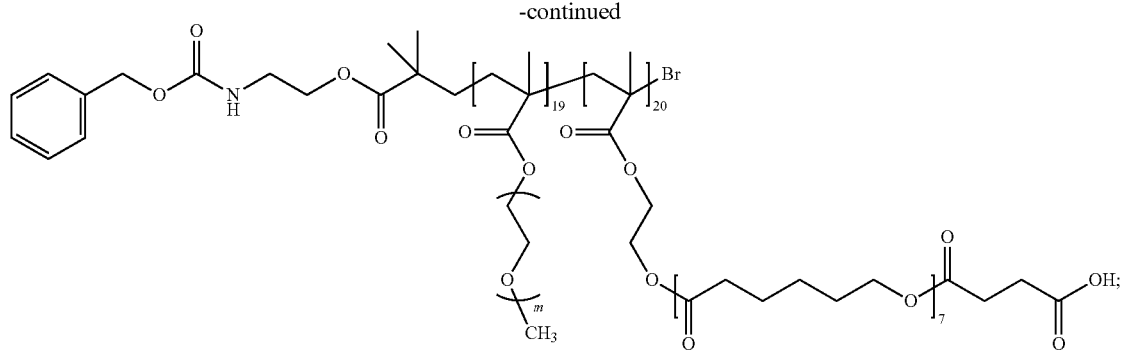
or a pharmaceutically acceptable salt thereof. In some embodiments, the second polymer comprises a net cationic charge. In some embodiments, the second polymer is further defined by the structure:
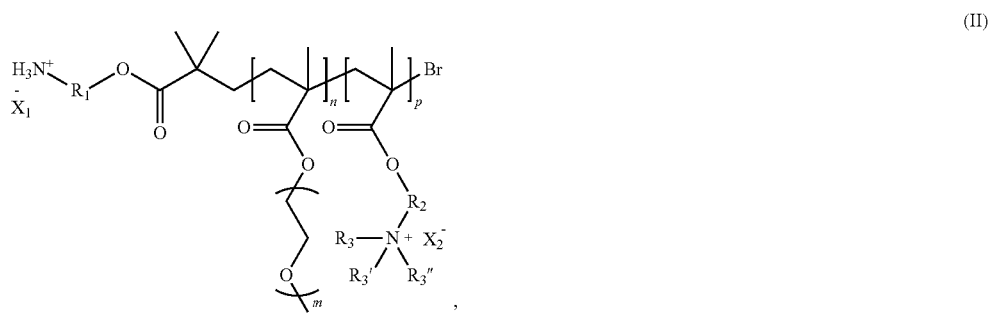
(II)
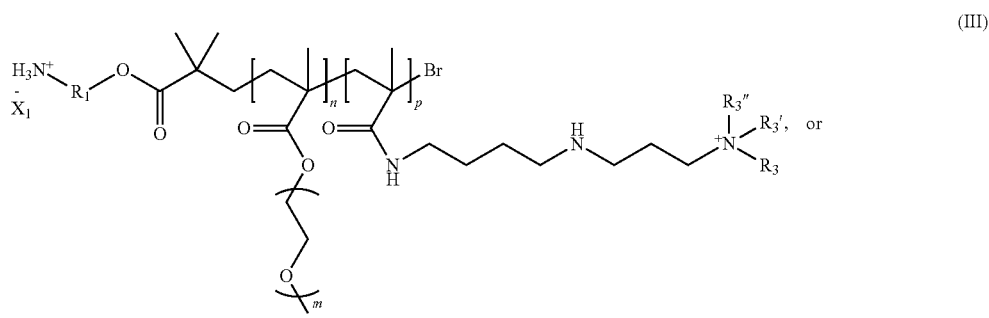
(III)
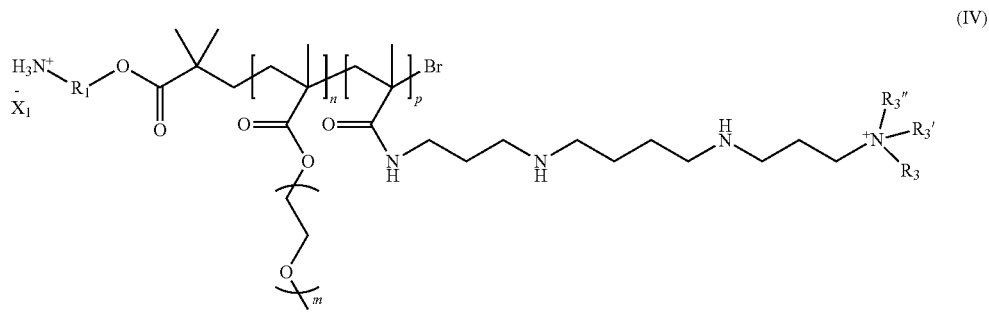
(IV)

wherein: m is 5-40 or 10-40; n is 10-40; p is 5-30; $R_1$ and $R_2$ are each independently alkanediyl$_{(C1-18)}$, arenediyl$_{(C6-12)}$, or a substituted version of either of these groups; $R_3$, $R_3'$, and $R_3''$ are each independently alkyl$_{(C1-8)}$, aryl$_{(C3-12)}$, or a substituted version of any of these groups; and $X_1$ and $X_2$ are each independently a monovalent anion; or a pharmaceutically salt thereof. In some embodiments, the second polymer is further defined by the formula:

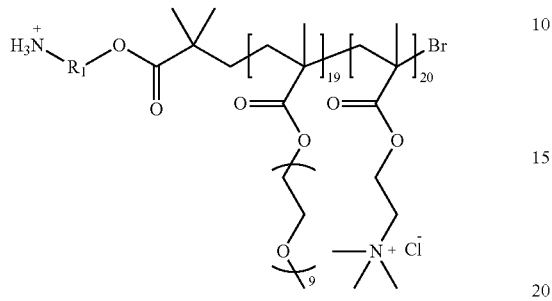

or a pharmaceutically acceptable salt thereof. In some embodiments, the first polymer has the structure:

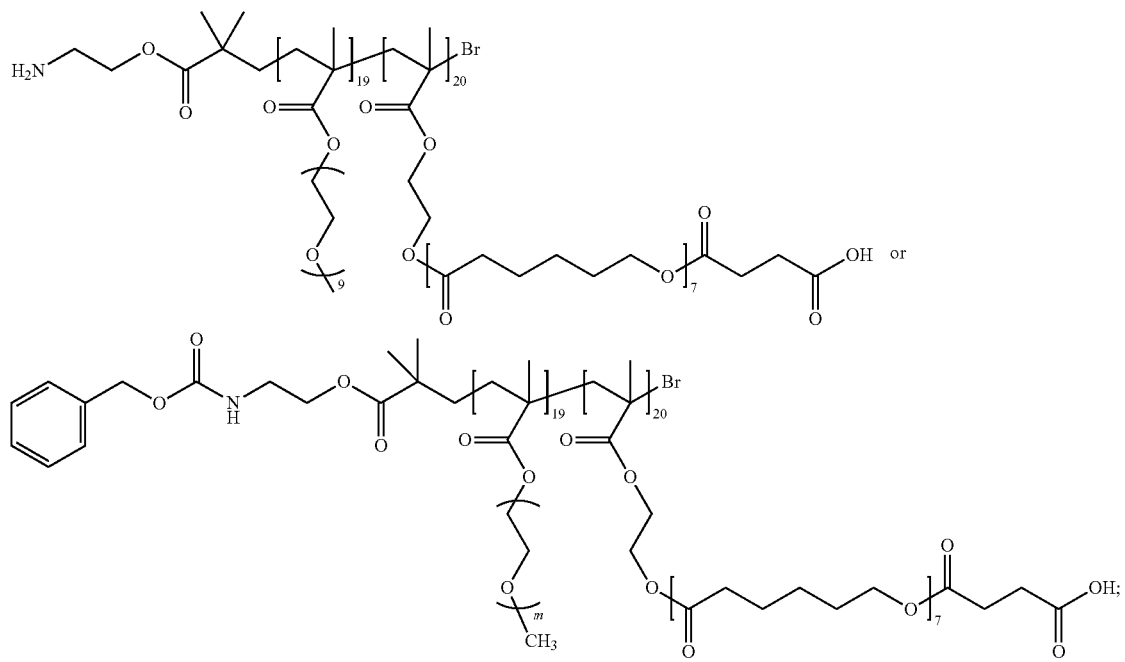

and wherein the second polymer has the structure:

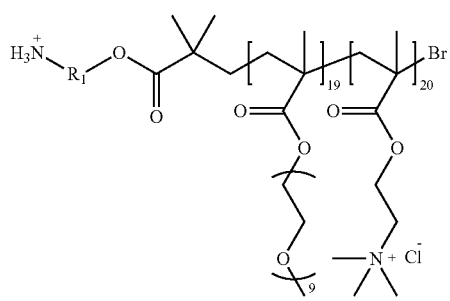

or a pharmaceutically acceptable salt thereof. In some embodiments, the ratio of the first polymer to the second polymer is from about 100:1 w/w to about 1:10 w/w, from about 100:1 w/w to about 1:1, from about 100:1 w/w to about 10:1, from about 10:1 w/w to about 1:1 w/w, or about 100:1 w/w, 50:1 w/w, 10:1 w/w, 5:1 w/w, or any range derivable therein. In some embodiments, the pharmaceutical composition comprises two therapeutic agents (e.g., two chemotherapeutic agents) that each independently treat or selectively target or bind tumors cells and/or tumor stroma cells. The therapeutic agent may be a chemotherapeutic such as, e.g., paclitaxel or cyclopamine. In some embodiments, the pharmaceutical composition comprises paclitaxel and cyclopamine. In some embodiments, the chemotherapeutic is GANT58, GANT61, vitamin D, or 17-N-allylamino-17-demethoxygeldanamycin (17-AAG). In some embodiments, the pharmaceutical composition comprises: (i) GANT58 and paclitaxel, (ii) GANT61 and paclitaxel, (iii) vitamin D and paclitaxel, (iv) GANT58 and 17-AAG, (v) GANT61 and 17-AAG, or (vi) vitamin D and 17-AAG. In some embodiments, the pharmaceutical composition is formulated for intravenous, intra-arterial, intraperitoneal, parenteral, subcutaneous, or intra-tumoral administration. In some embodiments, the pharmaceutical composition further comprises an excipient. The excipient may be a monosaccharide or a disaccharide (e.g., sucrose). In some embodiments, the concentration of the monosaccharide or disaccharide is from about 1% to about 10% (w/w). In some embodiments, the concentration of the excipient is about 5% (w/w).

Another aspect of the present invention relates to a method of treating a disease in a mammalian subject comprising administering a therapeutically effective amount of a pharmaceutical composition of the present invention or as defined above to the subject. In some embodiments, the disease is a cancer. The cancer may be a pancreatic cancer such as, e.g., pancreatic ductal adenocarcinoma (PDAC). In some embodiments, the pancreatic cancer is a pancreatic cancer in which one or more proteins in the sonic hedgehog signaling pathway is defective (e.g., the sonic hedgehog signaling pathway is upregulated). In some embodiments, the pancreatic cancer is a pancreatic cancer which the smoothened receptor (SMO) is misregulated (e.g., upregulated). In some embodiments, the cancer is liver cancer (e.g., hepatocellular carcinoma). In some embodiments, the cancer is ovarian cancer. The ovarian cancer may be a high grade serous carcinoma. In some embodiments, the cancer is basal-cell carcinoma. In some embodiments, the cancer is medulloblastoma. In some embodiments, the pharmaceutical composition comprises paclitaxel or cyclopamine. In some embodiments, the pharmaceutical composition comprises paclitaxel and cyclopamine. In some embodiments, the mammalian subject is a human. In some embodiments, the pharmaceutical composition may be administered to the subject in combination with a second therapeutic or anticancer therapy such as, e.g., a checkpoint inhibitor, an immunotherapy (e.g., a therapeutic antibody, an antibody fragment, or an immunotoxin), or a radiotherapy. In some embodiments, the method further comprises administering a checkpoint inhibitor, an immunotherapy, or a radiotherapy to the subject.

In some embodiments, a pharmaceutical composition may be administered to a patient in combination with one or more additional therapeutic agents. For example, the additional therapeutic agent may be an immunotherapy (e.g., to treat a cancer). For example, one or more therapeutic antibodies, antibody fragments (e.g., scFv, etc.), or immunotoxins may be administered to a subject, such as a human patient, in combination with a nanoparticle or micelle as described herein.

As used herein, "substantially free," in terms of a specified component, is used herein to mean that none of the specified component has been purposefully formulated into a composition and/or is present only as a contaminant or in trace amounts. The total amount of the specified component resulting from any unintended contamination of a composition is therefore below 0.05%. When used herein, the term "more substantially free" means below 0.01%. In some embodiments, when the term "essentially free" is used to describe a composition in which no amount of the specified component can be detected using standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 20A, Quantification of $^{64}$Cu-anti-PD1 in tumor-draining lymph nodes and Kras* tumor, showing a trend of increased distribution of the antibody, which recognizes PD1+ T cells, after M-CPA/PTX treatment. FIG. 20B, Autoradiographs of Kras* tumors obtained at 24 h after intravenous injection of $^{64}$Cu-anti-PD1, demonstrating more homogenous distribution of the antibody, which recognizes PD1+ T cells, after M-CPA/PTX treatment.

DESCRIPTION OF ILLUSTRATIVE EMBODIMENTS

Figure 1A:
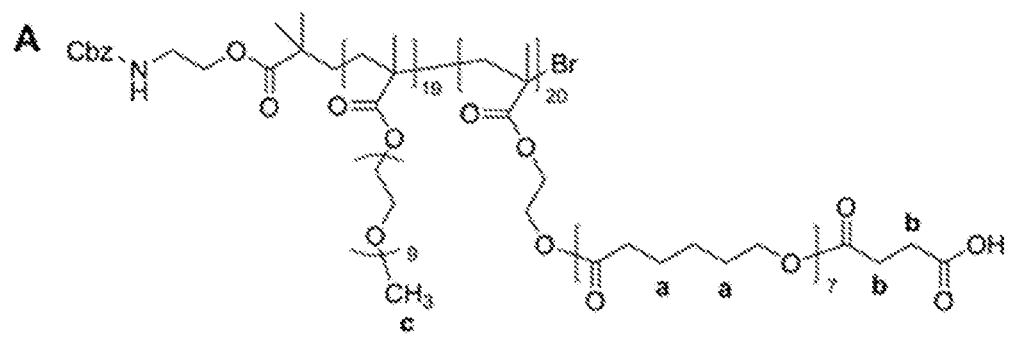
FIGS. 1A-1D: Chemical structures and $^1$H-NMR spectra of the polymers used to formulate the micelles. (A and C) Chemical structures of the anionic polymer (A) and cationic polymer (C). (B and D) $^1$H-NMR spectra of the anionic polymer (B) and cationic polymer (D). The bold lowercase letters indicate the characteristic chemical shifts of protons.
Figure 1B:
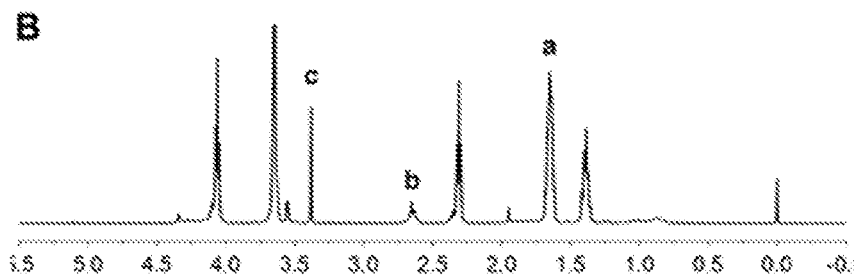
Figure 1C:
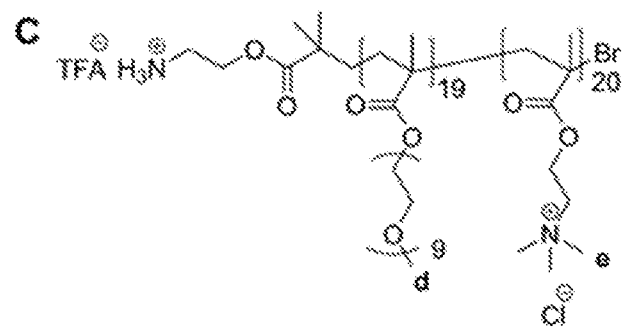
Figure 1D:
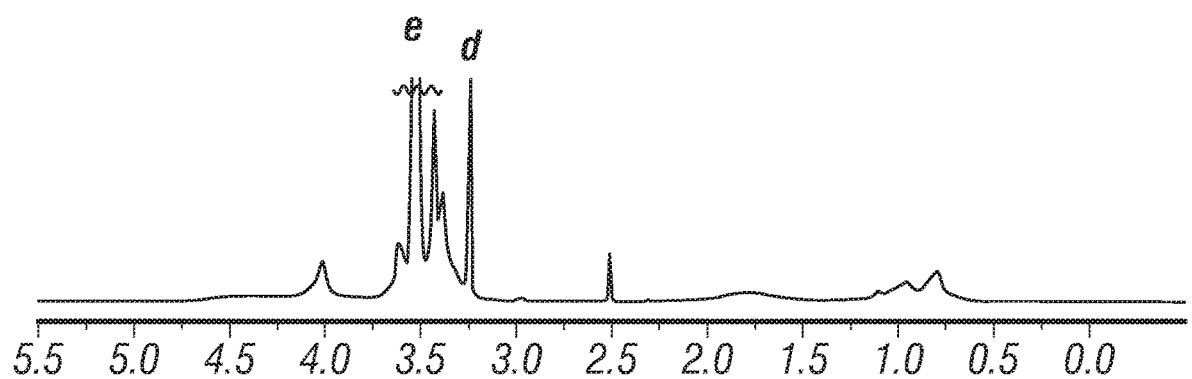

In some aspects, the present disclosure provides comb-like polymer structures which are used to form micelles for the delivery of drugs. These micelles may be used to treat disease such as cancer by improving the delivery of one or more therapeutic agent in vivo. In some embodiments, these polymers also slow the release of one or more of the therapeutic agents within the body.

I. POLYMER COMPOSITIONS

In some aspects, the present disclosure presents polymers comprising a polyacrylate backbone which contains blocks of a plurality of PEG sidechains and a plurality of sidechains resulting from a ring opening polymerization. In some embodiments, the polyacrylate backbone is terminated with a group traditionally characteristic of a radical polymerization technique such as atom-transfer radical polymerization (ATRP). Some non-limiting examples of such chemical groups include hydrogen, hdyroxy, or halides. In some embodiments, the polyacrylate backbone may be capped with a C1-C8 aminoalkyl such as ethanolamine or amine protected aminoalkyl such as, e.g., benzyl N-(2-hydroxyethyl)carbamate (N-Cbz-ethanoamine) The polymers described herein may contain either a polyacrylic acid backbone or a polyacrylamide backbone. In some embodiments, the backbone of the polymer is a polyacrylic acid backbone. In some embodiments, the carboxylic acid of the polyacrylic acid backbone is esterified with a polyethylene glycol group to obtain a PEG sidechain. Polyethylene glycol is a polymer of ethylene glycol repeating units which the terminus is a hydroxyl group or is capped with a methyl group. The polymers described herein comprise a polyacrylate backbone with from 10 monomers to 40 monomers with PEG sidechains. In some embodiments, the number of monomers with PEG sidechains is from 16 to 22 monomers. The number of monomers in the polymer of the present disclosure is preferably from 10, 12, 14, 15, 16, 17, 18, 19, 20, 21, 22, 23, 24, 26, 28, 30, 32, 34, 36, 38, to 40, or any range derivable therein. In some embodiments, the number of monomers with PEG sidechains is 19.

In some embodiments, the polyacrylate backbone further comprises monomers wherein the carboxylic acid has been esterified with a polymer derived from the ring opening of a lactone. In some embodiments, the polymer resulting from a ring opening is a polycaprolactone. The polycaprolactone may be esterified to the carboxylic acid through an ethylene glycol linker or cyclic anhydride. In some embodiments, the number of monomers with polycaprolactone sidechains is from 10 to 40 monomers, more preferably from 16 to 22 monomers. The number of monomers in the polymer of the present disclosure is from 10, 12, 14, 15, 16, 17, 18, 19, 20, 21, 22, 23, 24, 26, 28, 30, 35, to 40, or any range derivable therein. In some embodiments, the number of monomers with polycaprolactone sidechains is 20. In some embodiments, the terminus of the polycaprolactone is esterified with a carboxylic acid linked to another group which has a net negative charge at physiological pH. In some embodiments, the group is a phosphonate, a sulfonate, or a second carboxylic acid. In some embodiments, the terminus of the polycaprolactone is esterified with butanedioic acid (succinic acid), pentanedioic acid, or hexanedioic acid. In some embodiments, the terminus of the polycaprolactone is esterified with succinic acid. In some aspects, the polymer has a net negative charge. In some embodiments, the present disclosure provides a polymer of the formula:

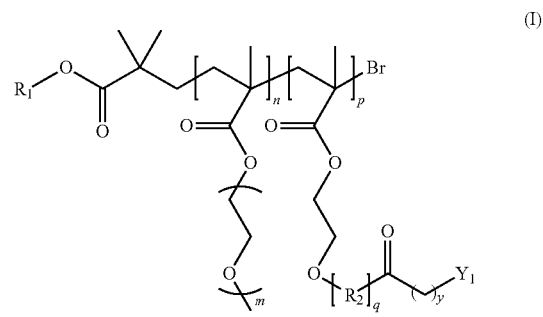

(I)

wherein:

$R_1$ is alkyl$_{(C1-18)}$, cycloalkyl$_{(C1-18)}$, aryl$_{(C1-18)}$, or a substituted version of any of these groups; or an alkyl$_{(C1-18)}$ substituted with a protected amine group;

$R_2$ is a group of the formula:

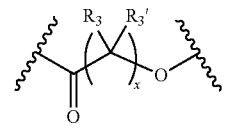

wherein:

$R_3$ and $R_3'$ are each independently hydrogen, alkyl$_{(C1-6)}$, or substituted alkyl$_{(C1-6)}$; and x is 1-10;

m is 5-40 or 10-40;

n is 10-40;

p is 5-40 or 5-20;

q is 1-20 or 1-10;

y is 1-10; and $Y_1$ is carboxy, phosphonate, or hydroxysulfonyl;

or a pharmaceutically salt thereof.

In some non-limiting examples, formula I is poly[oligo(ethylene glycol) methyl ether methacrylate]-b-poly[2-(methacryloyloxy)ethoxy-oligo(ε-caprolactone)-4-oxobutanoic acid] or

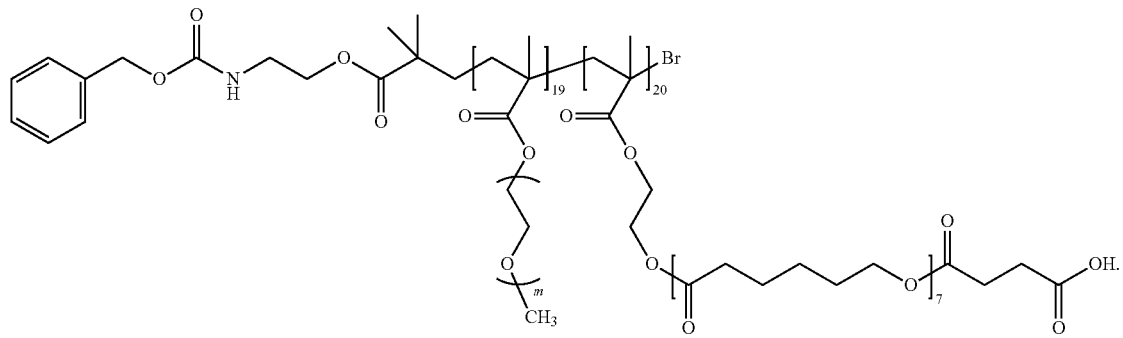

In some aspects, the present disclosure provides a second polymer containing one or more polyacrylate with a plurality of PEG sidechains and a plurality sidechains terminated with quaternary amine. In some embodiments, the carboxylic acid of the polyacrylic acid backbone in the second polymer is esterified with a polyethylene glycol group to obtain a PEG sidechain. Polyethylene glycol is a polymer of ethylene glycol repeating units which the terminus is a hydroxyl group or is capped with a methyl group. The polymers described herein comprise a polyacrylate backbone with from 10 monomers to 40 monomers with PEG sidechains. In some embodiments, the number of monomers with PEG sidechains is from 16 to 22 monomers. The number of monomers in the polymer of the present disclosure is from 10, 12, 14, 15, 16, 17, 18, 19, 20, 21, 22, 23, 24, 26, 28, 30, 35, to 40, or any range derivable therein. In some embodiments, the number of monomers with PEG sidechains is 19.

In some embodiments, the carboxylic acid of the polyacrylic acid backbone in the second polymer is esterified with a quaternary amine groups. The polymers described herein comprise a polyacrylate backbone with from 10 monomers to 40 monomers with sidechains terminated with quaternary amines. The number of monomers in the polymer of the present disclosure is from 10, 12, 14, 15, 16, 17, 18, 19, 20, 21, 22, 23, 24, 26, 28, 30, 35, to 40, or any range derivable therein. In some embodiments, the number of monomers with choline sidechains is 20. In some embodiments, the polymers described herein comprise a polyacrylate backbone with from 10 monomers to 40 monomers with choline side chains. In some embodiments, the second polymer comprises a net positive charge. In some embodiments, the present disclosure provides a second polymer of the formula:

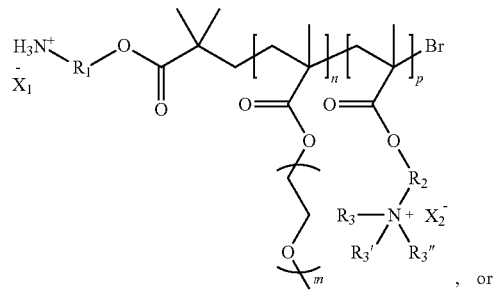

(II)

, or

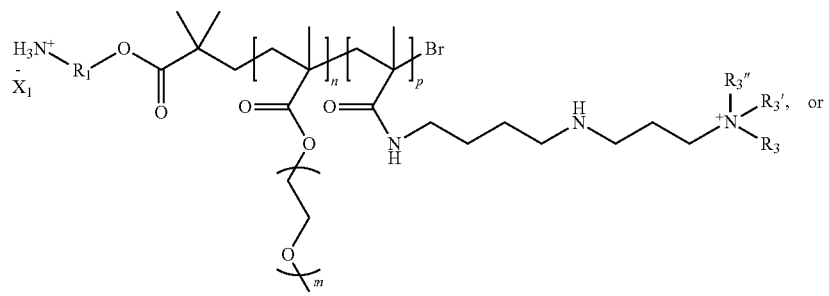

With Spermidine Pendent

-continued

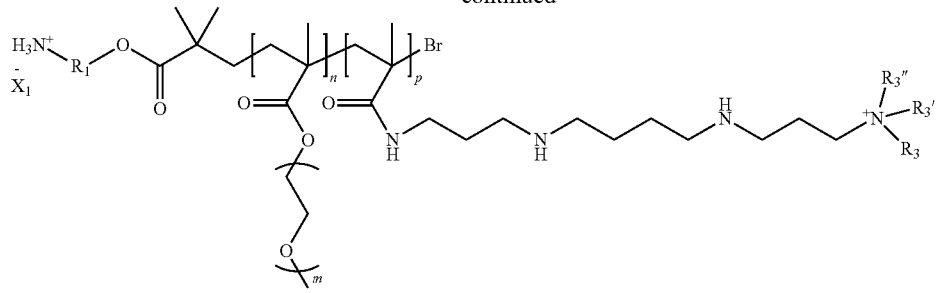

With Spermine Pendent wherein:
  m is 5-40 or 10-40;
  n is 10-40;
  p is 5-30;
  $R_1$ and $R_2$ are each independently alkanediyl$_{(C1-8)}$, arenediyl$_{(C6-12)}$, or a substituted version of either of these groups;
  $R_3$, $R_3'$, and $R_3''$ are each independently alkyl$_{(C1-8)}$, aryl$_{(C3-12)}$, or a substituted version of any of these groups; and
  $X_1$ and $X_2$ are each independently a monovalent anion;
or a pharmaceutically salt thereof.

For example, Structure II can be ammonium capped poly[oligo(ethylene glycol) methyl ether methacrylate]-b-poly{[2-(methacryloyloxy)ethyl]trimethylammonium chloride}, as shown below:

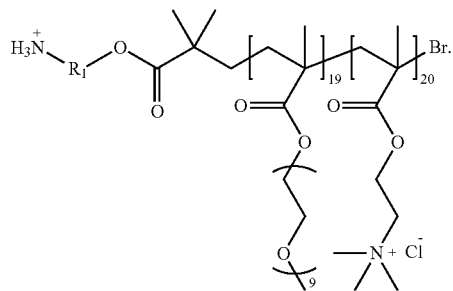

II. MICELLE COMPOSITIONS

In some aspects, the present disclosure provides a nanoparticle or micelle prepared from a polymer described herein. Within the context of this disclosure, the term micelle and nanoparticle are used interchangeably. In some embodiments, the nanoparticle or micelle comprises a mixture of a first polymer and a second polymer wherein the first polymer has a net negative charge and the second polymer has a net positive charge. These nanoparticles or micelles may comprises a mixture of the first polymer to the second polymer in a ratio from about 100:1, 90:1, 80:1, 70:1, 60:1, 55:1, 50:1, 45:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, to about 1:10, or any range derivable therein. In some embodiments, the ratio is from about 10:1 to about 1:1 or from about 100:1 to about 10:1.

In some aspects, the micelles are loaded with one or more therapeutic agents. In some embodiments, these therapeutic agents are chemotherapeutics. In some embodiments, the micelles are loaded with one therapeutic agent. In other embodiments, the micelles are loaded with two or more therapeutic agents. In some embodiments, the two therapeutic agents may act synergistically to obtain the desired therapeutic results. As such, the two therapeutic agents may target different molecular mechanisms associate with the disease or disorder.

In some aspects, the micelles prepared with different therapeutic agents may show a number average size from about 25 nm to about 250 nm. In some embodiments, the size is from about 40 nm to about 150 nm. In some embodiments, the size of the micelles may be from about 30 nm, 40 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, to about 150 nm, or any range derivable therein. Furthermore, the micelles may have a polydispersity index (PDI) of less than 0.20. In some embodiment, the micelles may have a PDI of 0.05 to 0.15. In some embodiments, the micelles have a PDI of less than 0.2. Both micelle size and PDI may be determined by dynamic light scattering at a 90° scatter angle using a particle electrophoresis system using methods known to a person of skill in the art.

In some embodiments, the micelle have high relative loading of the therapeutic agents. The relative loading yield of the therapeutic agent may be greater than 85%. In some embodiments, it may be greater than 95%. In some embodiments, it may be greater than 98%. Furthermore, the amount of each therapeutic agent loaded in the micelle may comprise from about 1% w/w to about 15% w/w. In some embodiments, the amount of therapeutic agent is from 1%, 2%, 2.5%, 3%, 4%, 4.5%, 5%, 5.5%, 6%, 7%, 8%, 9%, 10% w/w to 15%, or any range derivable therein. In some embodiments, the amount of each therapeutic agent is about 5%-10% w/w. In other embodiments, when two or more therapeutic agents are used each therapeutic agent comprises about 2.5%-5% w/w of one of the polymers.

In some embodiments, the micelles described in the present disclosure may have increased stability. The micelles may show less than a 10% loss of therapeutic agent after storage for 90 days. In some embodiments, the micelles show a loss of less than 5% after a 90 day storage period. In some embodiments, the micelles show a loss of less than 5%, 4.5%, 4%, 3.5%, 3%, 2.5%, 2%, 1.5%, or 1%. Furthermore, when stored for a period of about 90 days, the particles show a change in size and PDI of less than 30%. In some embodiments, the change in size and PDI is less than 25%.

III. PHARMACEUTICAL PREPARATIONS

In some embodiments, the micelles may be formulated as a pharmaceutical or therapeutic composition appropriate for the intended application. The therapeutic compositions of the present embodiments are administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising additional active ingredients will be known to those of skill in the art in light of the present disclosure. In some non-limiting examples, the pharmaceutical composition may further comprise a peptide or an antibody on the surface of the micelle, nanoparticle, or liposome or may be administered as a co-therapy. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, monosaccharide and/or disaccharides, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent may be taken every morning and/or every evening, regardless of when the subject has eaten or will eat.

The active compounds can be formulated for parenteral administration, e.g., formulated for injection via the intravenous, inraarterial, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, iodinated oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The therapeutically compositions may be formulated into a neutral or salt form. Pharmaceutically acceptable salts, include the acid addition salts (such as those formed with the free amino groups of the polymer) and which are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Additionally, the pharmaceutical or therapeutic compositions may comprises one or more polycationic peptides or proteins such as protamine, polylysine, or polyarginine such that the therapeutic agent is formulated as a neutral salt or as a complex which contains significantly reduced charge.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. In some embodiments, the sugar used is 5% sucrose. Prolonged absorption of the injectable compositions can be brought about by the use in the compositions of agents delaying absorption, for example, aluminum monostearate and gelatin.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered.

IV. CANCERS

In some embodiments, one or more nanoparticles or micelles as described herein may be used to treat a cancer. The cancer may be a solid tumor, metastatic cancer, or non-metastatic cancer. In some embodiments, the cancer is a pancreatic cancer such as, e.g., a pancreatic ductal adenocarcinoma. For example, in some embodiments, a nanoparticle or micelle of the present invention may be used to deliver a combination of chemotherapeutic agents (e.g., paclitaxel and cyclopamine) to treat a pancreatic cancer, ovarian cancer, or liver cancer.

It is anticipated that the nanoparticles may be used to treat a wide variety of cancers in a mammalian subject, such as a human patient. For example, cancer cells that may be treated with cell targeting constructs according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia, and medulloblastoma.

In addition to cancers, nanoparticles or micelles of the present invention may be used to deliver a therapeutic to treat other diseases. The present invention can find application in the treatment of any disease for which delivery of a drug, small molecule therapeutic, therapeutic protein, therapeutic nucleic acid, small interfering RNA (siRNA), or microRNA (mRNA) to a cell or tissue of a subject is believed to be of therapeutic benefit. Examples of such diseases include hyperproliferative diseases, inflammatory diseases, infectious diseases, degenerative diseases, and autoimmune diseases.

V. THERAPEUTIC AGENTS

In some embodiments, a nanoparticle or micelle as described herein may be used to deliver a therapeutic agent such as a small molecule therapeutic, or a gene therapy (e.g., a siRNA, a miRNA, an antisense, a therapeutic gene, etc.), or other therapeutic agent to a subject, such as a mammalian subject or a human.

a. Chemotherapeutic Agents

In some embodiments, one or more anticancer therapeutic agent(s), anticancer drug(s), or chemotherapeutic(s) may be included in a nanoparticle or micelle as described herein. For example, in some aspects the chemotherapeutic agent is a protein kinase inhibitor such as a EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. Nonlimiting examples of protein kinase inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016 or a mixture thereof.

Yet further combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegal1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above. In certain embodiments, the compositions provided herein may be used in combination with gefitinib. In other embodiments, the present embodiments may be practiced in combination with Gleevac. In certain embodiments, one or more chemotherapeutic may be used in combination with the compositions provided herein.

In some embodiments, the therapeutic agent is a transcriptional factor inhibitor such as a hedgehog pathway inhibitor or a NF-κB inhibitor. Nonlimiting examples of hedgehog pathway inhibitors include GANT61, GANT58, LDE225 (Sonidegib), LEQ 506, PF-04449913 (Glasdegib), TAK-441, IPI-926 (Saridegib), BMS 833923, LY2940680 (Taladegib), and GDC-0449 (Vismodegib). In some embodiments, the therapeutic agent is a vitamin. Nonlimiting examples of vitamins include vitamin D and vitamin D analogues. The therapeutic agent may be a naturally occurring anticancer agents. For example, nonlimiting examples of such naturally occurring agents include geldanamycin and its derivative 17-N-allylamino-17-demethoxygeldanamycin (17-AAG), triptolide, and related analogues.

b. Gene Therapies

In yet another embodiment, a gene therapy (e.g., a siRNA, a miRNA, an antisense, a therapeutic gene, a nucleic acid encoding a therapeutic protein, etc.) may be included in a nanoparticle or micelle as described herein.

c. Anti-inflammatory Agents

In some embodiments, one or more anti-inflammatory agents may be included in a nanoparticle or micelle as described herein. The anti-inflammatory agent may be a steroid or a non-steroidal anti-inflammatory agent. Non-steroidal anti-inflammatory agents include a class of drugs used in the treatment of inflammation and pain. The exact mode of action of this class of drugs is unknown. Examples of members of this class of agents include, but are not limited to, ibuprofen, ketoprofen, flurbiprofen, nabumetone, piroxicam, naproxen, diclofenac, indomethacin, sulindac, tolmetin, etodolac, flufenamic acid, diflunisal, oxaprozin, rofecoxib, and celecoxib. One of ordinary skill in the art would be familiar with these agents. Included in this category are salicylates and derivates of salicylates, such as acetyl salicylic acid, sodium salicylate, choline salicylate, choline magnesium salicylate and diflunisal.

Other anti-inflammatory agents include anti-rheumatic agents, such as gold salts (e.g., gold sodium thiomalate, aurothioglucose, and auranofin), anti-rheumatic agents (e.g., chloroquine, hydroxychloroquine, and penicillamine), antihistamines (e.g., diphenhydramine, chlorpheniramine, clemastine, hydroxyzine, and triprolidine), and immunosuppressive agents (e.g., methotrexate, mechlorethamine, cyclophosphamide, chlorambucil, cyclosporine, and azathioprine). Other immunosuppressive agent contemplated include tacrolimus and everolimus. Tacrolimus suppresses interleukin-2 production associated with T-cell activation, inhibits differentiation and proliferation of cytotoxic T cells. One of ordinary skill in the art would be familiar with these agents, and other members of this class of agents, as well as the mechanism of actions of these agents and indications for use of these agents.

VI. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; "phosphonate" means —P(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxysulfonyl" means —S(O)$_2$OH or a deprotonated form thereof; "sulfonamide" means —S(O)$_2$NH$_2$; and "sulfinyl" means —S(O)—.

In the context of chemical formulas, the symbol "—" means a single bond, "=" means a double bond, and "≡" means triple bond. The symbol " ---- " represents an optional bond, which if present is either single or double. The symbol " ==== " represents a single bond or a double bond. Thus, for example, the formula

includes

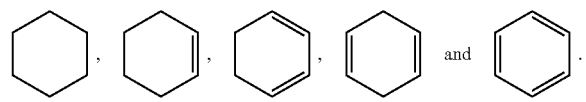

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ∿∿∿ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "▮▮▮▮" means a single bond where the group attached to the thick end of the wedge is "into the page". The symbol " ∿∿∿ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

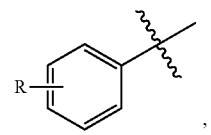

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

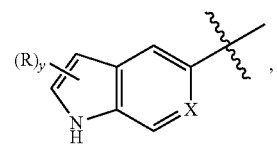

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

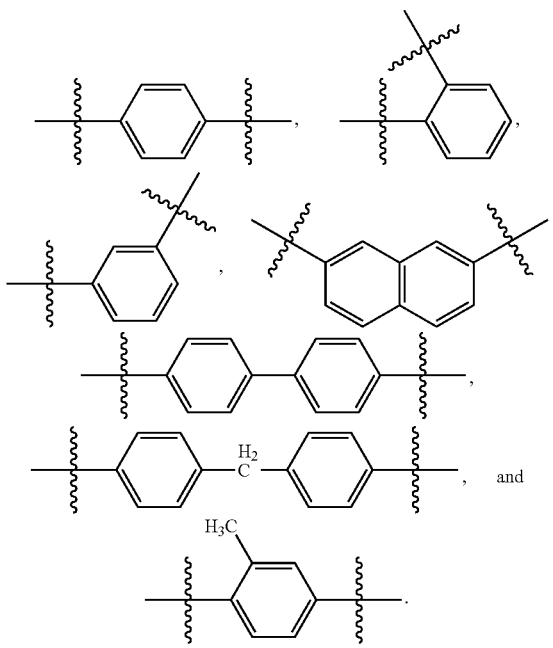

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

An "amine protecting group" is well understood in the art. An amine protecting group is a group which prevents the reactivity of the amine group during a reaction which modifies some other portion of the molecule and can be easily removed to generate the desired amine Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). The term "protected amine group" references to an amine radical which is substituted on another groups comprising one or more monovalent amine protecting groups or a divalent amine protected group.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Materials. Common chemical reagents were purchased from Sigma-Aldrich (St. Louis, Mo.) or VWR (West Chester, Pa.) and used as received. CPA-BODIPY was purchased from Toronto Research Chemicals Inc. (Toronto, Canada). $^1$H and $^{13}$C NMR spectra were recorded on a Bruker Avance 600 spectrometer (Billerica, Mass.) with tetramethyl silane as internal standard.

Preparation of micelles loaded with CPA and/or PTX. The anionic and cationic polymers used to formulate the micelles (FIG. 1) were prepared using atom transfer radical polymerization and ring-opening polymerization. The detailed procedures for polymerization and polymer characterization are described in Example 2. For preparation of CPA-loaded micelles (M-CPA), 5 mg of CPA was added to 200 µL of ethanol, and the solution was warmed to 50° C. to completely dissolve the CPA. Anionic polymer (100 mg) was dissolved in 0.8 mL of tetrahydrofuran, this solution was added to the CPA-ethanol solution, and the resulting solution was incubated at room temperature for 10 min with agitation. Cationic polymer (20 mg) was dissolved in 2 mL of deionized water, and this solution was pipetted into the CPA—anionic polymer solution under violent vortexing at room temperature. The mixture was vortexed for another 1 min after addition of cationic polymer was complete. Tetrahydrofuran and ethanol were removed on a rotary evaporator under 130 mBar at 45° C. for 10 min, after which the polymer was purified by dialysis against deionized water at 4° C. Un-encapsulated drug was removed by centrifugation at 5000 RPM for 5 min. The supernatant was collected and filtered through a sterile 0.22-µm nylon filter before use. For long-term storage, the micelles were mixed with sucrose solution (50% by weight in water at a volume ratio of 9:1) and then frozen in a —80° C. freezer. Micelles loaded with PTX or both CPA and PTX were prepared similarly.

Characterization of drug-loaded micelles. Drug-loaded micelles were characterized with respect to size, surface charge, drug loading, drug release, and morphology. Particle size and surface charge were measured using dynamic light scattering at a 90° scatter angle on a ZetaPlus particle electrophoresis system (Brookhaven Instruments Corp., Holtsville, N.Y.). To determine drug loading, micelle suspensions were dissociated in ethanol and sonicated for 5 min to release the encapsulated drugs. After centrifugation at 13,000 RPM for 15 min, the supernatant was analyzed using an Agilent 1100 series high-performance liquid chromatography (HPLC) (Santa Clara, Calif.). The mobile phase was a mixture of 0.1% trifluoroacetic acid (solvent A) and acetonitrile (solvent B), using a gradient (solvent B from 5% to 95% v/v in 30 min). The column was an Agilent C18 column (4.6×250 mm) with 5-µm particles. The flow rate was 1.0 mL/min, and the detection wavelength was 210 nm for CPA and 227 nm for PTX. To determine drug release, micelles were added to a microdialyzer (molecular weight cut-off ~3000) and incubated in PBS (pH 7.4) or sodium acetate buffer (pH 6.0 and pH 5.2) at 37° C. with agitation. At predetermined time points, 20 µL of the solution inside the dialyzer was retrieved and centrifuged at 5000 RPM for 5 min. Aliquots of the supernatant (10 µL) were analyzed using HPLC to determine the concentrations of CPA and PTX. The retention times of CPA and PTX were 14.7 min and 19.6 min, respectively.

The morphology of drug-loaded micelles was examined by transmission electron microscopy (TEM). Samples were placed on 100 mesh formvar-coated copper grids treated with poly-L-lysine and left for 1 h. The grids were blotted with filter paper to remove excess samples and then stained with filtered 1% uranyl acetate for 1 min. Stain was blotted from the grids with filter paper, and the samples were allowed to dry. TEM was performed on a JEM 1010 transmission electron microscope (JEOL USA, Inc., Peabody, Mass.) at an accelerating voltage of 80 kV. Digital images were collected using the AMT Imaging System (Advanced Microscopy Techniques Corp., Danvers, Mass.).

Cell lines. Three pancreatic cancer cell lines were obtained from American Type Culture Collection: Miapaca-2 (high CPA sensitive), L3.6pl (moderately CPA sensitive) (Feldmann et al., 2007), and Panc-1 (CPA resistant) (Feldmann et al., 2007).

Assays of cell proliferation and clonogenicity. Cells were seeded at 2000 cells/well in 96-well plates and treated at 37° C. for 72 h before MTS [3-(4,5-dimethylthiazol-2-yl)-5-(3-carboxymethoxyphenyl)-2-(4-sulfophenyl)-2H- tetrazolium] assay. The proportion of viable cells was normalized to that of untreated cells and expressed as mean±standard error of the mean (n=6). Clonogenicity assay was performed as previously reported (Shoemaker et al., 1985). Cells were seeded at 1000 cells per 10-cm plate in growth medium overnight and treated at 37° C. for 10 days. At the end of this 10-day period, colonies were fixed with formalin and stained with crystal violet. Colonies with more than 20 cells were counted.

SMO competition assay. SMO competition assay was performed using a commercial fluorescent SMO ligand, CPA-BODIPY (Bee et al., 2012). Cells in 96-well plates were first treated with M-CPA for 24 h at 37° C. CPA-BODIPY (10 nM) was then added to the cells, and cells were incubated for another 4 h. Then the treatment solutions were removed, and cells were washed with PBS and lysed with DMSO. The residual fluorescence of each well was recorded ($\lambda_{ex}$=480 nm, $\lambda_{em}$=525 nm). For fluorescence images, cells were fixed with methanol, counterstained with Hoechst, and observed using a Zeiss Axio Observer.Z1 fluorescence microscope (Carl Zeiss MicroImaging GmbH, Thornwood, N.Y.).

Western blot analysis. Cell lysate was fractioned and transferred to a polyvinylidene fluoride membrane (Millipore, Billerica, Mass.). Membranes were blotted with rabbit anti-human monoclonal Gli-1 antibody (Abcam Inc., Cambridge, Mass., 1:1000 dilution) and visualized using fluorescent IRDye 680RD goat anti-rabbit IgG (H+L) (LI-COR, Lincoln, Nebr., 1:5000 dilution). Beta-actin (Sigma-Aldrich) was used as an internal control to ensure equal protein loading.

Flow cytometry analysis of CD133 stem cell marker and tumorsphere formation. Miapaca-2 cells were treated with M-CPA and/or M-PTX at concentrations close to their respective $IC_{50}$ values: 10 µM for M-CPA and 10 nM for M-PTX. Treated cells were detached, and stained with mouse anti-human CD133 antibody—phycoerythrin conjugate (Miltenyi Biotec Inc., San Diego, Calif.). Mouse IgG-phycoerythrin was used as a negative control. Cell suspensions were analyzed using flow cytometry (BD FACSCalibur, San Jose, Calif.). Tumorspheres were cultured in 24-well ultralow attachment plates as previously reported (Hermann et al., 2007). Miapaca-2 cells in monolayer were detached and re-suspended at 1000 cells/well in sphere-forming medium consisting of DMEM/F-12 with B-27, N-2, 20 ng/mL epidermal growth factor, 20 ng/mL basic fibroblast growth factor, and 4 µg/mL heparin. M-CPA and/or M-PTX was added at the beginning of incubation. After 10 days of incubation, tumorspheres larger than 50 µm in each well were counted under a microscope.

Assays of antitumor efficacy in mice with orthotopic xenografts. All animal studies were approved by the Institutional Animal Care and Use Committee of The University of Texas MD Anderson Cancer Center and were carried out in accordance with institutional guidelines. Orthotopic Miapaca-2-luc pancreatic tumor xenografts were established in female NCR nude mice (Taconic, Hudson, N.Y.). A small incision was made in the left abdomen of each mouse. Directly into the pancreas was injected 50 µL of cell suspension ($1\times10^6$ Miapaca-2-luc cells and $3\times10^6$ HPSCs) in a 1:1 volume mixture of Hank's balanced salt solution and Matrigel. The incision was closed with absorbable sutures, and the tumors were allowed to grow for 4 weeks before treatment. Mice were randomly assigned to four different groups consisting of 9 mice per group and treated with (1) saline (control); (2) M-CPA, 10 mg/kg/injection, 3 injections in 1 week; (3) M-PTX, 10 mg/kg/injection, 3 injections in 1 week; or (4) M-CPA/PTX, 10 mg/kg/drug/injection, 3 injections in 1 week. Luciferase activity was monitored weekly by intraperitoneal injection of D-luciferin (150 mg/kg) according to the manufacturer's instructions. The luminescence signals were recorded up to 20 min after D-luciferase injection and the peak value was recorded using a Xenogen IVIS-200 optical system (Perkin Elmer, Waltham, Mass.).

Immunohistochemical staining. Formalin-fixed, paraffin-embedded tumor sections were deparaffinized and rehydrated. After antigen retrieval, slides were blocked in PBS with 10% goat serum and incubated with primary antibodies overnight at 4° C. The antibody dilutions were as follows: a-smooth muscle actin, 1:100; CD31, 1:50; Ki67, 1:400; and Gli-1, 1:100 (Abcam Inc.). Slides were washed and incubated with biotinylated goat-anti-rabbit IgG (1:200) (Vector Labs, Burlingame, Calif.) and streptavidin-conjugated horseradish peroxidase (DAKO, Carpinteria, Calif.) for 30 min each. A positive reaction was detected by exposure to 3,3'-diaminobenzidine. Slides were counterstained with hematoxylin and visualized under a microscope. Staining was quantified using at least 10 randomly selected 20× fields of view. For Ki67 staining, the positively stained nuclei were counted and recorded in each field of view. For CD31 and α-SMA staining, the percentage of positively stained pixels in the total pixels within each field of view was recorded using Image J software.

Statistics. Values are expressed as mean±standard error of the mean. Data were evaluated using Student's t test or one-way analysis of variance. A p value of less than 0.05 was considered statistically significant.

Example 2—Preparation of Polymers 2-(benzyloxycarbonyl amino) ethyl 2-bromo-isobutyrate (initiator 1).

Figure 9:
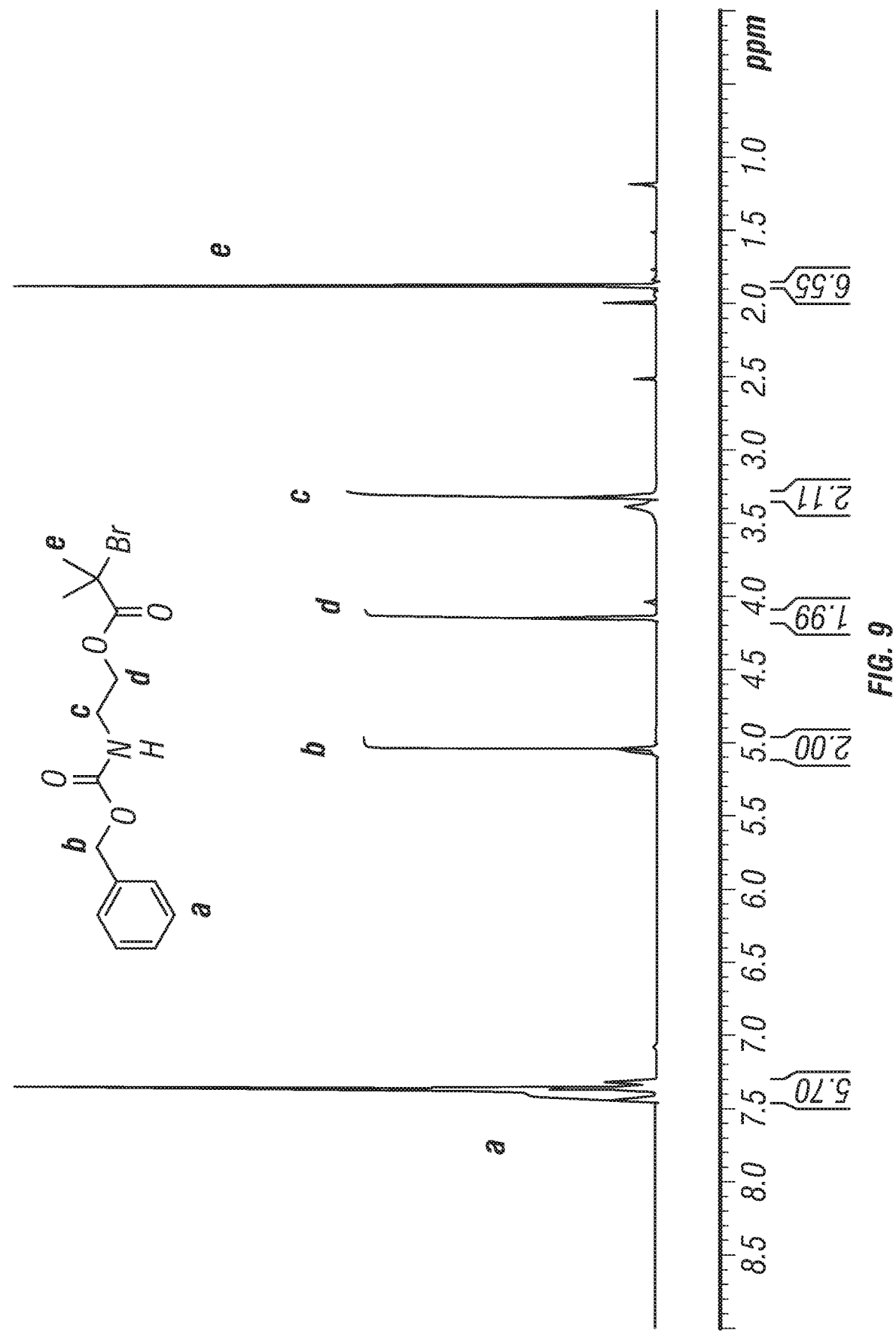
FIG. 9: $^1$H-NMR spectrum of 2-(benzyloxycarbonyl amino) ethyl 2-bromo-isobutyrate (initiator 1). Hydrogen atoms and their corresponding peak integrations are marked by lowercase letters.

Cbz-N-ethanolamine 2.0 g (10.2 mmol) and triethylamine (1.6 mL, 11.3 mmol) were dissolved in 25 mL of ethyl acetate and cooled with an ice-water bath. 2-Bromoisobutyryl bromide (1.3 mL, 10.7 mmol) in 5 mL of ethyl acetate was slowly dropped in under vigorous stirring. The mixture was stirred at room temperature for another 4 hr and then filtered to remove the precipitate. The ethyl acetate solution was subsequently washed with saturated $NaHCO_3$, 5% HCl, and double-distilled water; dried over anhydrous $MgSO_4$; and condensed in vacuo at 35° C. The crude product was purified via flash silica column using ethyl acetate/hexane as eluent to give colorless viscous oil 3.1 g (88%). $^1$H-NMR (ppm): 7.3~7.5 (5H), 5.05 (2H), 4.15 (2H), 3.30 (2H), 1.87 (6H) (FIG. 9).

Figure 10:
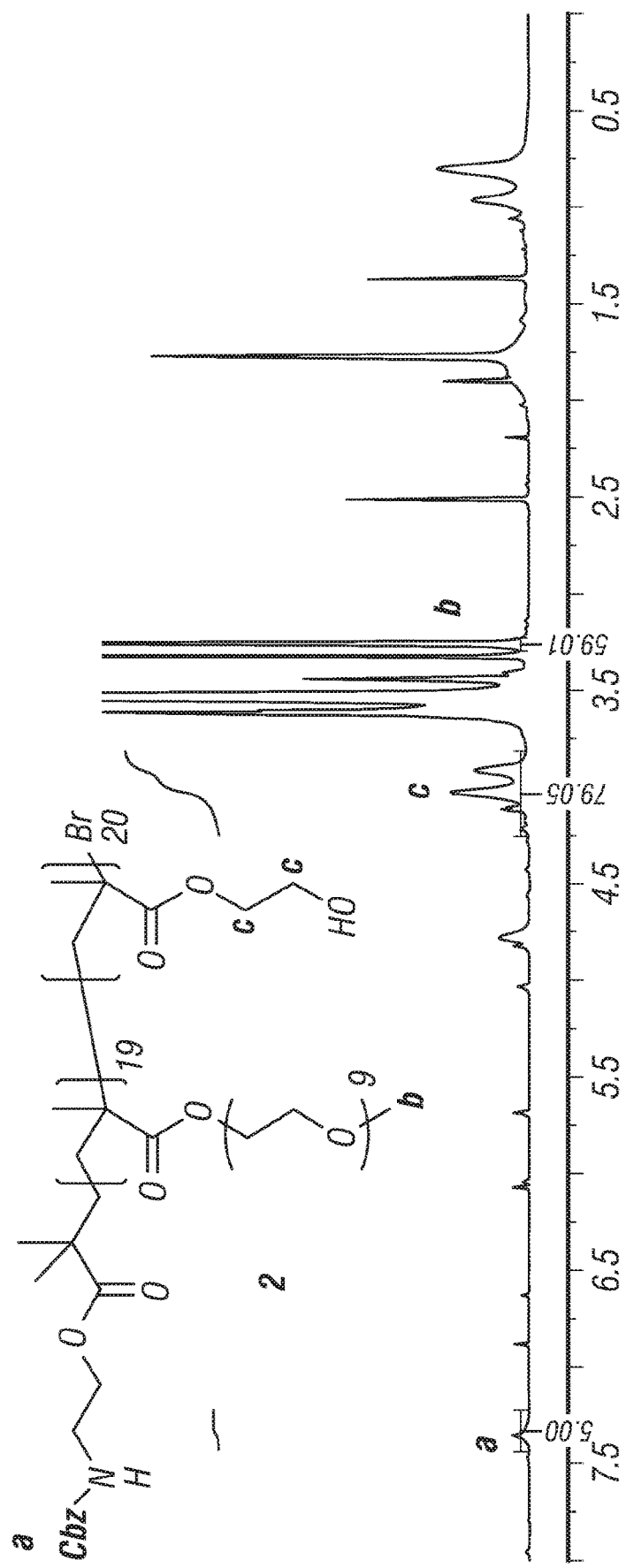
FIG. 10: $^1$H-NMR spectrum of P(PEGMA)$_{19}$-b-P(HEMA)$_{20}$ (polymer 2). Hydrogen atoms and their corresponding peak integrations are marked by lowercase letters.

Poly[oligo(ethylene glycol) monomethyl ether methacrylate)$_{19}$-b-poly(2-hydroxyethyl methacrylate)$_{20}$ (polymer 2). Into a round-bottom flask was added the initiator 1 (24.2 mg, 70.2 µmol), oligo ethylene glycol methyl methacrylate (PEGMA, MW ~50, 1.0 g, 2.1 mmol), 2,2'-bipyridyl (21.9 mg, 140.4 µmol), and 0.5 mL of anhydrous methanol. The flask was flushed with anhydrous argon for 20 min and immersed in a 50° C. oil bath. CuBr (10.0 mg, 70.2 µmol) was quickly added under argon protection, and the reaction was allowed to proceed for 30 min. A separate mixture of 2-hydroxyethyl methacrylate (0.25 mL, 2.1 mmol) in 0.5 mL of methanol was de-oxygenized and added into the reaction mixture. The polymerization was allowed to continue for 18 hr at 50° C. and then stopped by exposure to open air. The reaction mixture was diluted with tetrahydrofuran, passed through a basic aluminum column to remove the catalyst, and condensed in vacuo at 50° C. to give block copolymer 2 as viscous oil 1.2 g (94%). $^1$H-NMR showed that polymer 2 contained 19 units of PEGMA and 20 units of 2-hydroxyethyl methacrylate (HEMA) (FIG. 10). Polymer 2 was abbreviated as P(PEGMA)$_{19}$-b-P(HEMA)$_{20}$.

Figure 11:
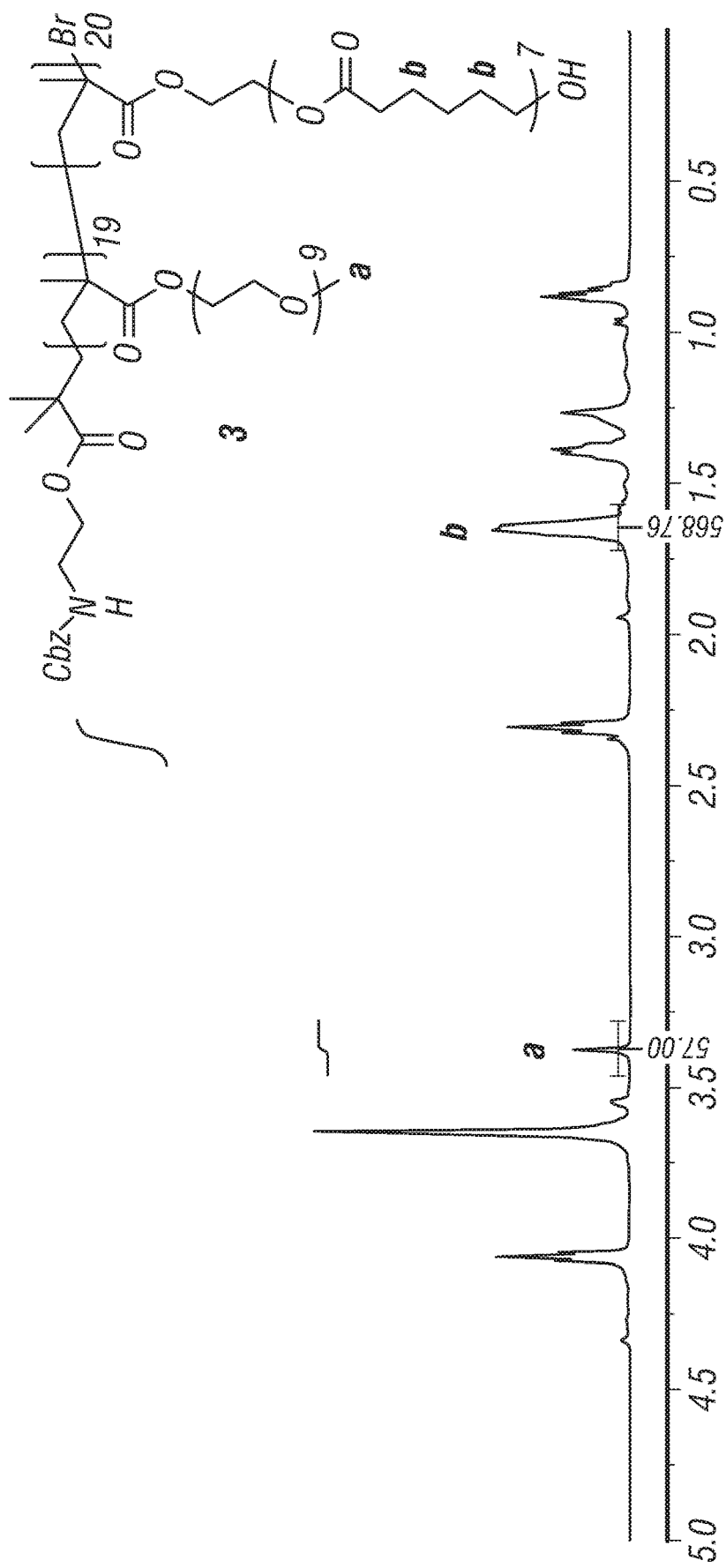
FIG. 11: $^1$H-NMR spectrum of poly(PEGMA)$_{19}$-b-poly[HEMA-g-(ε-caprolactone)$_7$]$_{20}$ (polymer 3). Hydrogen atoms and their corresponding peak integrations are marked by lowercase letters.

Poly(PEGMA)$_{19}$-b-poly[HEMA-g-(ε-caprolactone)$_7$]$_{20}$ (polymer 3). Polymer 2 (2.0 g, 2.8 mmol —OH) was dried by azeotropical distillation with toluene at 110° C. Excess toluene was removed under vacuo. Compound 2 was then dissolved in 4 mL of anhydrous toluene and transferred into a flame-dried flask. Anhydrous ε-caprolactone (CL, 1.6 mL, 14.1 mmol) and tin(II) 2-ethylhexanoate (Sn(Oct)$_2$, 9 µL, 28.1 µmol) were added. The flask was flushed with anhydrous argon and heated at 110° C. overnight. The polymerization mixture was precipitated in hexane twice to give 3.1 g (yield=85%) of the block copolymer 3 as white wax. $^1$H-NMR showed that each oligo(ε-caprolactone) side chain polymer 2 contained 7 units of ε-caprolactone (FIG. 11). Polymer 3 was abbreviated as P(PEGMA)$_{19}$-b-P(HEMA-CL$_7$)$_{20}$.

Figure 12:
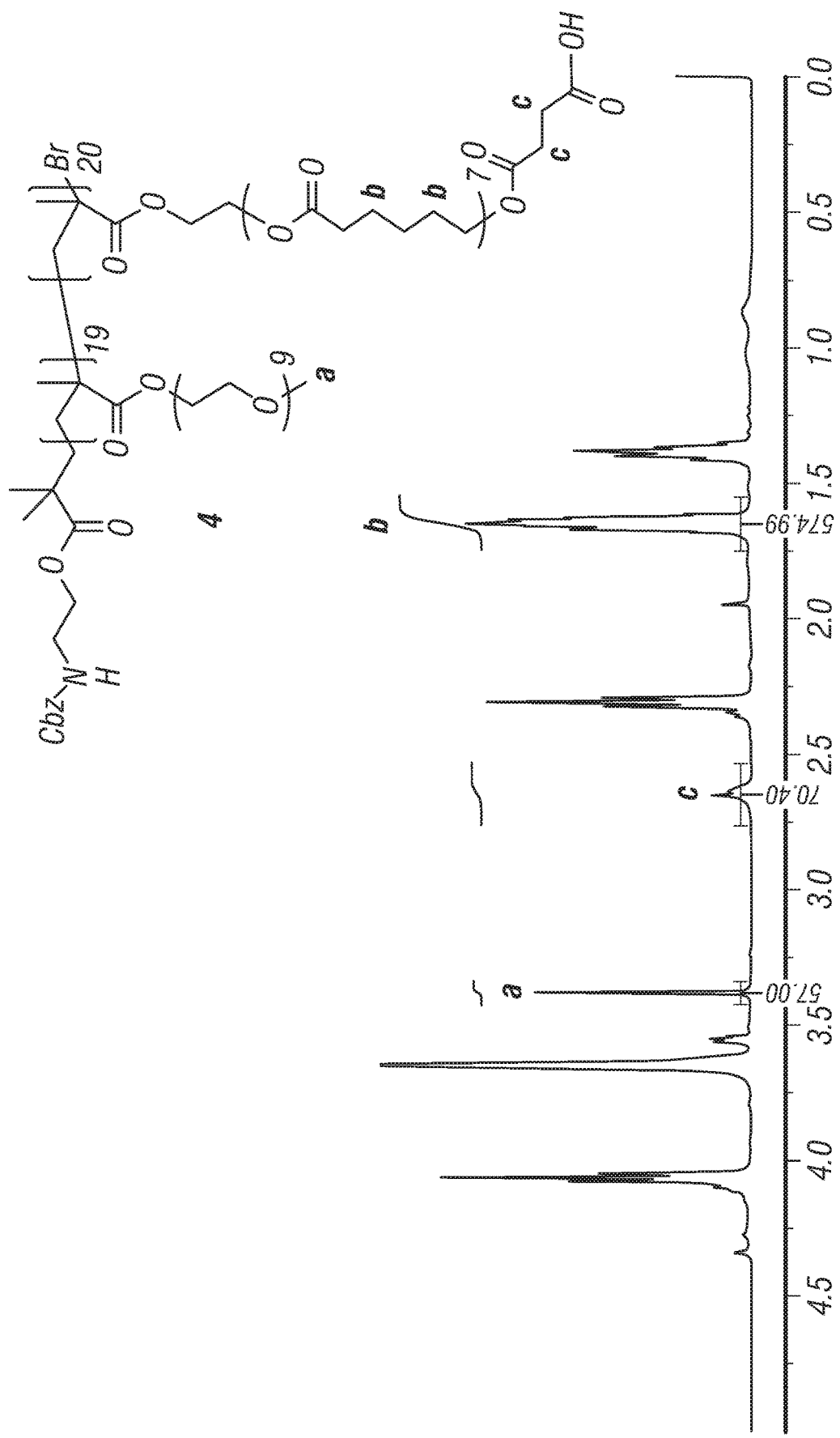
FIG. 12: $^1$H-NMR spectrum of poly(PEGMA)$_{19}$-poly[HEMA-g-(ε-caprolactone)$_7$-mono-succinate ester)]$_{20}$ (polymer 4). Hydrogen atoms and their corresponding peak integrations are marked by lowercase letters.
Figure 13:
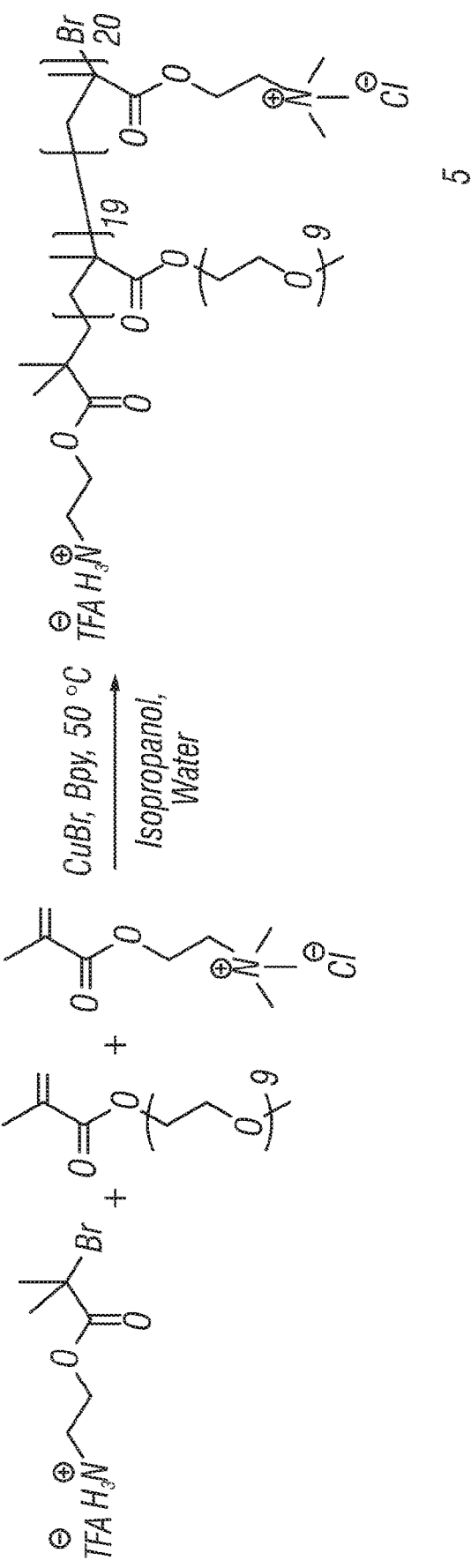
FIG. 13: Schematic illustration for the preparation of cationic polymer poly(PEGMA)$_{19}$-poly(MeDMA)$_{20}$ (polymer 5).

Poly(PEGMA)$_{19}$-poly[HEMA-g-(CL$_7$)-mono-succinate ester)]$_{20}$ (polymer 4). Polymer 3 (1.0 g, 0.78 mmol —OH) was dissolved in 5 mL of anhydrous toluene. Then 3-isocyanatopropyl triethoxysilane (0.2 mL, 0.78 mmol) and dibutyltin dilaurate (5 µL, 7.8 µmol) were added. The flask was heated at 40° C. overnight under argon protection. The reaction mixture was precipitated in diethyl ether/hexane and dried in vacuo at room temperature to give the anionic polymer 4, abbreviated as P(PEGMA)$_{19}$-b-P(HEMA-CL$_7$-SAn)$_{20}$. $^1$H-NMR showed that each polymer contained about 20 units of succinates (FIG. 12).

Figure 14:
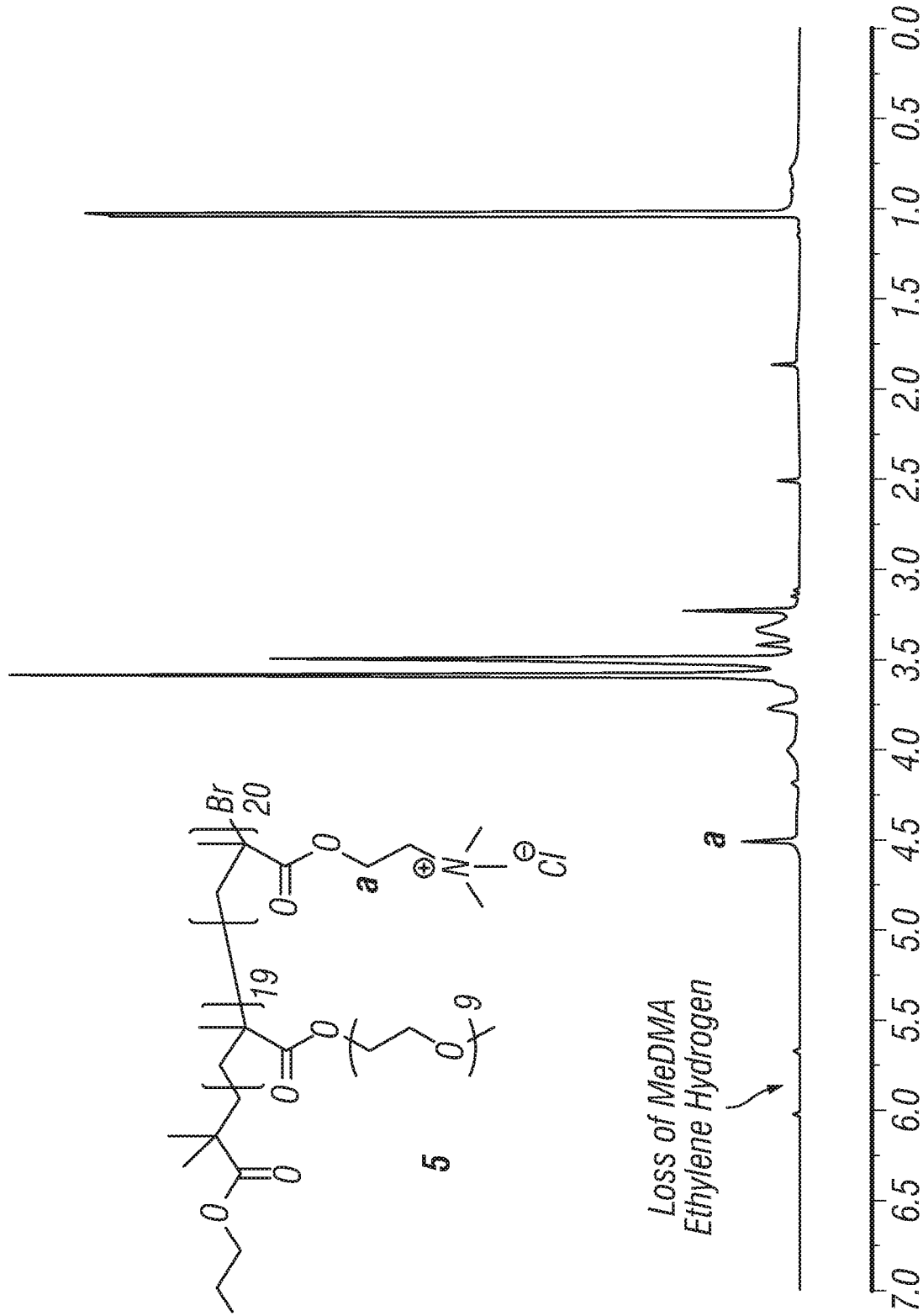
FIG. 14: $^1$H-NMR spectrum of the reaction mixture of cationic polymer poly(PEGMA)$_{19}$-poly(MeDMA)$_{20}$ (polymer 5) at the end of the reaction.

Preparation of Cationic Polymer Poly(PEGMA)$_{19}$-poly (MeDMA)$_{20}$. The initiator, trifluoroacetic acid salt of 2-aminoethyl 2-bromoisobutyrate, was synthesized via published protocol (Tempero et al., 2011). Briefly, to a 50-mL flask were added the initiator (22.7 mg, 70.2 µmol), 2,2'-Bipyridyl (21.9 mg, 140.4 µmol), methoxy-PEG-methacrylate (PEGMA, MW 500) (1.00 g, 2.10 mmol) and 0.5 mL of anhydrous isopropanol. The flask was deoxygenized via three cycles of freeze-pump-thaw and refilled with $N_2$, after which CuBr (10.0 mg, 70.2 µmol) was quickly added. Polymerization was started by heating the flask in an oil bath at 50° C. Thirty minutes later, a pre-deoxygenized solution of 2-(methacryloyloxy) ethyl trimethyl ammonium chloride (MeDMA) (1.77 g, 4.21 mmol) at 40% by weight in water was quickly added into the reaction mixture. The polymerization was allowed to continue for 2 hr at 50° C. $^1$H-NMR showed conversion >98% (FIG. 14). The reaction mixture was dialyzed against deionized water for 3 days to remove un-reacted monomers and catalysts. A solid powder was obtained after lyophilization.

Example 3—Synthesis and Characterization of Polyion Polymers and Drug-Loaded Micelles The chemical structures of the anionic and cationic polymers are shown in FIG. 1. The anionic polymer (FIG. 1A) consisted of a hydrophilic brush-like polyethylene glycol (PEG) block and a hydrophobic block with biodegradable oligo(ε-caprolactone) side chains. Succinates were conjugated to the termini of the caprolactone side chains. The $^1$H-NMR spectrum of the anionic polymer was as follows (FIG. 1B): 1.6 ppm (β and δ —CH$_2$— of the caprolactone units), 2.6 ppm (—CH$_2$— of succinates), and 3.4 ppm (terminal —OCH$_3$ of PEG brushes). Integration of $^1$H-NMR spectra (FIGS. 9-12) indicated that each anionic macromolecule had 19 PEG brushes and 20 caprolactone side chains; each side chain in the hydrophobic block contained seven caprolactone monomers and one succinate terminal group. The cationic polymer (FIG. 1C) consisted of a hydrophilic brush-like PEG block and a cationic block of poly(2-[(methacryloyloxy) ethyl] trimethylammonium chloride).

Figure 2A:
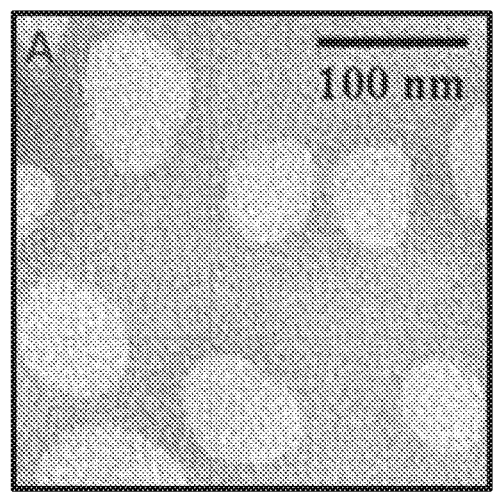
FIGS. 2A-2G: TEM micrographs of polymeric micelles M-CPA (A), M-PTX (B), and M-CPA/PTX (C); and drug-release profiles at 37° C. (D-G) of drug-loaded micelles. TEM was done with uranyl acetate negative staining. Each release study was repeated three times. Data are presented as mean±SD.
Figure 2B:
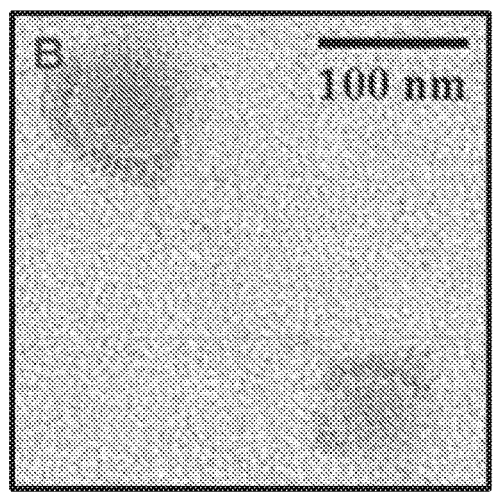
Figure 2C:
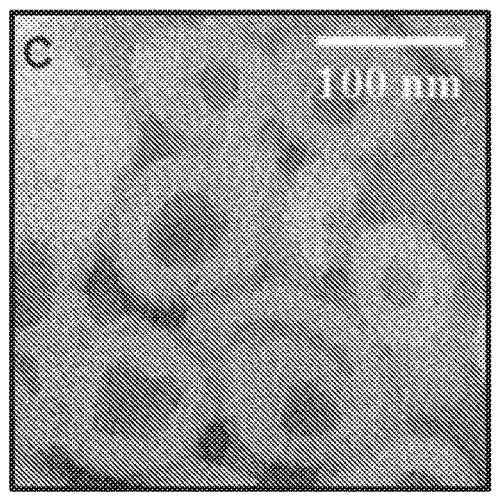
Figure 2D:
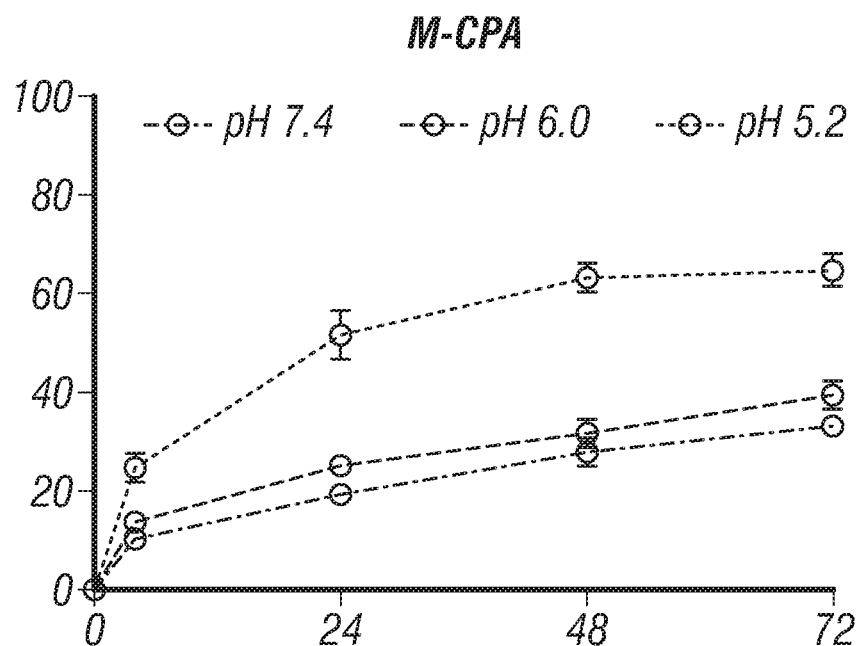
Figure 2E:
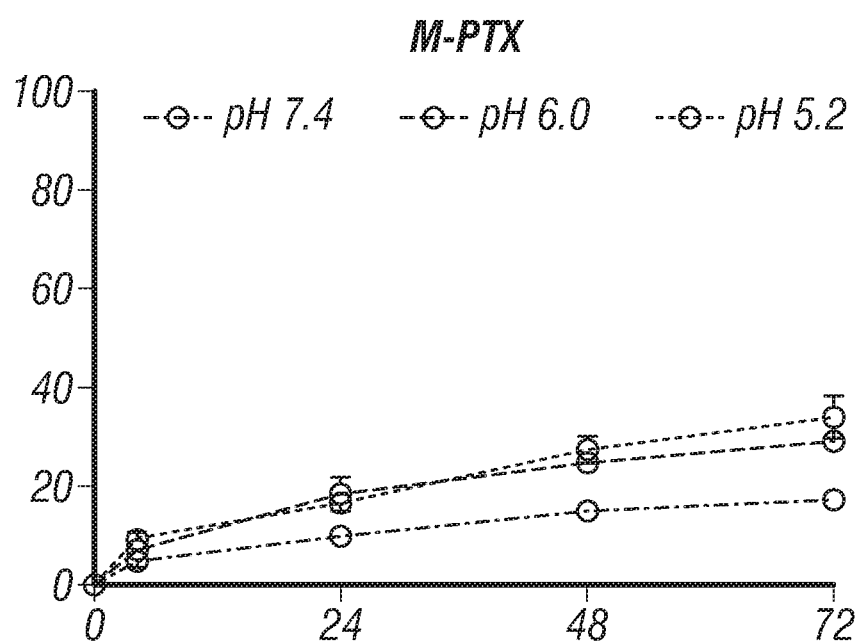
Figure 2F:
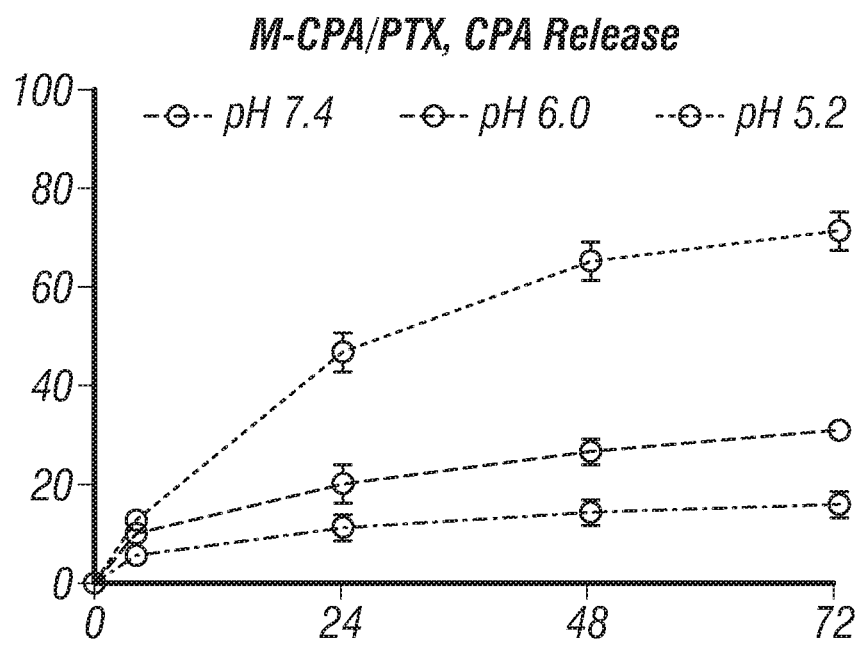
Figure 2G:
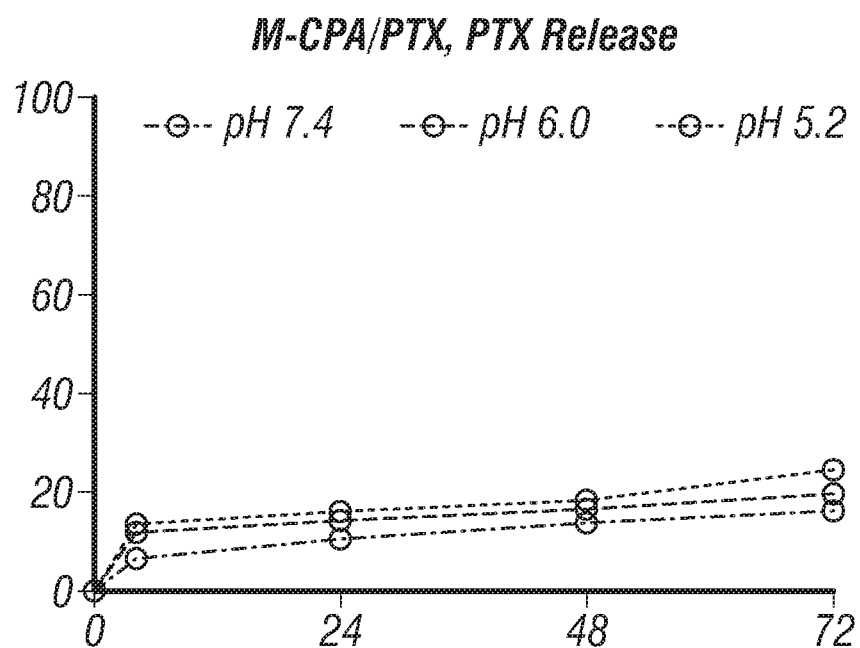

The $^1$H-NMR spectrum of the cationic polymer was as follows (FIG. 1D): 3.3 ppm (terminal —$OCH_3$ of PEG brushes) and 3.5 ppm ($N^+$—$CH_3$ of ammonium). Each polymer had approximately 19 PEG brushes and 20 units of 2-[(methacryloyloxy) ethyl] trimethylammonium chloride. The complete polymerization schemes and $^1$H-NMR spectra are presented in FIGS. 8-14. As shown in Table 1, all of the drug-loaded micelles had size in the range of 60-125 nm, had slightly negative surface charges, and had drug-loading efficiency above 95%. Representative TEM micrographs of each type of micelle are shown in FIGS. 2A-C. The dark color at the micellar core in M-PTX and M-CPA/PTX (FIG. 2C) may arise from the uranyl ions chelated by the carboxylates of anionic polymers. The drug release (FIGS. 2D-G) profiles showed that at pH 7.4, micelles retained more than 80% of the encapsulated CPA or PTX for up to 3 days. As the pH value of incubating buffer decreased, the release of both CPA and PTX increased in all three formulations. When drug-loaded micelles were stored for 90 days at −80° C., no changes were noted between day 0 and day 90 in micelle size or drug loading (Table 2).

TABLE 1

Physicochemical characterization of drug-loaded micelles.

| Characteristic | M-CPA[1] | M-PTX[2] | M-CPA/PTX[3] |
|---|---|---|---|
| Size, nm[4] | 74.7 ± 1.5 | 121.6 ± 2.1 | 61.5 ± 1.9 |
| PDI | 0.148 | 0.124 | 0.131 |
| Zeta-potential, mV | −13.5 ± 10.1 | −6.9 ± 3.5 | −9.7 ± 4.1 |
| Drug loading efficiency | >95% | >95% | >95% |

PDI, polydispersity index.

[1]CPA/anionic polymer = 5% by weight.

[2]PTX/anionic polymer = 5% by weight.

[3]CPA/anionic polymer = 2.5% by weight; PTX/anionic polymer = 2.5% by weight.

[4]Number-average size. Anionic polymer/cationic polymer = 5/1 by weight in all specimens.

TABLE 2

Long-term Stability of Drug-loaded Polymeric Micelles[1] at −80° C.

| Micelle Type and Characteristic | Day 0 | Day 90 |
|---|---|---|
| M-CPA[2] | | |
| Size, nm[5] | 74.7 ± 1.5 | 70.6 ± 2.7 |
| PDI | 0.148 | 0.184 |
| Relative CPA loading, % | 100 ± 4.3 | 98.5 ± 1.4 |
| M-PTX[3] | | |
| Size, nm[5] | 121.6 ± 2.1 | 94.9 ± 1.3 |
| PDI | 0.111 | 0.173 |
| Relative PTX loading, % | 100 ± 1.8 | 101.8 ± 3.5 |
| M-CPA/PTX[4] | | |
| Size, nm[5] | 61.5 ± 1.9 | 53.2 ± 3.2 |
| PDI | 0.131 | 0.181 |
| Relative CPA loading, % | 100 ± 3.1 | 99.4 ± 1.7 |
| Relative PTX loading, % | 100 ± 2.6 | 100.5 ± 3.5 |

PDI, polydispersity index.

[1]Micelles were snap-frozen in the presence of 5% sucrose.

[2]CPA/anionic polymer = 5% by weight.

[3]PTX/anionic polymer = 5% by weight.

[4]CPA/anionic polymer = 2.5% by weight; PTX/anionic polymer = 2.5% by weight.

[5]Number-average size. Anionic polymer/cationic polymer = 5/1 by weight in all specimens.

Figure 3A:
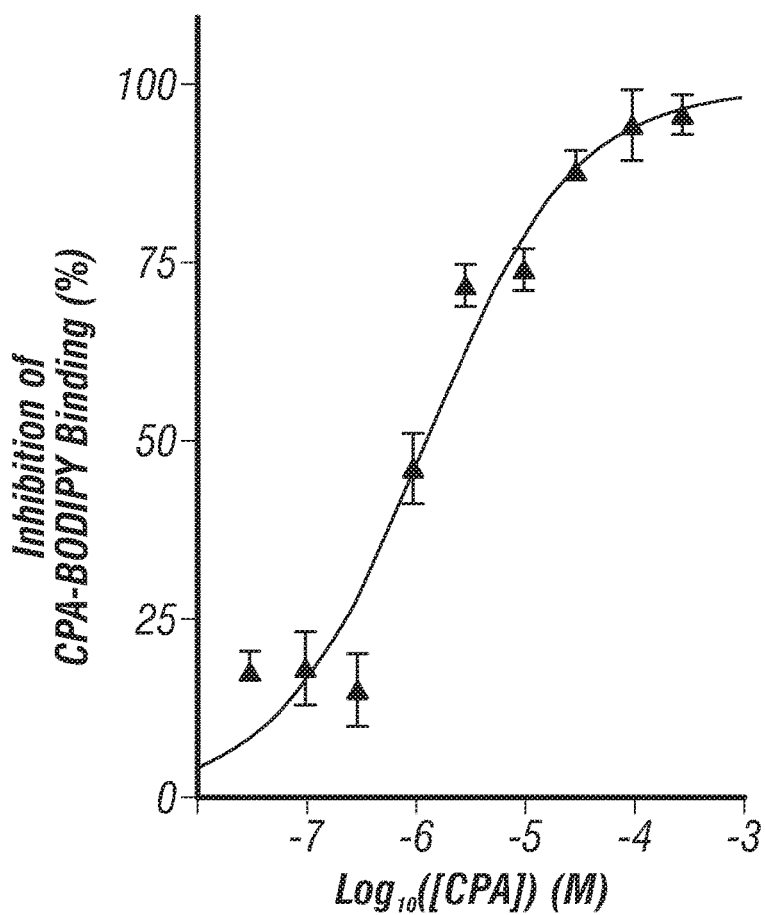
FIGS. 3A-3I: Effects of M-CPA and M-PTX on Miapaca-2 cells. (A) Inhibition of CPA-BODIPY binding to SMO receptors after 24-h incubation with M-CPA. (B and C) Representative fluorescence microscopic images of CPA-BODIPY-treated cells (B) not incubated with M-CPA and (C) incubated with 20 μM M-CPA. Green, CPA-BODIPY; blue, nuclei; scale bar=20 μm. (D) Normalized Gli-1 expression after 48-h incubation with M-CPA. (E and F) Cell viability after 72-h incubation with (E) CPA or M-CPA or (F) PTX, M-PTX, or M-CPA/PTX. (G) Normalized number of colonies formed after 10-day incubation with CPA or M-CPA. (H and I) Representative images of colonies after incubation with (H) 3 μM CPA or (I) 3 μM M-CPA.
Figure 3B:
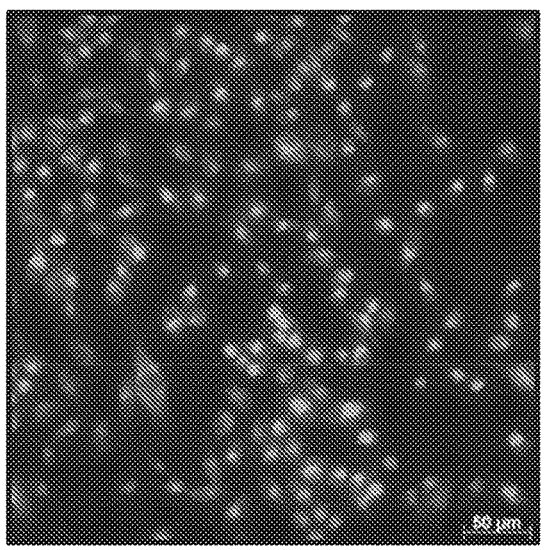
Figure 3C:
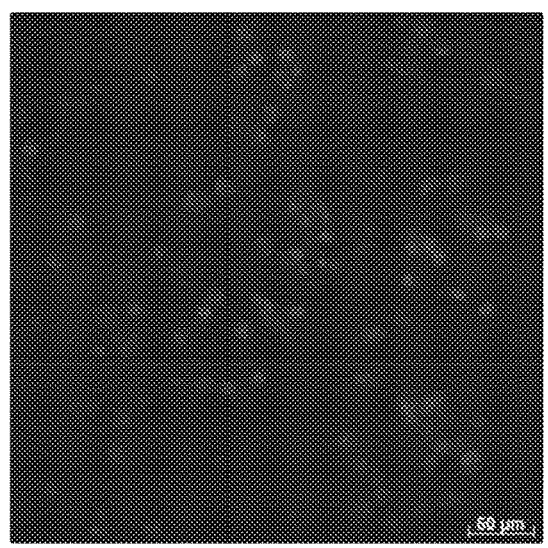

Example 4—Effects of Drug-Loaded Micelles on SHH Pathway Signaling Molecules, Proliferation, and Stem Cell Population in Pancreatic Cancer Cell Lines CPA inhibits SHH activity by binding to SMO. FIG. 3A shows that M-CPA could compete with CPA-BODIPY, a fluorescent ligand for SMO. Pretreatment of Miapaca-2 cells with 1.3±0.3 μM M-CPA resulted in 50% loss of CPA-BODIPY binding ($EC_{50}$=1.3±0.3 μM). The $EC_{50}$ values of M-CPA in L3.6pl and Panc-1 cells were 0.9±0.2 and 0.35±0.05 μM, respectively (Table 3). Fluorescence micrographs confirmed that the fluorescence of CPA-BODIPY-treated cells was strong in the absence of M-CPA (green, FIG. 3B) but diminished in the presence of 20 μM M-CPA (FIG. 3C).

TABLE 3

Effects of M-CPA on SMO Receptor Binding and Cell Proliferation.

| | Miapaca-2 | L3.6 pl | Panc-1 |
|---|---|---|---|
| $EC_{50}$ for inhibition of SMO binding | | | |
| M-CPA, μM | 1.3 ± 0.3 | 0.9 ± 0.2 | 0.35 ± 0.05 |
| $IC_{50}$ for cell proliferation | | | |
| CPA, μM | 10.2 ± 0.1 | 16.0 ± 1.5 | ~163 |
| M-CPA, μM | 7.3 ± 1.4 | 6.2 ± 0.6 | ~249 |
| PTX, nM | 1.2 ± 0.1 | 1.4 ± 0.1 | 2.4 ± 0.4 |
| M-PTX, nM | 1.3 ± 0.1 | 1.3 ± 0.1 | 1.6 ± 0.2 |
| M-CPA/PTX,[1] nM in PTX equivalent | 0.9 ± 0.1 | 1.1 ± 0.2 | 1.2 ± 0.5 |

[1]CPA and PTX were equally loaded in micelles.

Figure 3D:
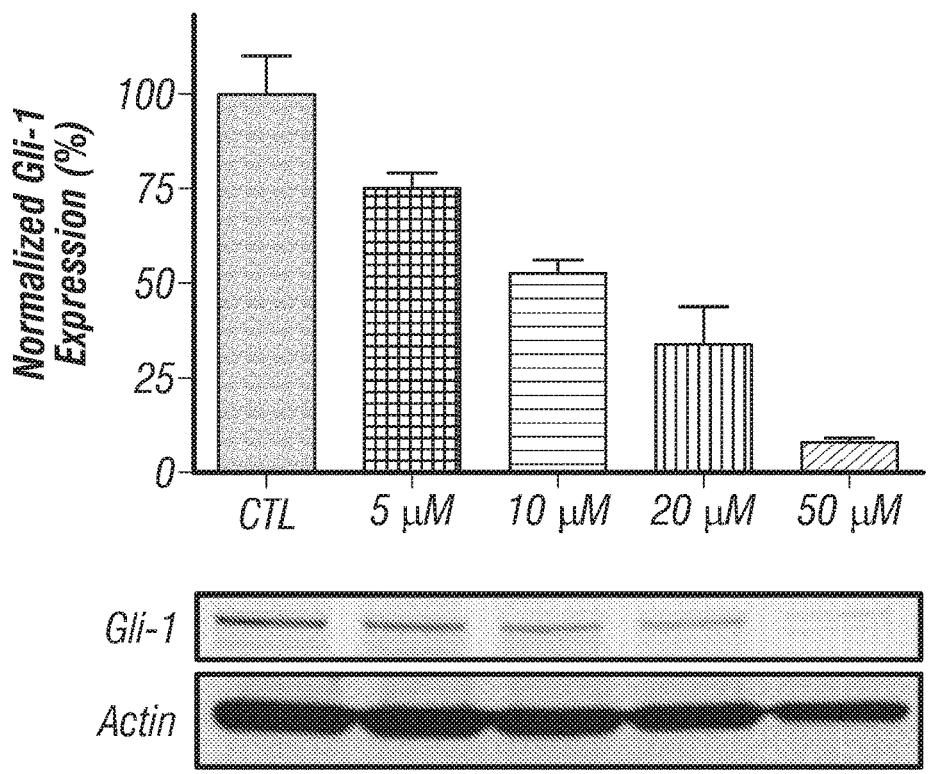
Figure 15:
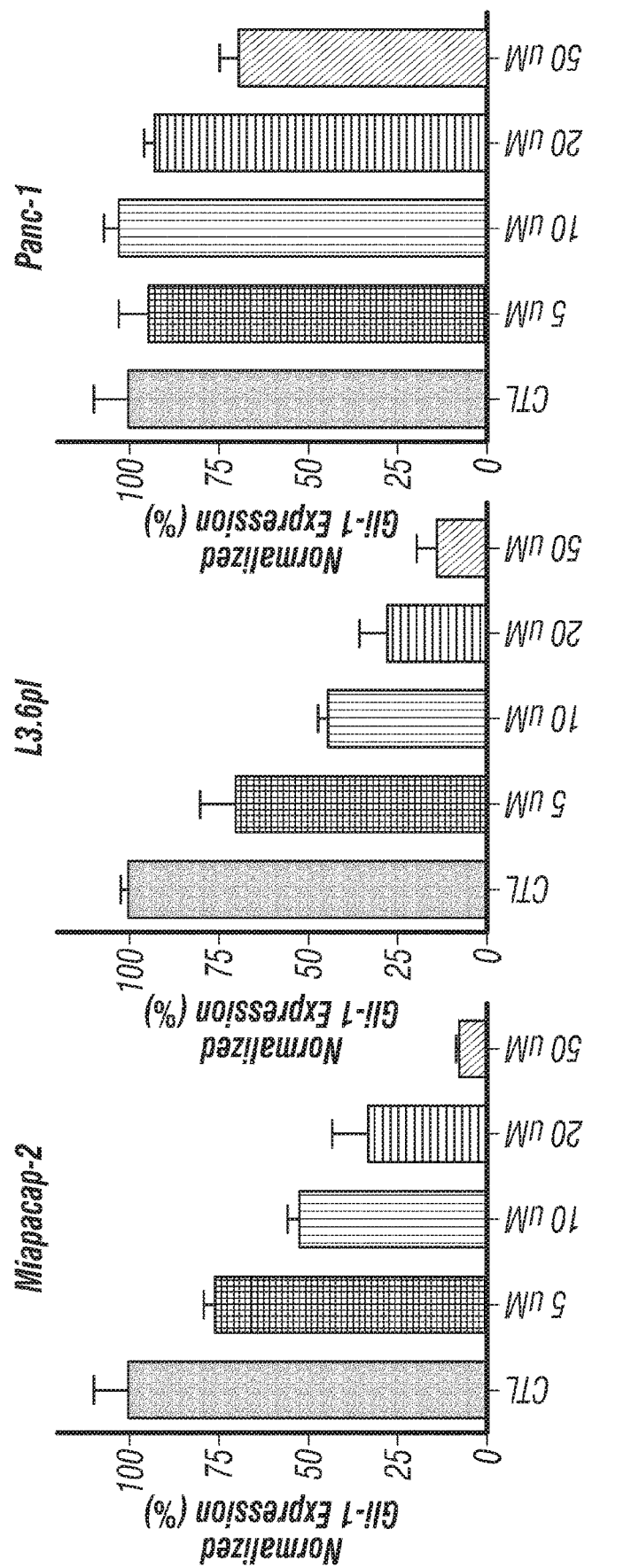
FIG. 15: Relative Gli-1 expression in Miapaca-2, L3.6pl, and Panc-1 cells after 48-hr treatment with M-CPA.

Gli-1 is a downstream target of SMO in the SHH pathway. M-CPA treatment reduced Gli-1 expression in Miapaca-2 cells in a dose-dependent manner (FIG. 3D). Compared to Gli-1 expression with no treatment (control), the relative Gli-1 expression (%) was 75.5±2.5, 52.6±2.2, 33.4±7.0, and 7.3±0.7 after treatment with 5, 10, 20, and 50 μM M-CPA, respectively. Similar M-CPA-induced downregulation of Gli-1 was observed in L3.6pl cells; M-CPA slightly downregulated Gli-1 in Panc-1 cells (FIG. 15).

Figure 3E:
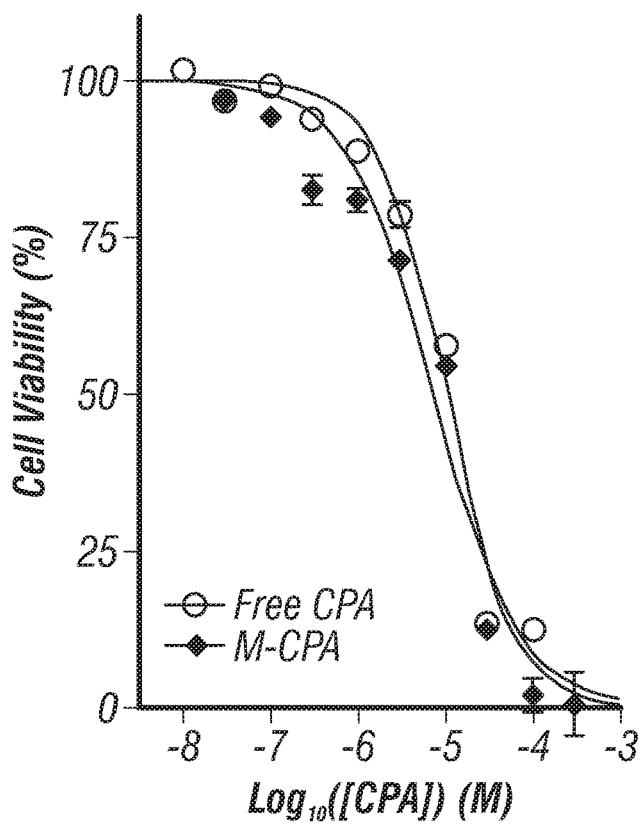
Figure 3F:
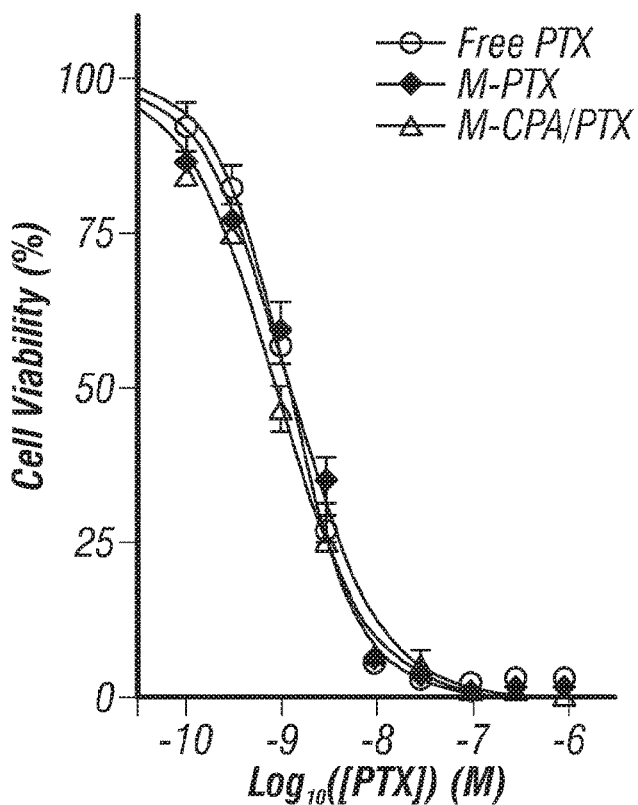
Figure 3G:
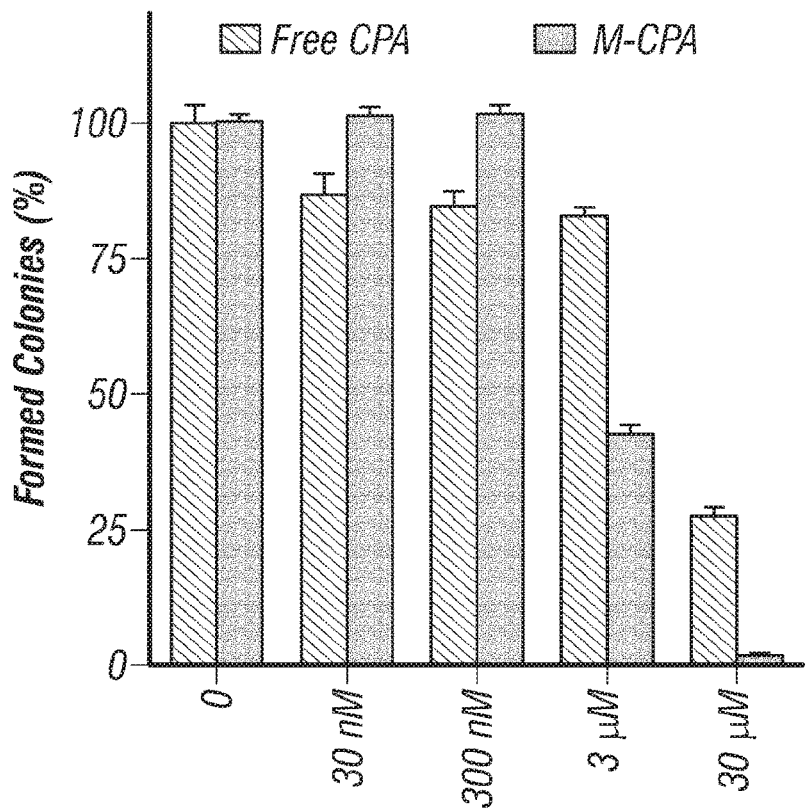
Figure 3H:
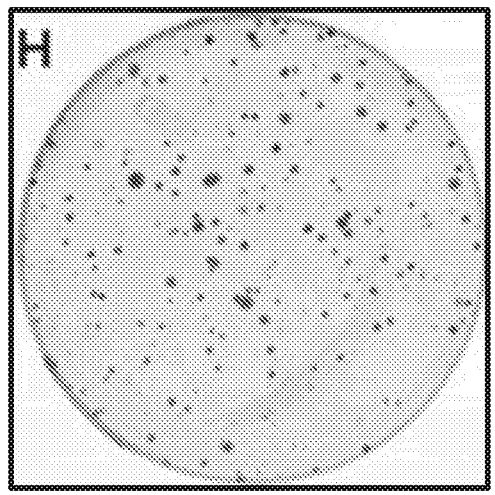
Figure 3I:
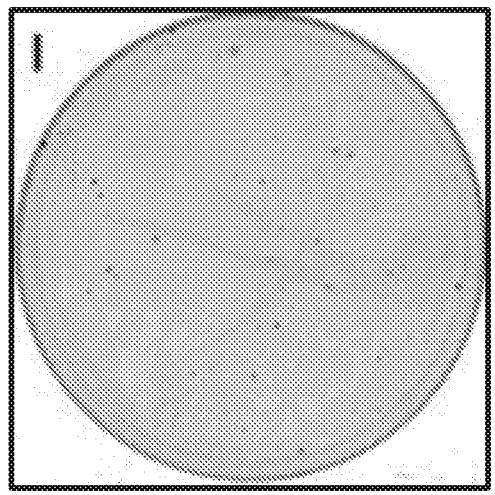
Figure 4A:
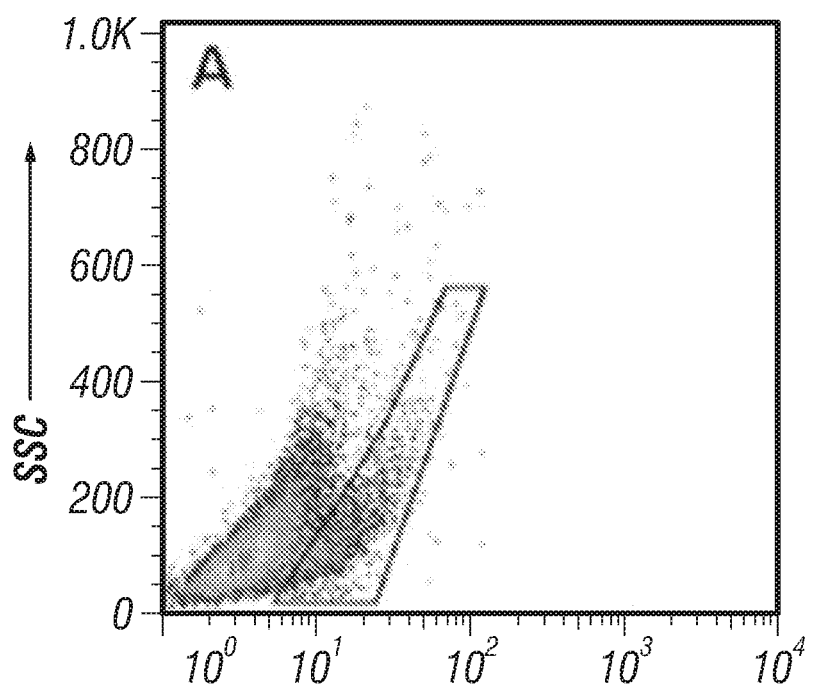
FIGS. 4A-4J: Effect of M-CPA and/or M-PTX treatment of Miapaca-2 cells on CD133 expression and tumorsphere formation. (A-D) Representative flow cytometry plots of CD133 expression after 48-h exposure to (A) CTL, (B) 10 μM M-CPA, (C) 10 nM M-PTX, or (D) 10 μM M-CPA+10 nM M-PTX. CD133$^+$ cells are those within polygons. (E) Percentages of CD133$^+$ cells after the indicated treatments (N=3). M-PTX treatment significantly enriched the CD133$^+$ population compared to control ($p<0.001$); M-CPA and M-CPA/PTX significantly depleted the CD133$^+$ population compared to control ($p<0.001$). (F) Numbers of formed tumorspheres (>50 μm) per 1000 cells after the indicated treatments (N=6). The control and M-PTX groups had significantly more tumorspheres than the M-CPA or M-CPA/PTX group (p<0.001). (G-J) Representative micrographs of cells treated with (G) control (CTL), (H) 10 μM M-CPA, (I) 10 nM M-PTX, or (J) 10 μM M-CPA+10 nM M-PTX.
Figure 4B:
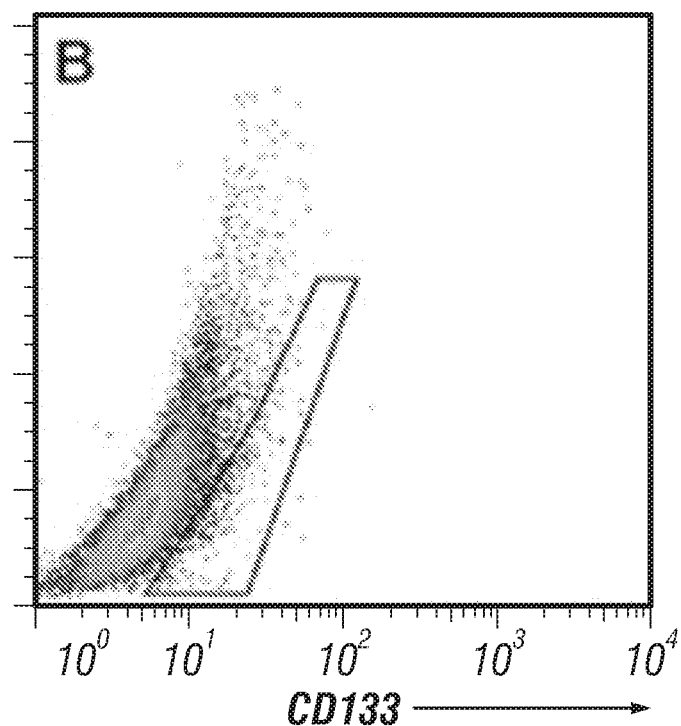
Figure 4C:
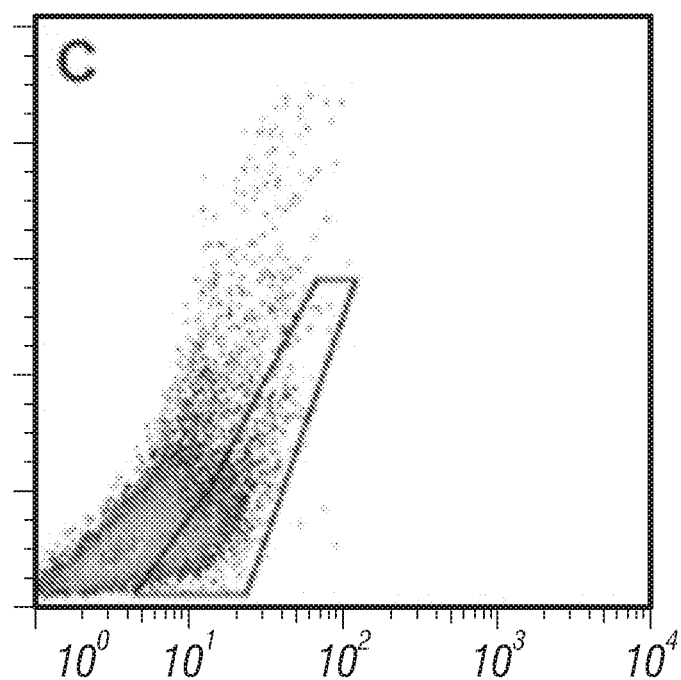
Figure 4D:
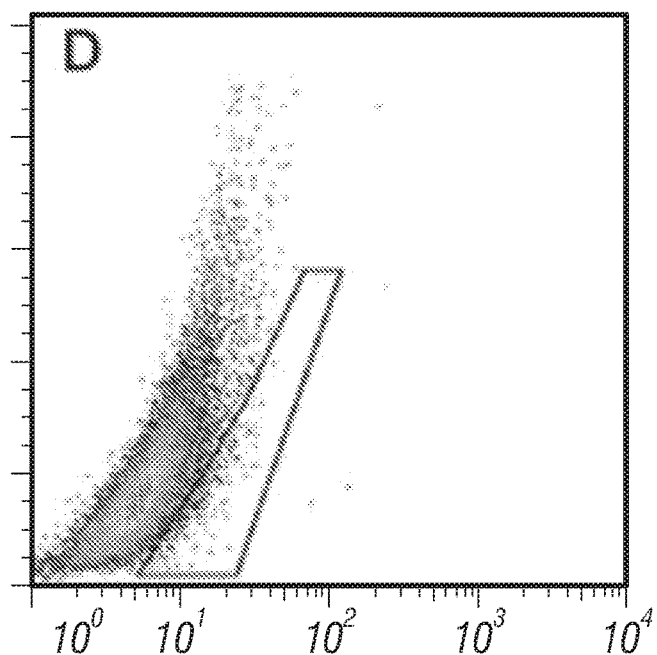
Figure 4E:
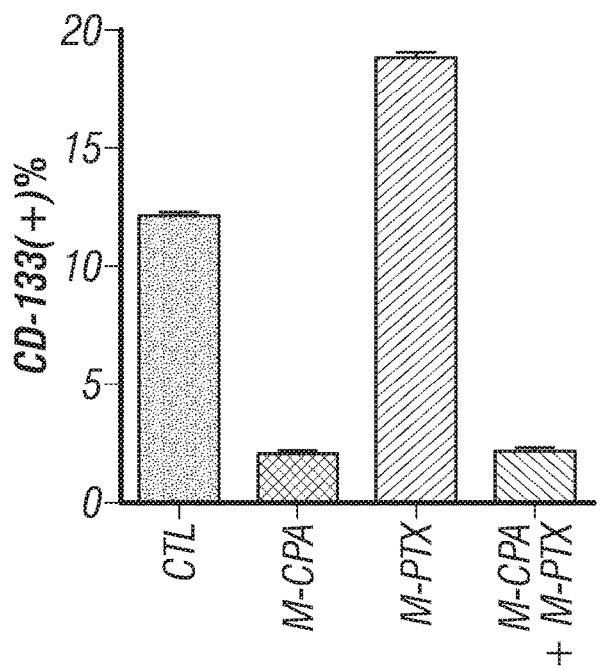
Figure 4F:
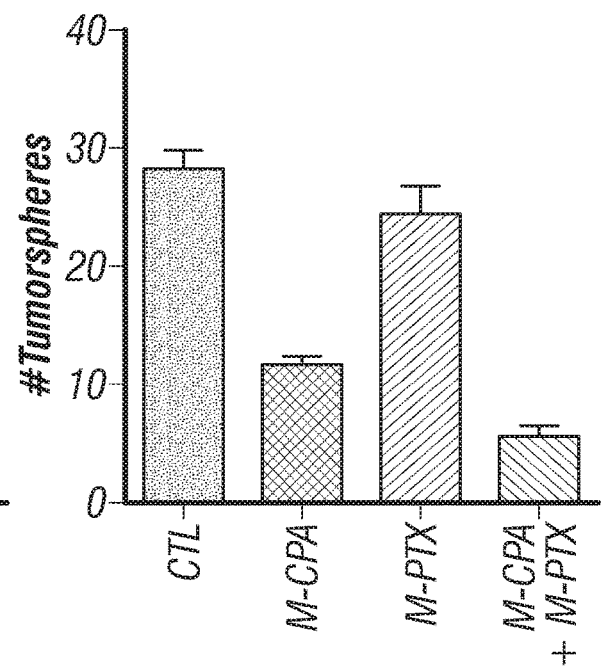
Figure 4G:
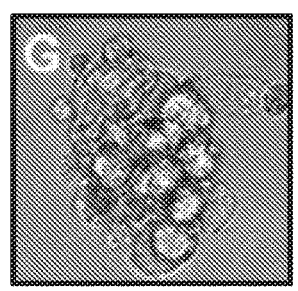
Figure 4I:
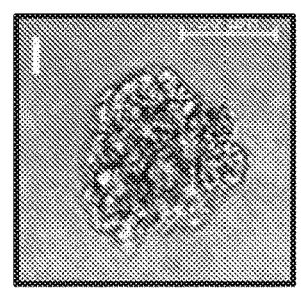
Figure 4H:
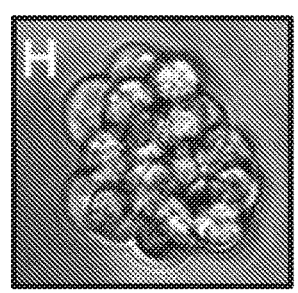
Figure 4J:
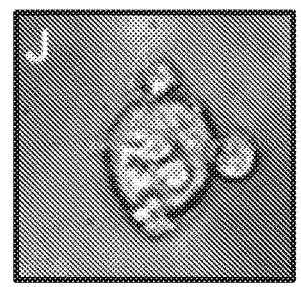
Figure 16A:
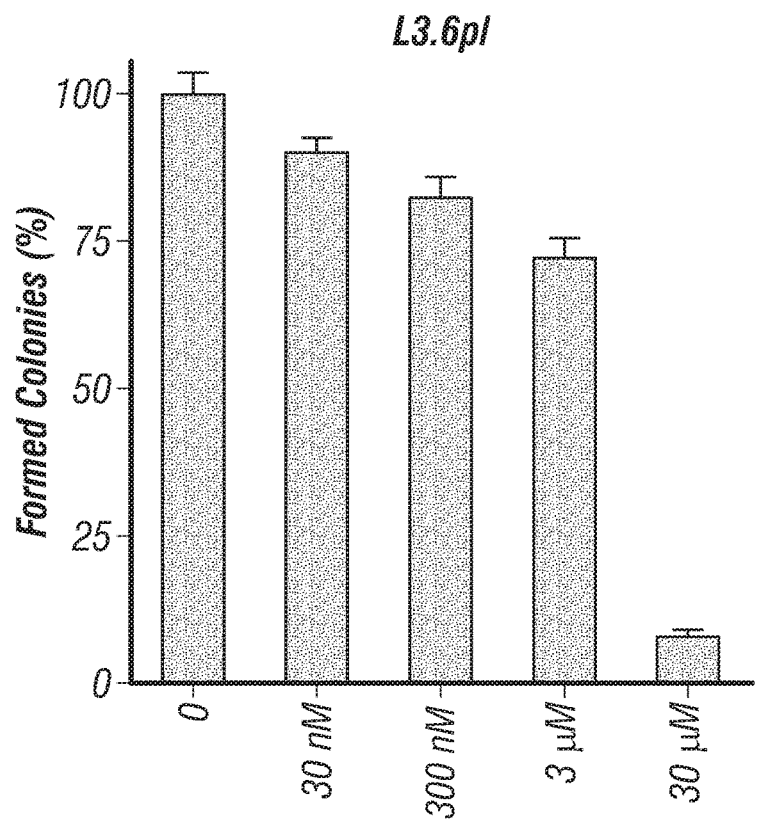
FIGS. 16A-16B: Colony formation of L3.6pl cells (A) and Panc-1 cells (B) during incubation with M-CPA at various concentrations.
Figure 16B:
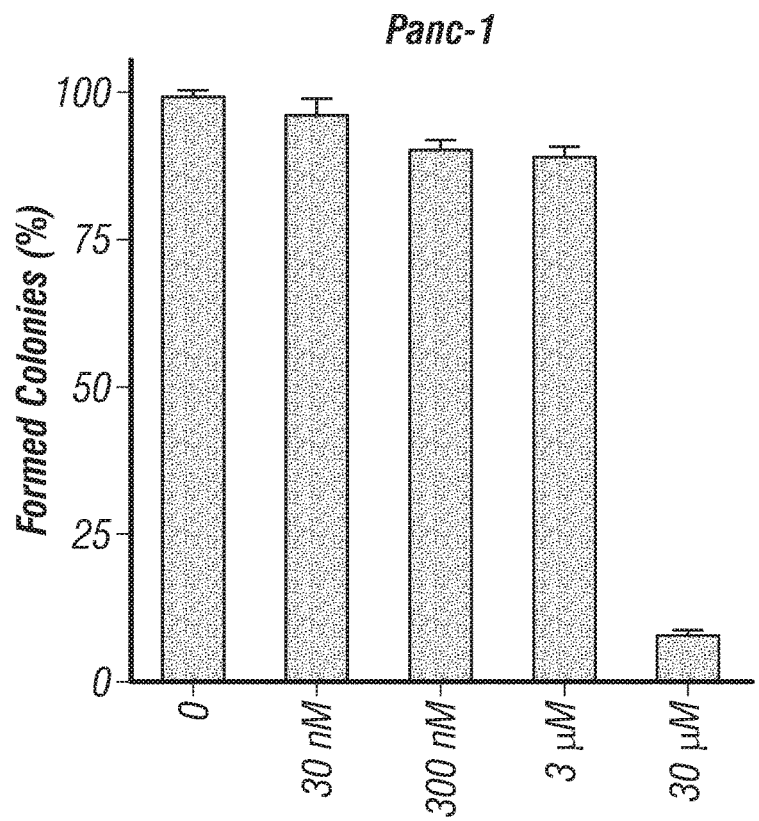
Figure 17A:
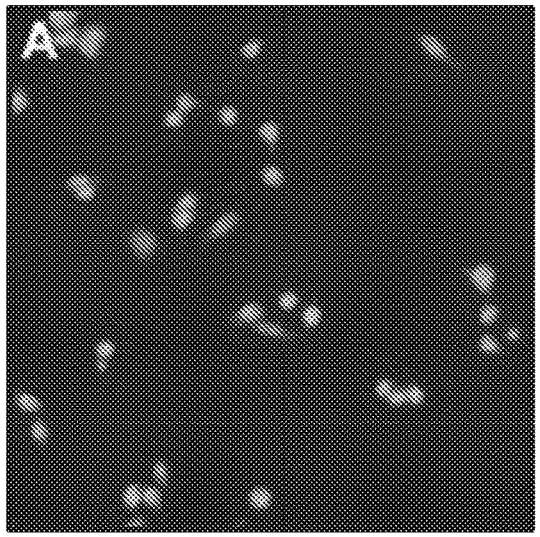
FIGS. 17A-17D: Immunofluorescence staining of SMO (green) in Miapaca-2 cells (A), L3.6pl cells (B), HPSCs (C), and Panc-1 cells (D). Cell nuclei were counterstained with Hoechst (blue).
Figure 17B:
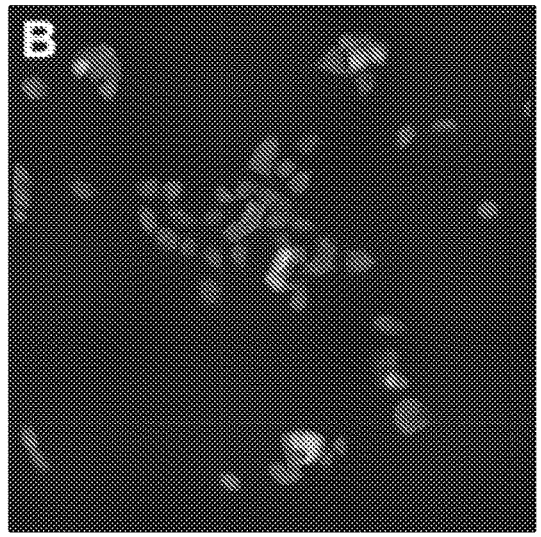
Figure 17C:
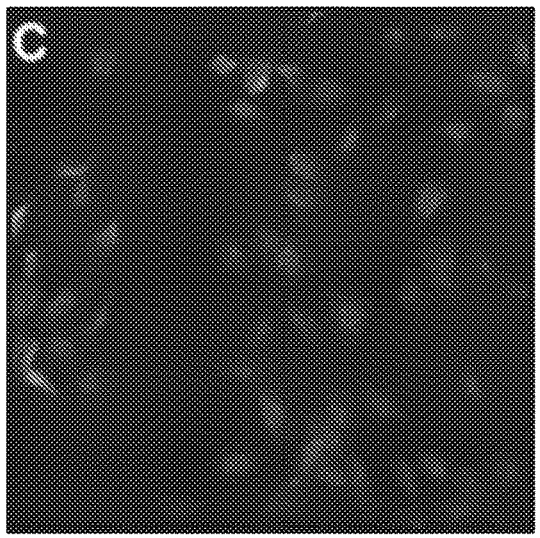
Figure 17D:
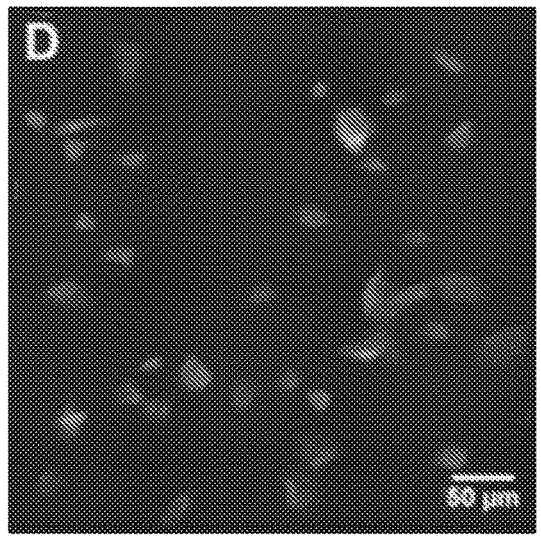

Next, the cell proliferation during drug treatments was assessed. M-CPA was more cytotoxic than CPA in Miapaca-2 (FIG. 3E) and L3.6pl cells (Table 3), but neither treatment was effective against Panc-1 cells (Table 3). Both M-PTX and PTX showed excellent cytotoxicity against all three cell lines (Table 3). When CPA and PTX were equally loaded in micelles, the resultant M-CPA/PTX had slightly higher cytotoxicity against all three cell lines than M-PTX did (FIG. 3F, Table 3). Colony formation assay in Miapaca-2 cells showed that M-CPA inhibited colony formation more effectively than CPA did at higher concentrations (FIGS. 3G-I). Compared to no treatment (control), 3 µM CPA reduced the number of colonies by 18.2±1.3%, and 3 µM M-CPA reduced the number of colonies by 57.7±2.3%. M-CPA also inhibited colony formation against L3.6pl cells and Panc-1 cells at high equivalent drug concentration (30 µM), although only L3.6pl showed dose-dependent response at lower drug concentrations (0-3 µM) (FIG. 16).

CD133 is a surface marker for the CSCs in pancreatic cancer (Simeone, 2008). The impact of treatments on the CD133-positive (CD133+) population of Miapaca-2 cells is summarized in FIGS. 4A-E. The percentage of CD133+ cells was 12.2±0.2 for control, 2.1±0.1 for M-CPA, 18.9±0.2 for M-PTX, and 2.2±0.1 for M-CPA+M-PTX. M-PTX treatment significantly enriched the CD133+ population compared to control ($p<0.001$), whereas both M-CPA and M-CPA/PTX significantly depleted the CD133+ population compared to control ($p<0.001$). There was no significant difference in CD133+ depletion between M-CPA and M-CPA/PTX treatment. M-CPA/PTX also reduced the formation of tumorspheres (FIG. 4F-J). The number of tumorspheres (size >50 µm) per 1000 cells was 28±5 for control, 12±2 for M-CPA, 25±5 for M-PTX, and 6±2 for M-CPA/PTX. The control and M-PTX groups had significantly more tumorspheres than the M-CPA group or M-CPA/PTX group ($p<0.001$). Representative micrographs of tumorspheres are shown in FIG. 4G-J.

Example 5—Effect of M-CPA on HPSCs

Figure 5A:
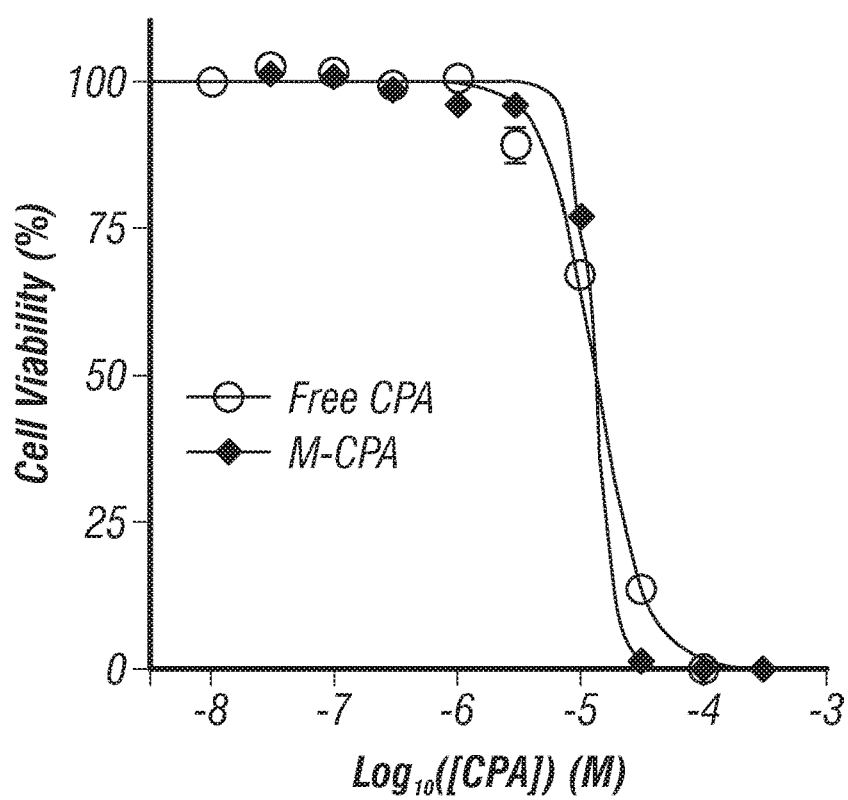
FIGS. 5A-5E: Effects of drug-loaded micelles on HPSC proliferation and SHH pathway activities. (A) Cell viability after 72-h incubation with M-CPA or free CPA (concentration in CPA equivalent) (N=6). (B) Cell viability after 72-h incubation with M-PTX or M-CPA/PTX (concentration in PTX equivalent) (N=6). M-CPA/PTX had equal loading of CPA and PTX. (C) Normalized Gli-1 expression of HPSCs after 48-h incubation with M-CPA. Results are means from two independent western blot analyses and are normalized against β-actin. (D) Cell viability after 72-h incubation in the presence of SHH ligand, with or without 10 μM M-CPA (N=6). (E) Normalized Gli-1 expression of HPSCs after 48-h incubation in the presence of M-CPA, with or without 1.5 μg/mL SHH. Results are means from two independent western blot analyses and are normalized against β-actin.
Figure 5B:
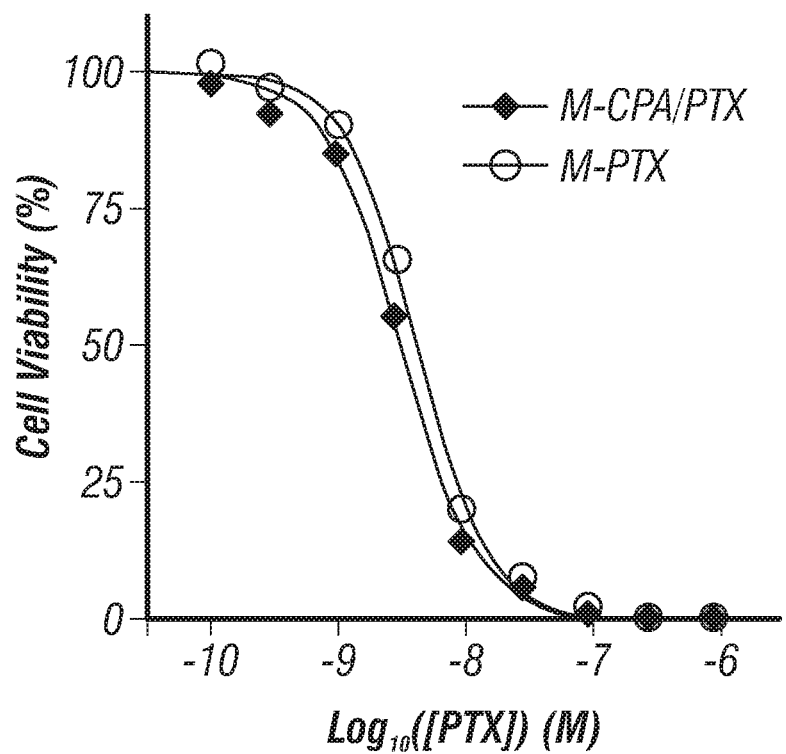
Figure 5C:
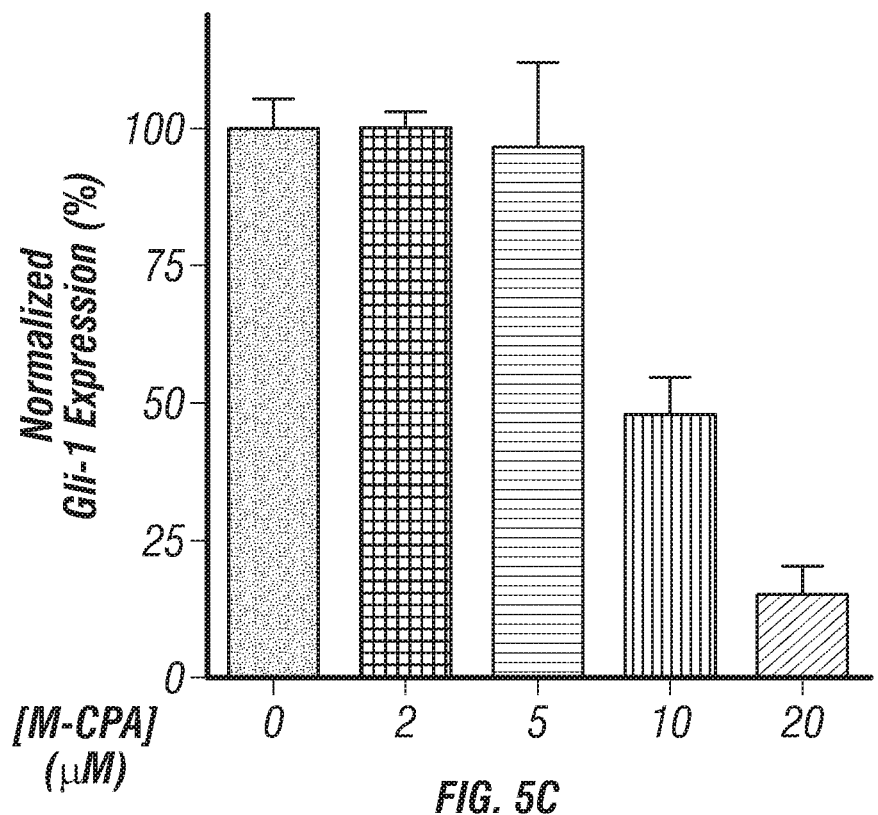

Pancreatic cancer is known for its abundance of stroma tissue, which is produced mostly by activated stellate cells. The efficacy of M-CPA against stroma-producing HPSCs was examined in vitro. FIGS. 5A and 5B show HPSC proliferation during the various treatments. The $IC_{50}$ values were 13.3±1.2 µM for CPA, 12.7±1.1 µM for M-CPA, 4.4±0.2 nM for M-PTX, and 3.3±0.1 nM for M-CPA/PTX (in PTX equivalent). M-CPA reduced Gli-1 expression by HPSCs in a dose-dependent manner: the relative Gli-1 expression (%) was 100.2±2.6, 96.9±10.9, 48.4±4.3, and 15.2±3.6 after treatment with 2, 5, 10, and 20 µM M-CPA, respectively (FIG. 5C). Proliferation of HPSCs can be stimulated by exogenous SHH ligand.

Figure 5D:
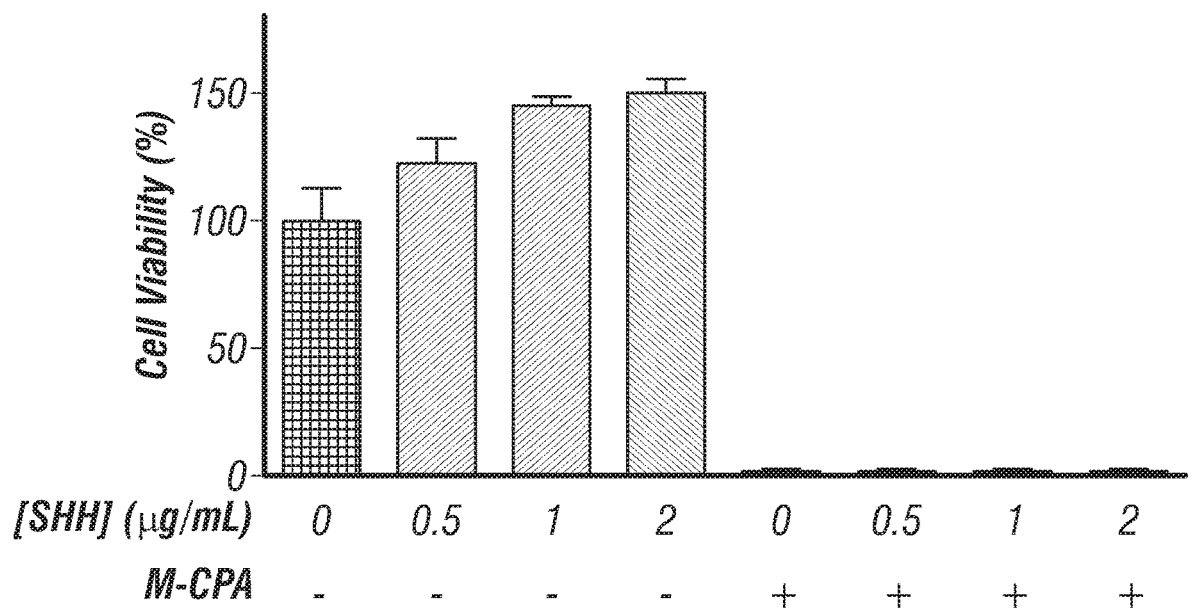
Figure 5E:
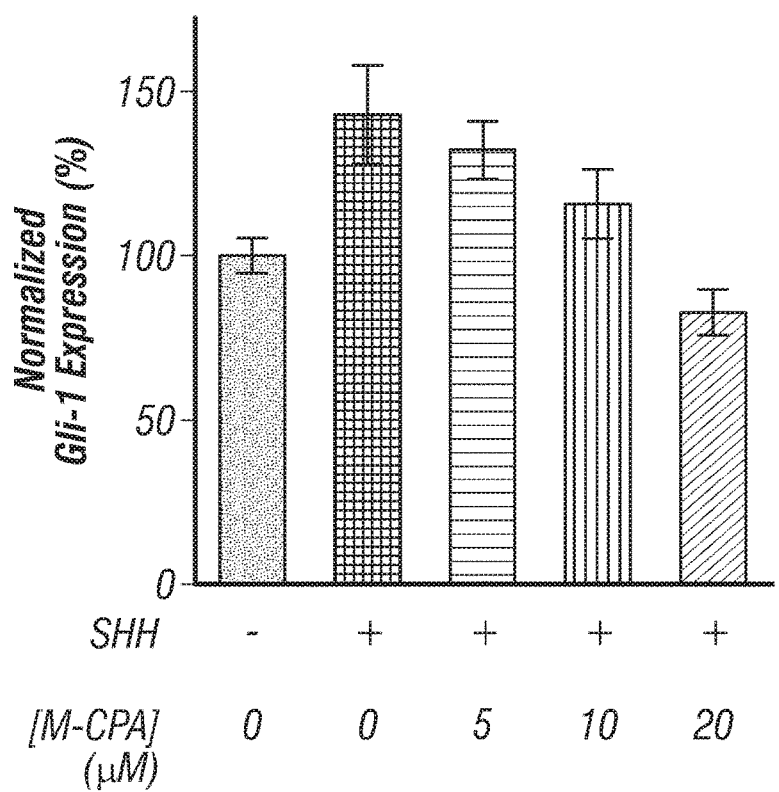

However, in cell culture using serum-free medium 15, M-CPA neutralized stimulation of HPSC proliferation by exogenous SHH ligand (FIG. 5D). In the absence of M-CPA, the relative proportions of viable cells (%) for HPSCs stimulated with 0.5, 1, and 2 µg/mL SHH ligand were 122.2±9.3, 144.5±4.1, and 149.5±4.7, respectively, compared to no treatment (control). In the presence of 10 µM M-CPA, however, no cells were viable after 72-h incubation at any of the SHH concentrations tested. These effects of M-CPA on HPSC viability were accompanied by decreased Gli-1 expression (FIG. 5E). Compared to no treatment (control), 1.5 µg/mL SHH ligand increased Gli-1 expression (%) to 143.7±14.7. M-CPA negated the stimulatory effect of SHH ligand: relative Gli-1 expression (%) in the presence of SHH ligand was 132.6±8.5, 116.3±10.4, and 83.3±6.8 after treatment with 5, 10, and 20 µM M-CPA.

Example 6—Effect of Drug-Loaded Micelles on Tumor Growth in Vivo

Figure 6A:
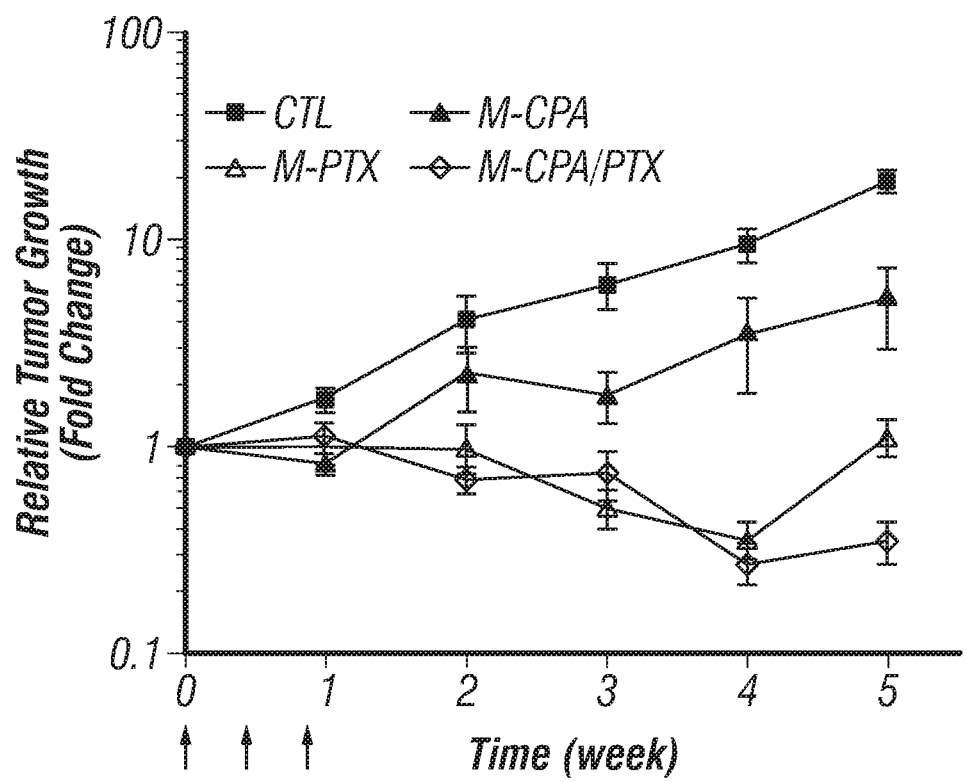
FIGS. 6A-6D: Antitumor efficacy of M-CPA, M-PTX, and M-CPA/PTX in an orthotopic Miapaca-2/HPSC xenograft model in mice. (A) Relative tumor growth measured by bioluminescence (N=9). Dosages were as follows: M-CPA and M-PTX, 10 mg/kg/injection, 3 injections in 1 week; M-CPA/PTX, 10 mg/kg/drug/injection, 3 injections in 1 week. Time of injections is marked with arrows. Tumor growth was slower in the M-CPA/PTX group than in any other group (p<0.01). (B and C) Representative micrographs of hematoxylin-eosin-stained tumor sections from control and M-CPA/PTA-treated mice. (B) Tumor section from nontreated control mouse was packed with viable tumor cells and tumor stroma (boundary outlined by white arrows). (C) Portions of tumor section from M-CPA/PTX-treated mouse showed loose distribution of tumor cells. (D) Representative micrograph of hematoxylin-eosin-stained section of pancreas from a tumor-free mouse treated with M-CPA/PTX showed no residual tumor cells.
Figure 6B:
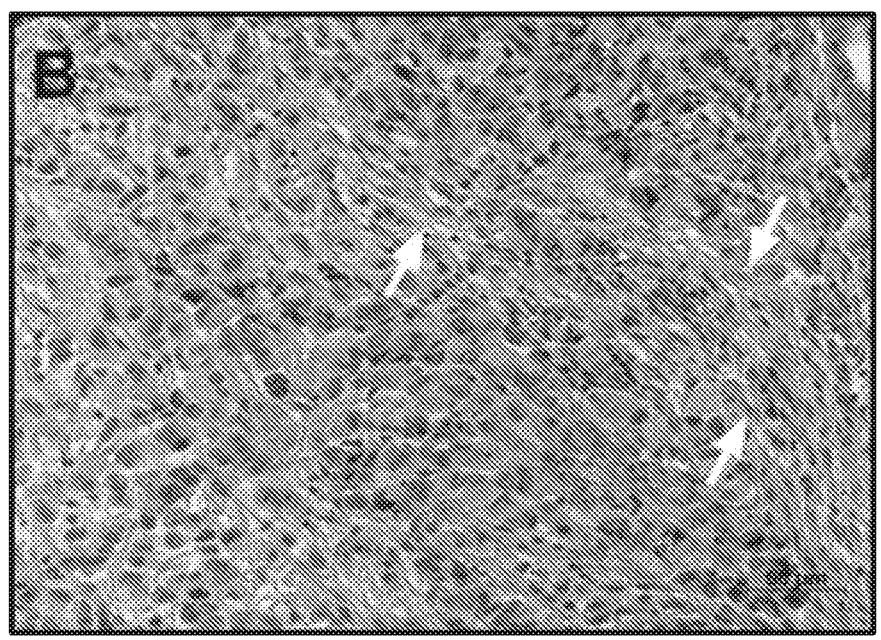
Figure 6C:
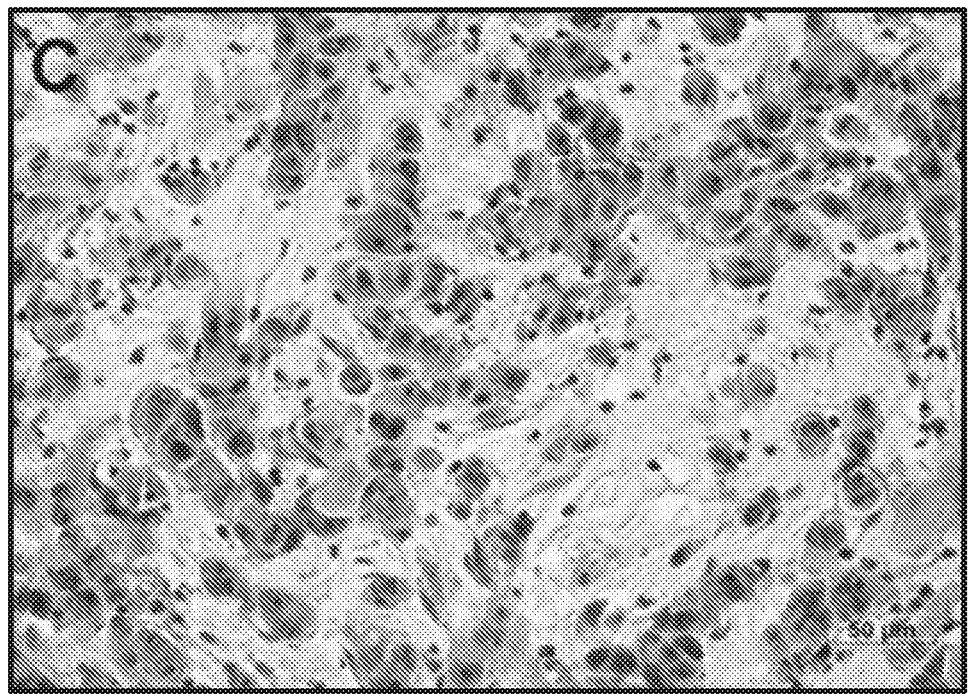

FIG. 6A shows the relative tumor growth curves in the Miapaca-2-luc xenograft model for no treatment (control), M-CPA, M-PTX, and M-CPA/PTX, where the relative tumor growth was defined as the ratio of the bioluminescence flux (photons per second) at each time point to the flux before treatment started. The antitumor efficacy was in the order M-CPA/PTX>M-PTX>M-CPA. At 5 weeks after the initial injection, the relative tumor growth for the control, M-CPA, M-PTX, and M-CPA/PTX regimens was 19.1±2.2, 5.2±2.3, 1.2±0.2, and 0.4±0.1 fold, respectively. The M-CPA/PTX group had slower tumor growth than any other group ($p<0.01$). Mice were euthanized 5 weeks after the initial treatment, and tumors were retrieved for histological analysis. Hematoxylin and eosin-stained sections revealed that tumors in the control mice were packed with viable tumor cells and had a dense stroma compartment (white arrows) (FIG. 6B), whereas tumors in the M-CPA/PTX-treated mice had loosely packed tumor cells (FIG. 6C). Notably, four of the nine mice in the M-CPA/PTX group were tumor free (FIG. 6D), whereas all mice in the other groups had residual tumors.

Immunohistochemical analysis. The tumor sections were stained for expression of Ki67 (proliferation), CD31 (vasculature), and α-SMA (activated cancer-associated fibroblasts). Results are summarized in FIG. 7; the micrographs are representative images from at least 15 randomly selected 20× fields of view. The Ki67 staining results are presented in FIGS. 7A-E. The frequency of $Ki67^+$ nuclei was in the order control>M-CPA>M-PTX>M-CPA/PTX. All three treated groups had fewer $Ki67^+$ nuclei than the control group did ($p<0.001$). Tumors from mice treated with M-CPA/PTX had fewer Ki67+ nuclei than tumors from M-CPA-treated mice did ($p<0.05$). The CD31 staining results are presented in FIGS. 7F-J. Compared to control, treatment with M-CPA/PTX increased the tumor vasculature more than 10-fold ($p<0.001$); treatment with M-CPA increased the tumor vasculature 3.6-fold ($p<0.05$). M-PTX did not induce a significant change in the density of micro-blood vessels ($p>0.05$). The α-SMA staining results are presented in FIGS. 7K-O. M-CPA and M-CPA/PTX significantly reduced the α-SMA+ pixels to 4.8±0.7% and 3.6±0.4% of total pixels, respectively, whereas α-SMA+ pixels were 13.0±1.0% in the control group ($p<0.001$). M-PTX (α-SMA+pixels 10.0±1.0%) did not cause a significant change from the control ($p>0.05$).

The above data supports the idea that M-CPA inhibited the proliferation of pancreatic cancer cells and HPSCs through the SHH signaling pathway. Moreover, the data suggests that M-CPA selectively depleted the population of pancreatic CSCs and inhibited the formation of tumorspheres. The dual-action M-CPA/PTX effectively killed tumor cells and HPSCs and depleted CSCs in vitro. The dual-action M-CPA/PTX increased tumor vasculature density, remodeled tumor stroma, and delayed the growth of orthotopic human pancreatic cancer Miapaca-2 xenograft tumors in vivo.

In the disclosure reported here, a polyion complex micelle system was prepared to encapsulate CPA. The micelles presented in this disclosure may have the following unique properties. First, the major component of the micelles (FIG. 1A) was an anionic polymer that consisted of a brush-like PEG block and a hydrophobic block with pendant oligo(ε-caprolactone) chains. The PEG brush is expected to provide shielding for recognition by the reticuloendothelial system and prolong the blood circulation of the micelles. Second, succinic acid was conjugated at the end of the oligo(ε-caprolactone) side chains, whose carboxylate could interact with CPA through its secondary amine Third, to further increase the colloidal stability of the micelles, a cationic block polymer (FIG. 1C) was added to cross-link the micellar core through electrostatic interaction in addition to hydrophobic interaction. Fourth, it was found that the resultant drug-loaded micelles could be frozen and stored at −80° C. for up to 3 months without significant increase in micelle size or decrease in drug loading (Table 2). The long term stability of these particles is a useful property for translating the micelle into clinical application. When drug-loaded micelles were incubated at 37° C., the release of CPA and PTX was minimal at pH 7.4, which would prevent premature drug release during blood circulation (FIG. 2). The drug release in acidic conditions was studied in pH 5.2 and pH 6.0 buffers. The tumor microenvironment tends to be acidic (~pH 6) (Estrella et al., 2013) due to abnormal metabolism; while the pH values in lysosomes and endosomes ranges from 4.5 to 6.0 (Sorkin and von Zastrow, 2002). At acidic pH, PTX was released slowly while CPA was released much faster, probably because CPA was protonated at low pH and therefore became water soluble at pH 5.2 and pH 6.0.

In these experiments, it was first assessed whether M-CPA retained the functions of CPA against the SHH pathway. SMO expression was observed in all the three pancreatic cancer cell lines as well as HPSC (FIG. 17). It was found that M-CPA could compete with CPA-BODIPY for SMO binding in all three cell lines, indicating that the SMO affinity of encapsulated CPA was preserved. Furthermore, M-CPA treatment successfully downregulated Gli-1 expression in Miapaca-2 and L3.6pl cells, although not in Panc-1 cells, probably because Panc-1 cells have mutations downstream of SMO or another signaling pathway that can activate Gli-1 and thus are resistant to CPA treatment (Steg et al., 2010). Accordingly, M-CPA inhibited the proliferation of Miapaca-2 and L3.6pl cells, but not Panc-1 cells over a 72-h incubation period (Table 3). M-CPA inhibited the formation of Miapaca-2 colonies more efficiently than free CPA did (FIGS. 3G-I). Without wishing to be bound by any theory, it is believed that this increased efficiency may be due to improved solubility of CPA and drug availability.

In contrast to other chemotherapeutics such as gemcitabine, CSCs can be depleted by CPA. The effect of M-CPA and/or M-PTX on the CSC subpopulation of Miapaca-2 cells was assessed using CD133 as a CSC marker. Although M-PTX inhibited the proliferation of Miapaca-2 with high efficiency ($IC_{50}$=1.3±0.1 nM, FIG. 3F), it did not eliminate $CD133^+$ cells; rather, M-PTX enriched the $CD133^+$ population by 59% compared to no treatment (control) (FIG. 4A-E). In contrast, M-CPA depleted the $CD133^+$ population. Treatment with M-CPA alone also reduced the ability of Miapaca-2 cells to form tumorspheres, a measure of the stemness of cancer cells (FIG. 4F-J).

In this disclosure, the data suggests that M-CPA reverted these stimulatory effects of SHH ligands on HPSCs. M-CPA inhibited the proliferation of HPSCs through the SHH signaling pathway (FIGS. 5A and 5B). In addition, M-CPA abolished the stimulating effects of exogenous SHH ligand on cell proliferation and Gli-1 expression (FIGS. 5C-5D). In vivo studies also showed that M-CPA altered the tumor stroma by increasing the intratumoral vasculature and reducing the activated stroma (FIGS. 7F-7O). Because CPA or M-CPA as a single agent is expected to primarily impact the cancer-associated fibroblasts and stroma of pancreatic cancer, without wishing to be bound by any theory, it is believed that by co-encapsulating CPA and PTX in the same polyion micelles, both the tumor cells and stroma-producing cancer-associated fibroblasts could be attacked simultaneously, leading to increased antitumor efficacy. As expected, M-CPA/PTX was cytotoxic to 2 of the 3 pancreatic cancer cell lines and HPSCs that had showed drug-induced Gli1 down-regulation in vitro (FIG. 3 and Table 3). Similar to M-CPA, M-CPA+M-PTX depleted $CD133^+$ Miapaca-2 cells and reduced the formation of tumorspheres (FIG. 4). These data suggest that co-encapsulation of CPA with PTX could abolish the enrichment of $CD133^+$ cells caused by treatment with M-PTX alone.

Figure 6D:
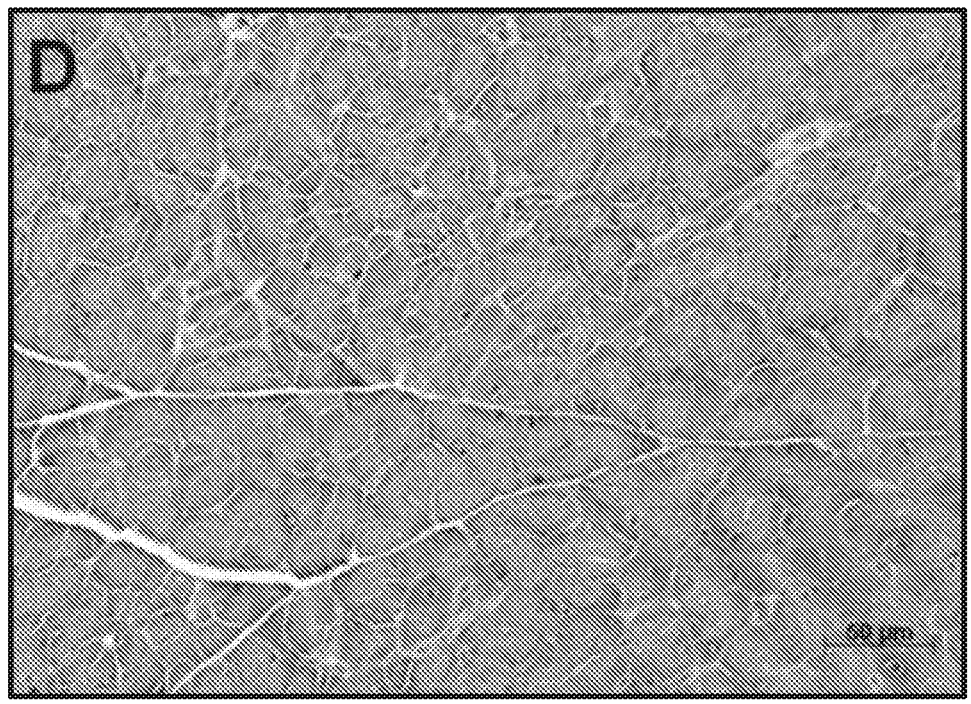
Figure 7A:
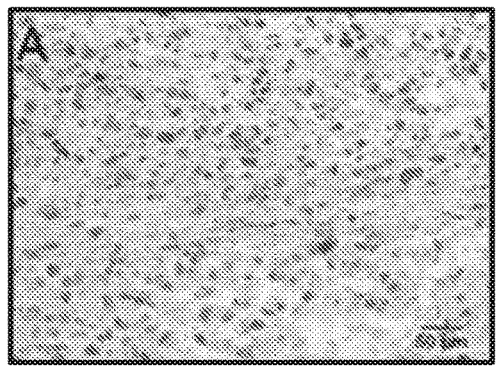
FIGS. 7A-7O: Immunohistochemical staining of MiaPaca tumor sections after various treatments. (A-E) Ki67 staining for proliferating tumor cells in the (A) control, (B) M-CPA, (C) M-PTX, and (D) M-CPA/PTX groups and (E) comparison of the number of Ki67+ nuclei per 20× microscope field among treatment groups. All three treated groups had fewer Ki67+ nuclei than the control group (p<0.001); the M-CPA/PTX group had fewer Ki67+ nuclei than the M-CPA group (p<0.05). (F-J) CD31 staining for tumor vasculature in the (F) control, (G) M-CPA, (H) M-PTX, and (I) M-CPA/PTX groups and (J) comparison of vasculature density among treatment groups. Compared to control, M-CPA/PTX increased the tumor vasculature over 10-fold (p<0.001), whereas M-CPA increased the tumor vasculature 3.6-fold (p<0.05). (K-O) α-SMA staining for activated stroma in the (K) control, (L) M-CPA, (M) M-PTX, and (N) M-CPA/PTX groups and (O) comparison of activated stroma composition among treatment groups. M-CPA and CPA/M-PTX significantly reduced α-SMA staining compared to the control (p<0.001), whereas M-PTX did not cause a significant change compared to the control (p>0.05). At least 15 randomly chosen 20× fields of view were analyzed for each group.
Figure 7B:
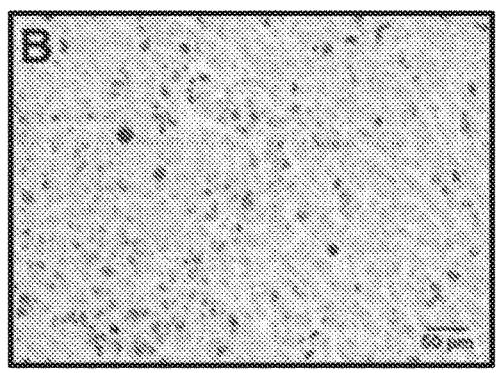
Figure 7C:
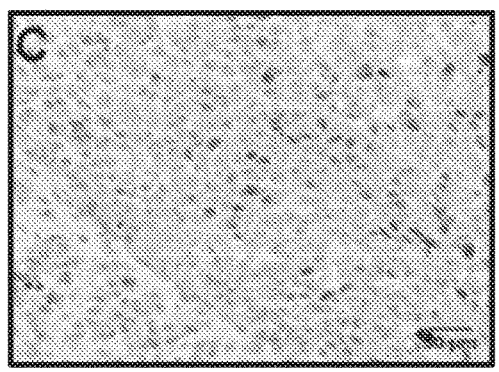
Figure 7D:
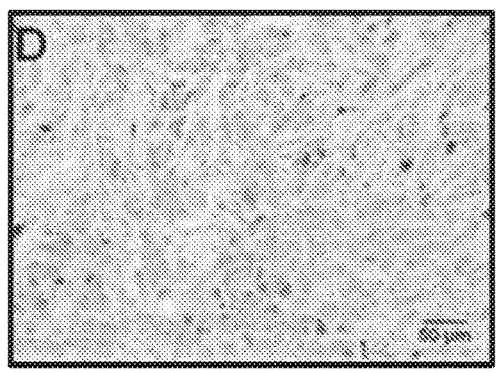
Figure 7E:
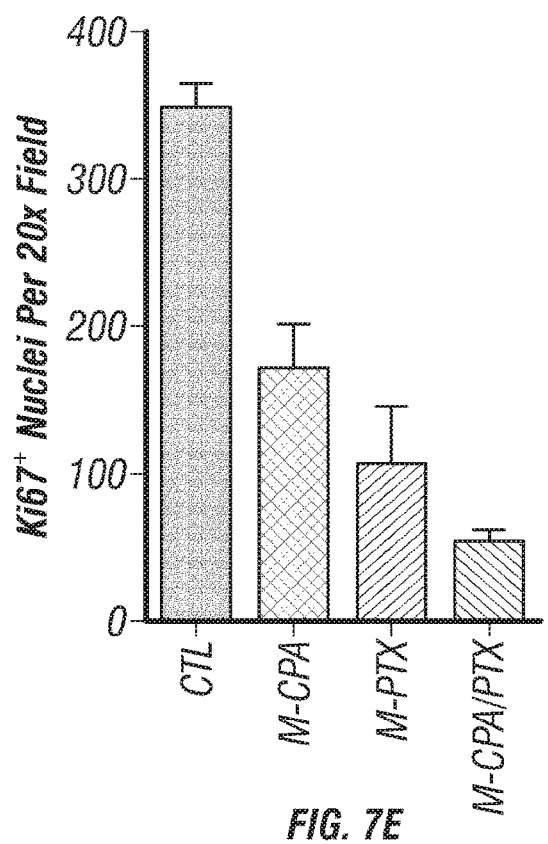
Figure 7F:
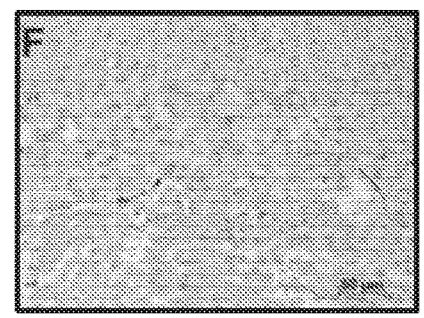
Figure 7G:
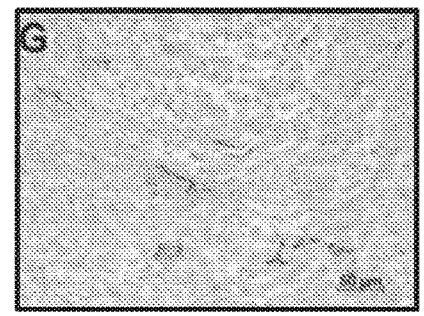
Figure 7H:
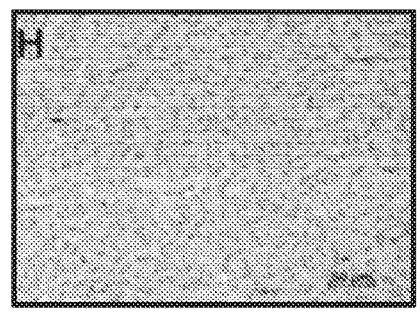
Figure 7I:
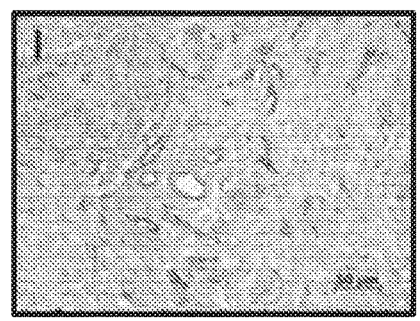
Figure 7J:
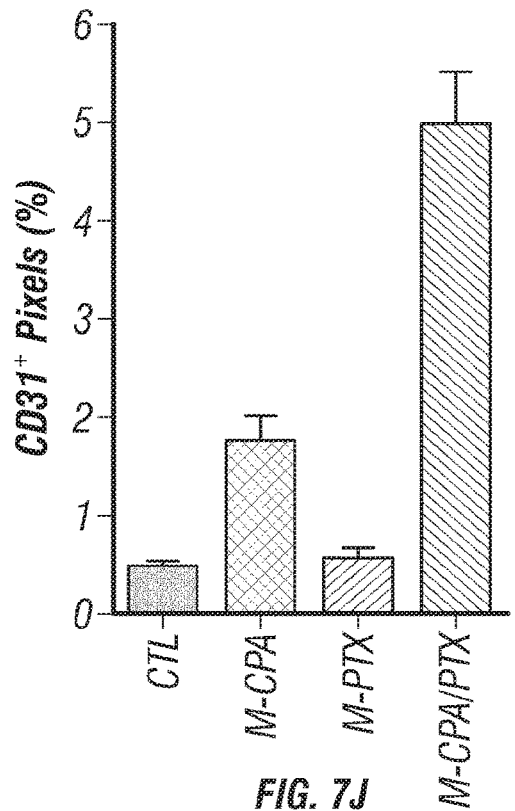
Figure 7K:
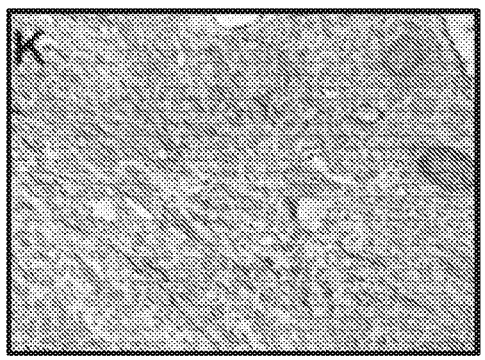
Figure 7L:
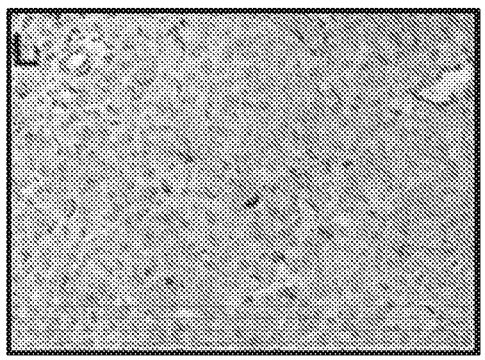
Figure 7M:
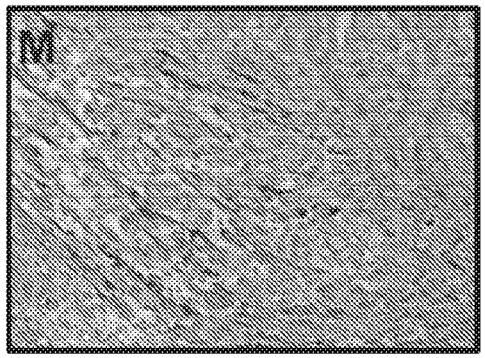
Figure 7N:
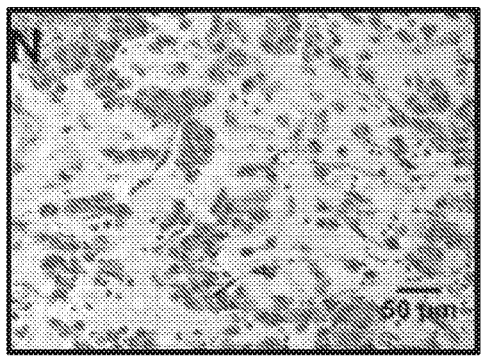
Figure 7O:
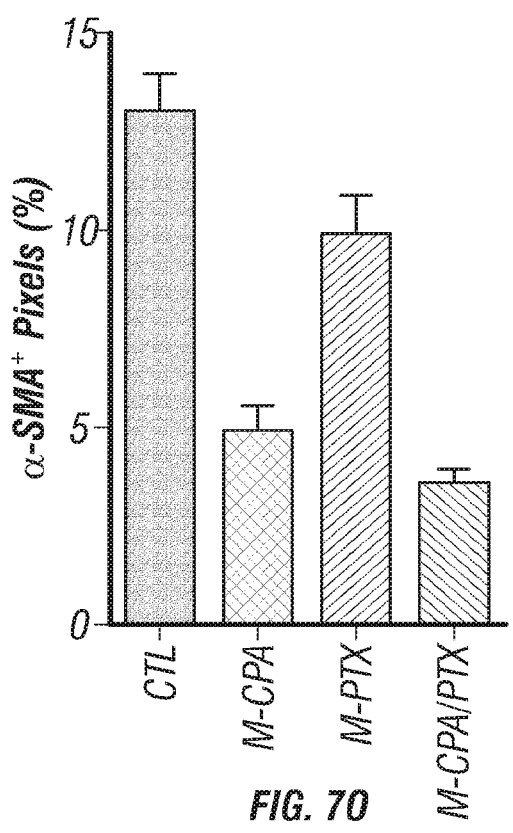
Figure 8:
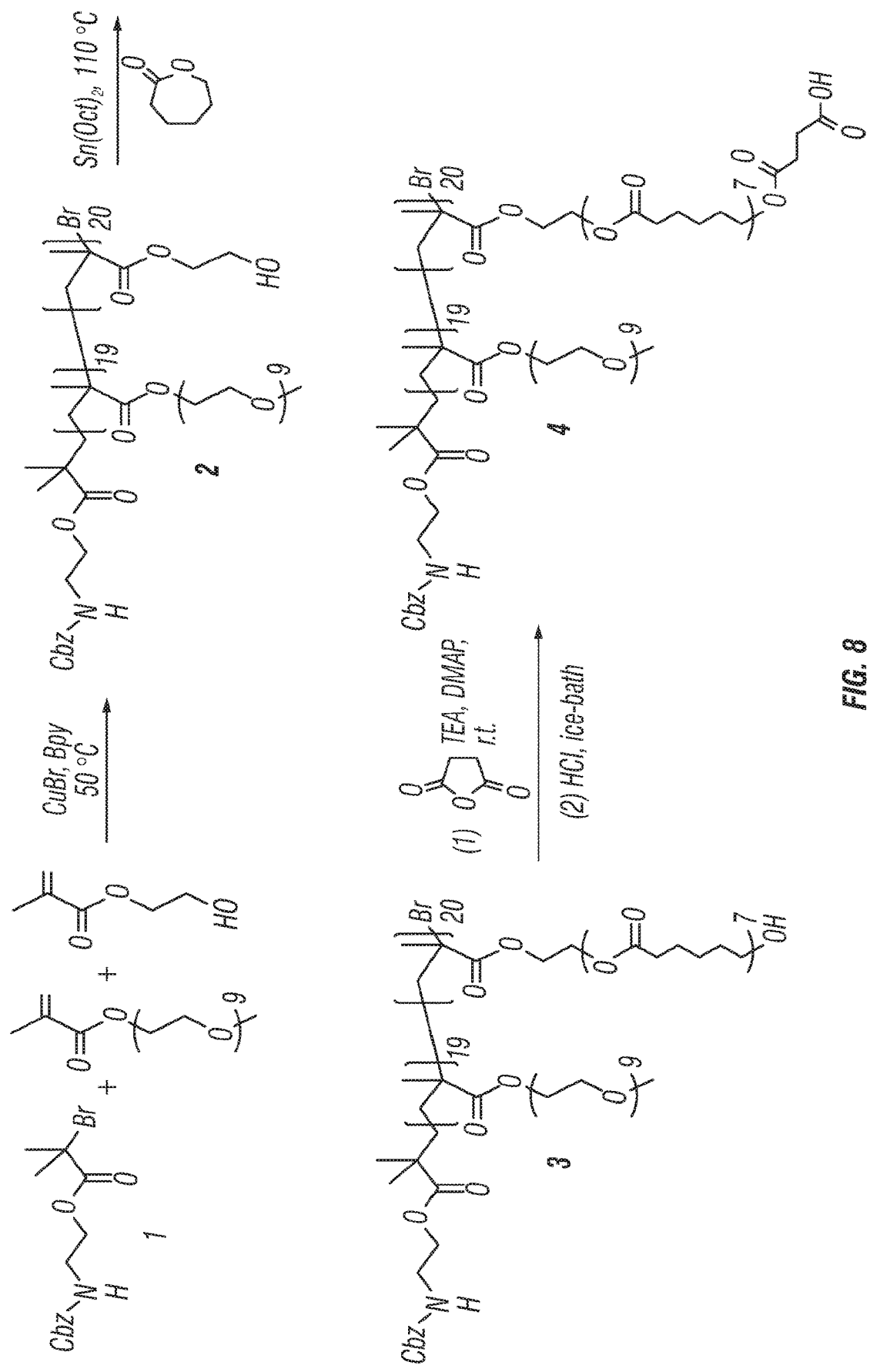
FIG. 8: Schematic illustration for the preparation of anionic polymer poly(PEGMA)$_{19}$-poly[HEMA-g-(CL$_7$)-mono-succinate ester)]$_{20}$

In the disclosure with the orthotopic human pancreatic cancer Miapaca-2 xenograft model, M-CPA/PTX exhibited better antitumor efficacy than control, M-PTX, or M-CPA (FIG. 6A). Furthermore, four of nine mice treated with M-CPA/PTX were rendered histologically tumor free (FIG. 6D). The enhanced antitumor activity observed with M-CPA/PTX was accompanied by an increase in vasculature density, remodeling of tumor stroma, and decrease in proliferation of tumor cells (FIG. 7).

Figure 18:
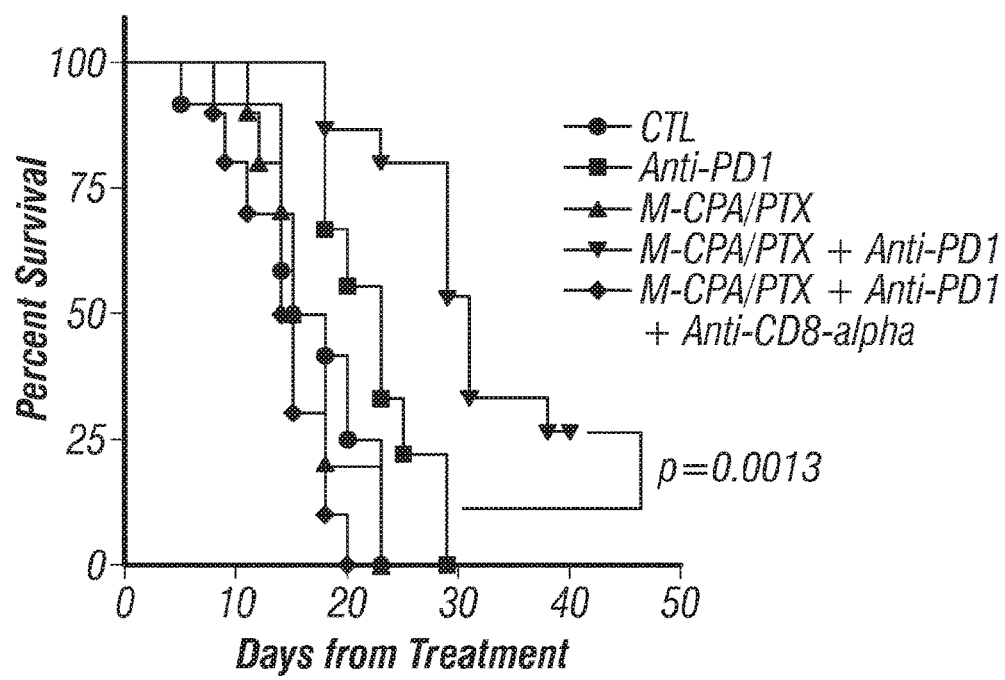
FIG. 18: Survival of orthotopic murine PDAC tumors with Kras mutation (Kras*). The medium survivals were: (1) CTL 16.5 days, (2) M-CPA/PTX 16.5 days, (3) Anti-PD1 23 days, (4) M-CPA/PTX+Anti-PD1 31 days, and (5) M-CPA/PTX+Anti-PD1+Anti-CD8α 14.5 days. The survival of group 4 was significantly longer than group 3 (p=0.0013).

Next, drug-loaded micelles were tested on the orthotopic Kras* (with Kras mutation) syngeneic mouse model of PDAC. Survival of mice with Kras* syngeneic PDAC tumors was tested (FIG. 18). C57BL/6 mice were inoculated with murine Kras* PDAC tumors in the pancreas. The mice then received treatment once the tumor was palpable (~5 mm in diameter). Mice were randomly divided into the following groups: (1) CTL: no treatment. (2) Anti-PD1: intraperitoneal injection at 100 μg every 48 hours, until death. (3) M-CPA/PTX: intravenous injection per day at 5 mg/kg/drug for three consecutive days, then monitored until death. (4) M-CPA/PTX+Anti-PD1: intravenous injection per day at 5 mg/kg/drug for three consecutive days. The mice rested for 1 day, and received anti-PD1 antibody at 100 μg/mouse every 48 hours until death. (5) M-CPA/PTX+ Anti-PD1+Anti-CD8α: Anti-CD8 antibody was injected intraperitoneally at 100 μg/dose along with the anti-PD1 antibody. Other treatments were the same as group (4). Each group had 9 to 10 mice. Mice were monitored daily and sacrificed if moribund or with excessive tumor burden. All mice were sacrificed at the end of the experiments, i.e., 40 days after the start of treatment. Mouse survivals of different groups were fit into Kaplan-Meier curves and compared using log-rank test. A p-value less than 0.05 indicated significant difference. As shown in FIG. 18, The medium survivals were: (1) CTL 16.5 days, (2) M-CPA/PTX 16.5 days, (3) Anti-PD1 23 days, (4) M-CPA/PTX+Anti-PD1 31 days, and (5) M-CPA/PTX+Anti-PD1+Anti-CD8α 14.5 days. The survival of group 4 was significantly longer than group 2 (p=0.0013).

Figure 19:
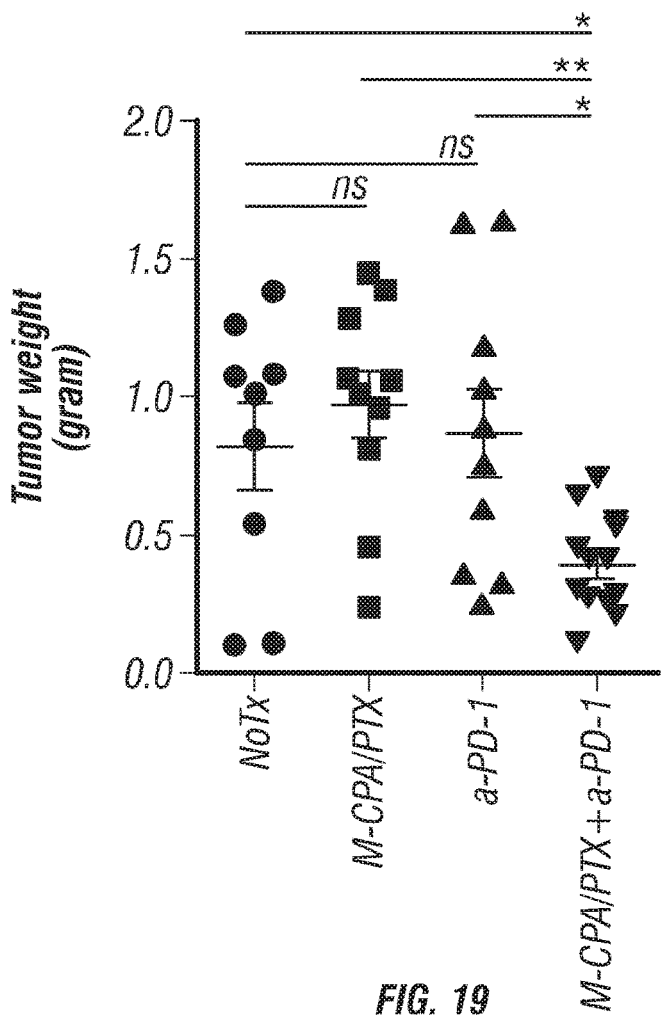
FIG. 19: Tumor weight of Kras* tumors. Differences were noted by * (p<0.05), ** (p<0.01), or ns (not significant). At 10 days after the start of treatment, the tumors treated with M-CPA/PTX+Anti-PD1 were significantly smaller than the other three groups.

The effect of drug-loaded micelles on tumor weight using the Kras* syngeneic model of PDAC was tested. Inoculated mice were randomly divided into 4 groups once the tumors were palpable (~5 mm) (set as day 0), as follows: (1) CTL: no treatment. (2) M-CPA/PTX: mice were intravenously injected with 5 mg/kg/drug once per day on days 0, 1, and 2. (3) Anti-PD1: mice were intraperitoneally injected with 100 μg antibody per day on days 4, 6, 8, and 10. (4) M-CPA/PTX+Anti-PD1: mice were intravenously injected with 5 mg/kg/drug once per day on days 0, 1, and 2; then intraperitoneally injected with 100 μg antibody per day on days 4, 6, 8, and 10. Mice were sacrificed on day 10, 4 hrs after the last injection of antibody. Tumors were collected and weighed immediately. Each group had 10 mice. Data was presented as mean±standard error of mean. Tumor weights were compared using one-way ANOVA with ad-hoc Tukey multiple comparison test. Differences were noted by * (p<0.05), ** (p<0.01), or ns (not significant). Results are shown in FIG. 19. As shown in FIG. 19. At 10 days after the start of treatment, the tumors treated with M-CPA/PTX+ Anti-PD1 were 0.39±0.05 g, significantly smaller than the other three groups: CTL (0.82±0.16 g), M-CPA/PTX (0.97±0.12 g), and Anti-PD1 (0.87±0.16 g). There was no difference among control and monotherapy groups.

Figure 20A:
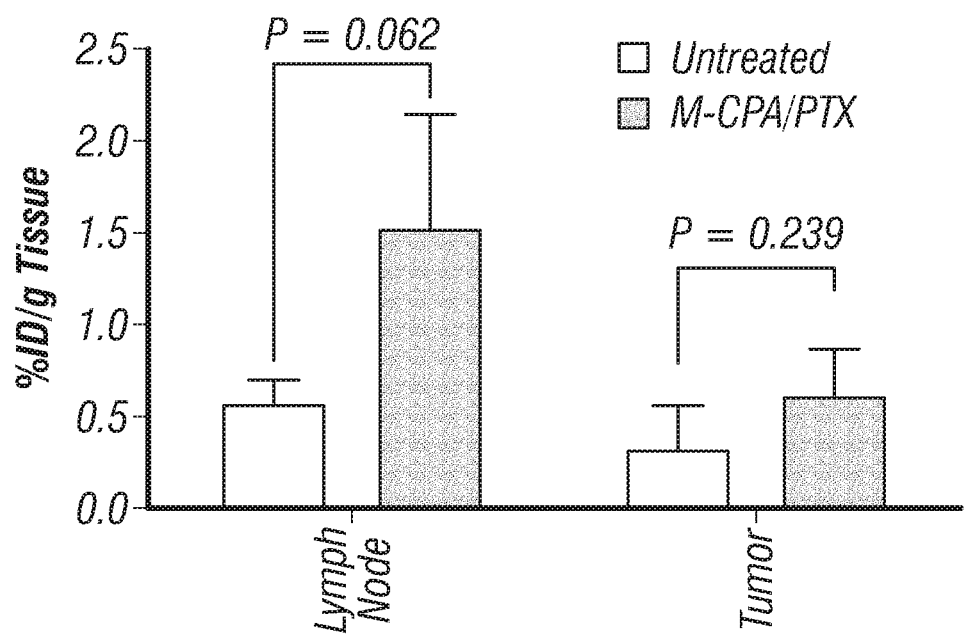
FIGS. 20A-B: $^{64}$Cu-anti-PD1 in tumor-draining lymph nodes and Kras* tumor.
Figure 20B:
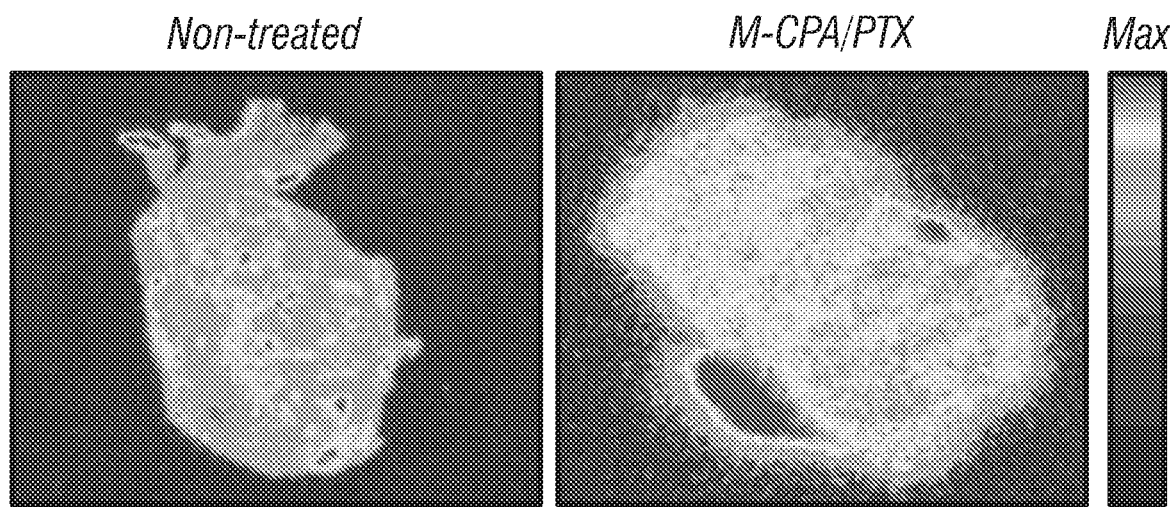

The inoculated Kras* tumor-bearing mice were randomly divided into two groups once the tumors were palpable (~5 mm) (set as day 0), as follows: (1) CTL: no treatment. (2) M-CPA/PTX: mice were intravenously injected with 5 mg/kg/drug once per day on days 0, 1, and 2. Both groups were intravenously injected with $^{64}$Cu-labeled anti-PD1 antibody on day 4. Mice were sacrificed, tumors and lymph nodes were collected at 24 hours after antibody injection. Radioactivity associated with tumors or lymph nodes was measured on a γ-counter. The tumor uptake in each organ was calculated as percent of injected radioactivity per gram of tissue (% ID/g), and presented as (mean±standard deviation). Each group had 4 mice. Frozen sections of tumors were scanned for autoradiographs to show the intratumoral distribution of 64Cu-labeled anti-PD1 antibody. As shown in FIG. 20A, quantification of $^{64}$Cu-anti-PD1 in tumor-draining lymph nodes and Kras* tumor showed a trend of increased distribution of the antibody, which recognizes PD1+ T cells, after M-CPA/PTX treatment. As shown in FIG. 20B, autoradiographs of Kras* tumors obtained at 24 h after intravenous injection of $^{64}$Cu-anti-PD1 were observed to result in a more homogenous distribution of the antibody, which recognizes PD1+ T cells, after M-CPA/PTX treatment.

Figure 21:
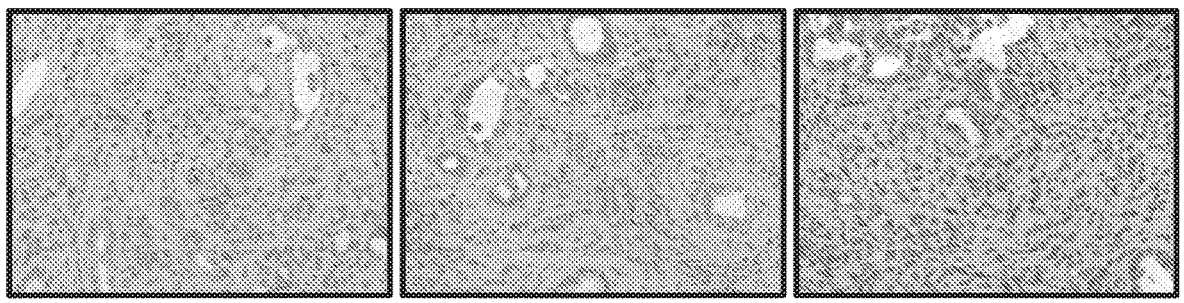
FIG. 21: Effect of M-CPA/PTX on T cells infiltration of tumors in vivo. The treated tumors had significantly more T cells infiltration than untreated CTL tumors. Data was presented as mean±standard error of mean. Differences between the two groups were compared using unpaired t-test. ** indicates a p-value<0.01.
Figure 21:
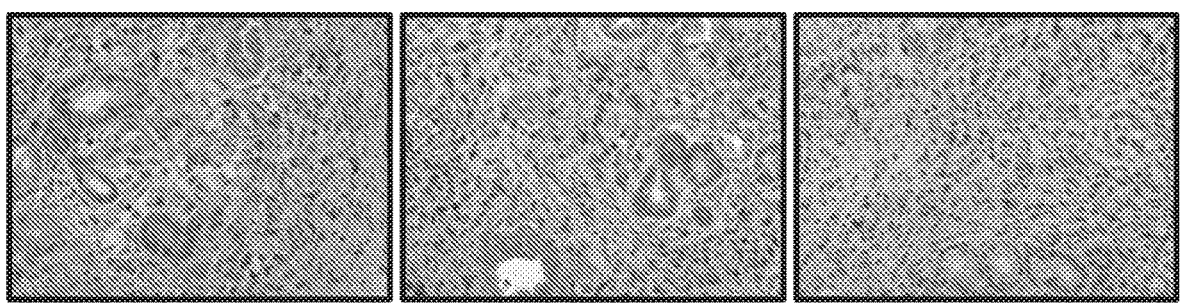
Figure 21:
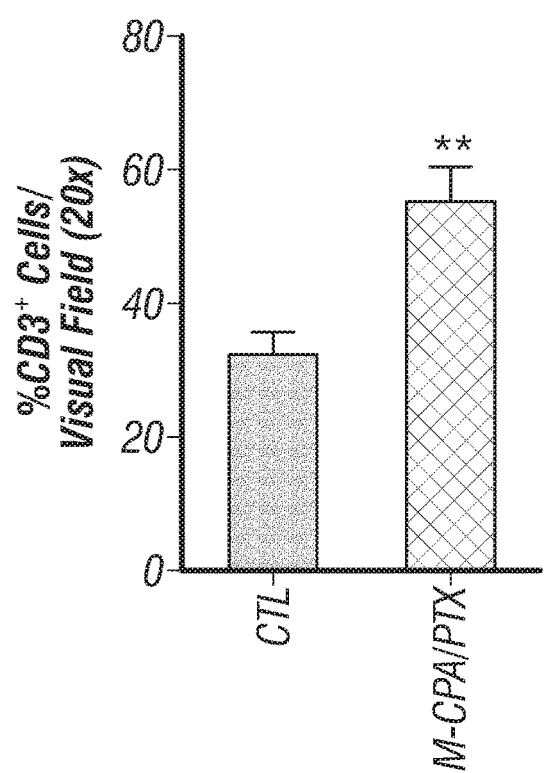

A genetically engineered mouse model of PDAC (the KPC-luc mouse model) was also used to test for the effects of drug-loaded micelles on tumors. KPC-luc mice at ages of 125 to 130 days were used for the studies. The mice were assigned into two different groups: (1) untreated control mice (CTL), or (2) mice intravenously injected with M-CPA/PTX at 5 mg/kg/drug/dose for 6 doses over two weeks. Mice were then sacrificed at 24 hrs after the last dose. Tumors were collected, sectioned, and stained for CD3$^+$ T cells. Twenty random visual fields at 200× magnification were photographed, and the number of CD3$^+$ cells were counted. Results are shown in FIG. 21. As shown in FIG. 21, the treated tumors had significantly more T cells infiltration than untreated CTL tumors. The treated tumor had 55±5 CD3$^+$ cells per 200× visual field, as compared to the CTL tumor with 32±3 CD3$^+$ cells per 200× visual field (p<0.01).

Figure 22:
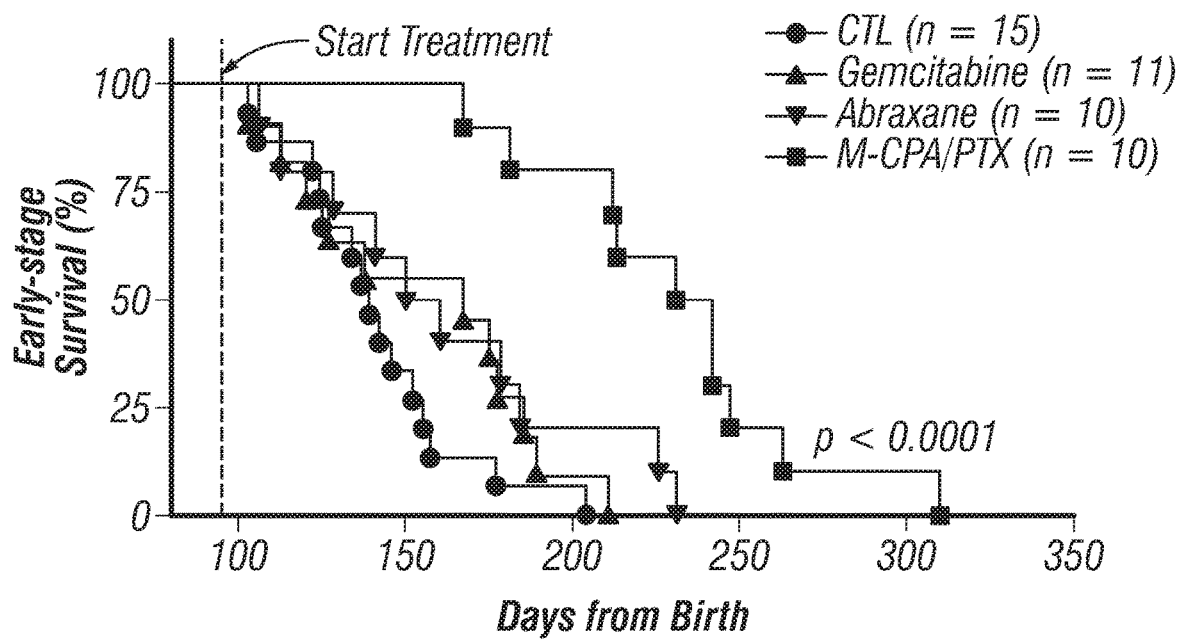
FIG. 22: Antitumor efficacy of M-CPA/PTX in a transgenic mice model with spontaneous PDAC in the pancreas of KPC-Luc mice. Mice with positive bioluminescence signals were enrolled at 95 to 100 days of age. M-CPA/PTX was given at 5 mg/kg/drug per injection. The treatment schedule was: 3 intravenous injections per week for the first 2 weeks, followed by 2 intraperitoneal injections per week until death or 90 days from the initiation of treatment. Untreated mice were kept as control (CTL). Gemcitabine and abraxane were used as the standard therapies. Gemcitabine was intraperitoneally injected at 100 mg/kg every other day until death. Abraxane was given at 5 mg/kg/injection following the same schedule as M-CPA/PTX.

The genetically engineered mouse model of PDAC (the KPC-luc mouse model) was also used to test for the anti-tumor efficacy of drug-loaded micelles on tumors in a survival study. KPC-luc mice that showed positive luminescence (>1×10$^9$ photons/second) at ages of 95 to 100 days were used for the studies. The mice were assigned into four different groups: (1) mice with untreated cytotoxic T lymphocytes (CTL) (control group), (2) mice intravenously injected gemcitabine at 100 mg/kg every other day until death, (3) mice given Abraxane at 5 mg/kg/injection, and (4) M-CPA/PTX given at 5 mg/kg/drug per injection. The treatment schedule for Abraxane and M-CPA/PTX was: 3 intravenous injections per week for the first 2 weeks, followed by 2 intraperitoneal injections per week until death or 90 days from the initiation of treatment. As shown in FIG. 22, The median survivals of CTL, gemcitabine, and abraxane groups were 139, 167, and 155 days, respectively. The M-CPA/PTX group had its first mortality at 167 days of age. Its median survival was 236.5 days, significantly longer than the other groups (p<0.0001, log-rank test).

Figure 23:
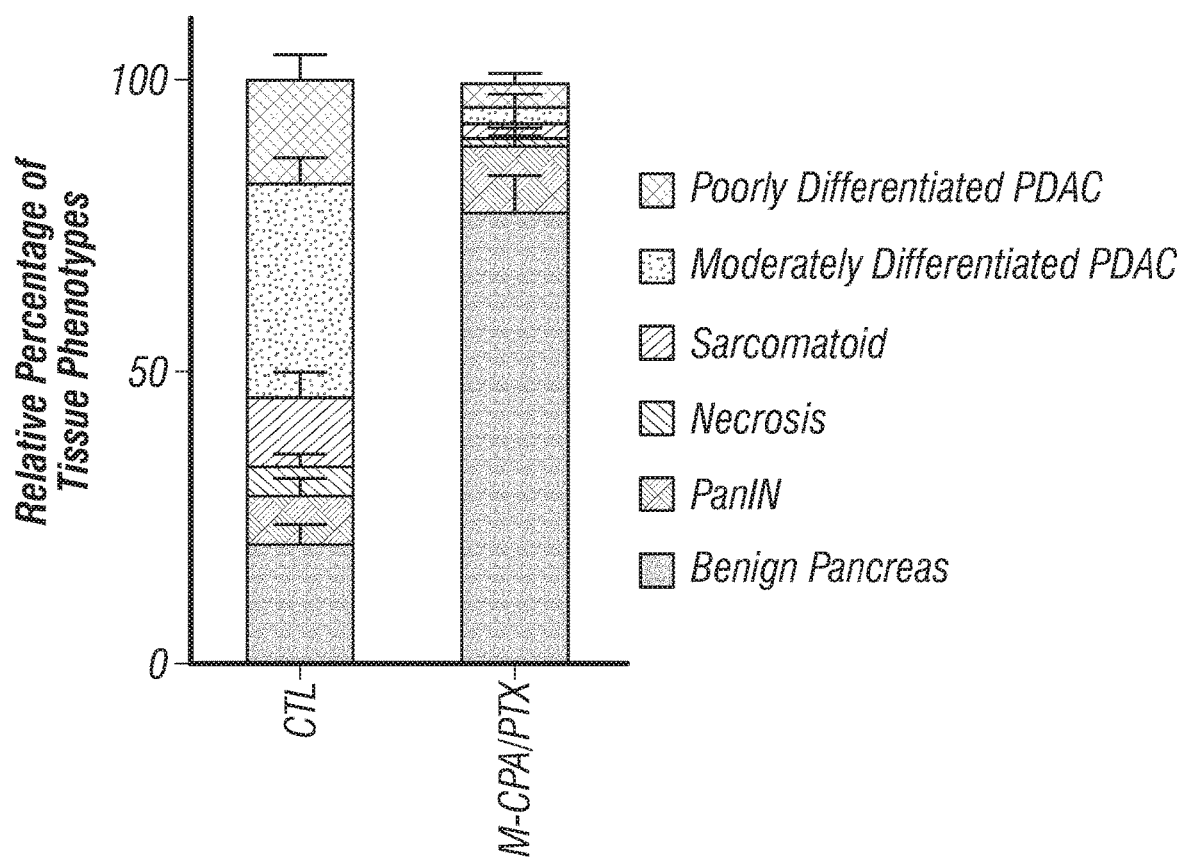
FIG. 23: Histological analysis of tumors removed from untreated control mice and KPC-Luc mice treated with M-CPA/PTX. Mice of about 125 days old when tumors became palpable were enrolled into the study. Each mouse in the M-CPA/PTX treatment group was given six intravenous injections of M-CPA/PTX (5 mg/kg/drug/injection) over 2 weeks. At 24 hours after the last injection, mice were sacrificed to collect tumors and processed for histological evaluation.

FIG. 23 shows histological analysis of tumors removed from untreated control mice and KPC-Luc mice treated with M-CPA/PTX. In this study, mice with palpable tumors (about 125 days old) either not treated (control group, CTL) or treated with M-CPA/PTX (six intravenous injections at 5 mg/kg/drug/injection over 2 weeks). At 24 hours after the last injection, mice were sacrificed to collect tumors. Analyses of tumor histopathology features showed that, compared to CTL, M-CPA/PTX reduced the poorly differentiated PDAC by 82% (p=0.037) and the moderately differentiated PDAC by 92% (p<0.0001). It increased the benign pancreas by 3.7 folds (p<0.0001).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bailey et al., Sonic Hedgehog Promotes Desmoplasia in Pancreatic Cancer. Clinical Cancer Research, 14 (19), 5995-6004, 2008.

Bee et al., The development of a high-content screening binding assay for the smoothened receptor. J Biomol Screen, 17 (7), 900-11, 2012.

Bronich et al., Polymer micelle with cross-linked ionic core. Journal of the American Chemical Society, 127 (23), 8236-7, 2005.

Chen et al., Small molecule modulation of Smoothened activity. Proceedings of the National Academy of Sciences of the United States of America, 99 (22), 14071-6, 2002.

Chitkara et al., Micellar Delivery of Cyclopamine and Gefitinib for Treating Pancreatic Cancer. Molecular Pharmaceutics, 9 (8), 2350-2357, 2012.

Cho et al., Poly(ethylene glycol)-block-poly(epsilon-caprolactone) micelles for combination drug delivery: evaluation of paclitaxel, cyclopamine and gossypol in intraperitoneal xenograft models of ovarian cancer. J Control Release, 166 (1), 1-9, 2013.

Dean et al., Tumour stem cells and drug resistance. Nat Rev Cancer, 5 (4), 275-284, 2005.

Estrella et al., Acidity generated by the tumor microenvironment drives local invasion. Cancer Res, 73 (5), 1524-35, 2013.

Feig et al., The pancreas cancer microenvironment. Clin Cancer Res, 18 (16), 4266-76, 2012.

Feldmann et al., Blockade of hedgehog signaling inhibits pancreatic cancer invasion and metastases: a new paradigm for combination therapy in solid cancers. Cancer Res, 67 (5), 2187-96, 2007.

Geng et al., Hedgehog signaling in the murine melanoma microenvironment. Angiogenesis 2007, 10 (4), 259-67, 2007.

Hermann et al., Distinct Populations of Cancer Stem Cells Determine Tumor Growth and Metastatic Activity in Human Pancreatic Cancer. Cell Stem Cell 2007, 1 (3), 313-323, 2007.

Hwang et al., Inhibition of the Hedgehog Pathway Targets the Tumor-Associated Stroma in Pancreatic Cancer. Molecular Cancer Research, 10 (9), 1147-1157, 2012.

Kelleher, Hedgehog signaling and therapeutics in pancreatic cancer. Carcinogenesis 32 (4), 445-51, 2011.

Kim et al., Pilot clinical trial of hedgehog pathway inhibitor GDC-0449 (vismodegib) in combination with gemcitabine in patients with metastatic pancreatic adenocarcinoma. Clinical Cancer Research, 20 (23), 5937-45, 2014.

Lauth et al., Inhibition of GLI-mediated transcription and tumor cell growth by small-molecule antagonists. Proc Natl Acad Sci USA, 104 (20), 8455-60, 2007.

Lee et al., D. M., Pancreatic Cancer Stem Cells. Journal of Clinical Oncology, 26 (17), 2806-2812, 2008.

Lee et al., Stromal response to Hedgehog signaling restrains pancreatic cancer progression. Proc Natl Acad Sci USA, 111 (30), E3091-100, 2014.

Li et al., Chaotropic-anion-induced supramolecular self-assembly of ionic polymeric micelles. Angewandte Chemie. International Ed. In English, 53 (31), 8074-8, 2014.

Mahadevan and Von Hoff, Tumor-stroma interactions in pancreatic ductal adenocarcinoma. Mol Cancer Ther, 6 (4), 1186-97, 2007.

Mantoni et al., Pancreatic stellate cells radioprotect pancreatic cancer cells through beta1-integrin signaling. Cancer Res, 71 (10), 3453-8, 2011.

Mikhail and Zeidan, Stem cells in gastrointestinal cancers: The road less travelled. World journal of stem cells, 6 (5), 606-13, 2014.

Morris et al., Hedgehog, Wnt and the twisted developmental biology of pancreatic ductal adenocarcinoma. Nat Rev Cancer, 10 (10), 683-95, 2010.

Mueller et al., Combined Targeted Treatment to Eliminate Tumorigenic Cancer Stem Cells in Human Pancreatic Cancer. Gastroenterology, 137 (3), 1102-1113, 2009.

Nishiyama and Kataoka, K., Current state, achievements, and future prospects of polymeric micelles as nanocarriers for drug and gene delivery. Pharmacology and Therapeutics, 112 (3), 630-48, 2006.

Olive et al., Inhibition of Hedgehog signaling enhances delivery of chemotherapy in a mouse model of pancreatic cancer. Science, 324 (5933), 1457-61, 2009.

Onishi and Katano, Hedgehog signaling pathway as a new therapeutic target in pancreatic cancer. World J Gastroenterol, 20 (9), 2335-42, 2014.

Rhim et al., Stromal Elements Act to Restrain, Rather Than Support, Pancreatic Ductal Adenocarcinoma. Cancer Cell, 25 (6), 735-747, 2014.

Rucki and Zheng, Pancreatic cancer stroma: understanding biology leads to new therapeutic strategies. World J Gastroenterol, 20 (9), 2237-46, 2014.

Shafaee et al., Cyclopamine increases the cytotoxic effects of paclitaxel and radiation but not cisplatin and gemcitabine in Hedgehog expressing pancreatic cancer cells. Cancer Chemotherapy and Pharmacology, 58 (6), 765-770, 2006.

Shoemaker et al., Application of a Human Tumor Colony-forming Assay to New Drug Screening. Cancer Research, 45 (5), 2145-2153, 1985.

Simeone, Pancreatic Cancer Stem Cells: Implications for the Treatment of Pancreatic Cancer. Clinical Cancer Research, 14 (18), 5646-5648, 2008.

Sorkin and von Zastrow, Signal transduction and endocytosis: close encounters of many kinds. Nat Rev Mol Cell Biol, 3 (8), 600-614, 2002.

Steg et al., Gli3 mediates cell survival and sensitivity to cyclopamine in pancreatic cancer. Cancer Biol Ther, 10 (9), 893-902, 2010.

Tempero et al., Pancreatic cancer treatment and research: an international expert panel discussion. Ann Oncol, 22 (7), 1500-6, 2011.

Thayer et al., Hedgehog is an early and late mediator of pancreatic cancer tumorigenesis. Nature, 425 (6960), 851-856, 2003.

Waghray et al., Deciphering the role of stroma in pancreatic cancer. Curr Opin Gastroenterol, 29 (5), 537-43, 2013.

Walter et al., Overexpression of Smoothened Activates the Sonic Hedgehog Signaling Pathway in Pancreatic Cancer-Associated Fibroblasts. Clinical Cancer Research, 16 (6), 1781-1789, 2010.

Watkins and Peacock, Hedgehog signaling in foregut malignancy. Biochem Pharmacol, 68 (6), 1055-60, 2004.

You et al., Chemoradiation therapy using cyclopamine-loaded liquid-lipid nanoparticles and lutetium-177-labeled core-crosslinked polymeric micelles. J Control Release, 202, 40-8, 2015.

Zhou et al., Selective inhibitory effect of HPMA copolymer-cyclopamine conjugate on prostate cancer stem cells. Biomaterials, 33 (6), 1863-72, 2012.

What is claimed is:

1. A polymer, wherein the polymer is a block copolymer comprising a polyacrylic acid backbone with a first plurality of PEG sidechains and a second plurality of ε-caprolactone sidechains, and wherein the ε-caprolactone sidechains terminates with carboxy, phosphonate, or hydroxysulfonyl.

2. The polymer of claim 1, wherein the PEG sidechain component comprises from 5 ethylene glycol monomers to 50 ethylene glycol monomers.

3. The polymer of claim 1, wherein the PEG sidechain is capped with a methyl group.

4. The polymer of claim 1, wherein the ε-caprolactone sidechain comprises from 2 ε-caprolactone repeating units to 20 ε-caprolactone repeating units.

5. The polymer of claim 1, wherein the ε-caprolactone sidechain is esterified with a succinate group.

6. The polymer of claim 1, wherein the ε-caprolactone sidechain is linked to the polyacrylic acid backbone by an ethylene glycol linker.

7. The polymer of claim 1, wherein the polyacrylic acid backbone is capped with an benzyl N-(2-hydroxylethyl) carbamate or ethanolamine group.

8. The polymer of claim 1, wherein the polyacrylic acid backbone is terminated with a halogen group.

9. The polymer of claim 1, wherein the polymer is further defined by the formula:

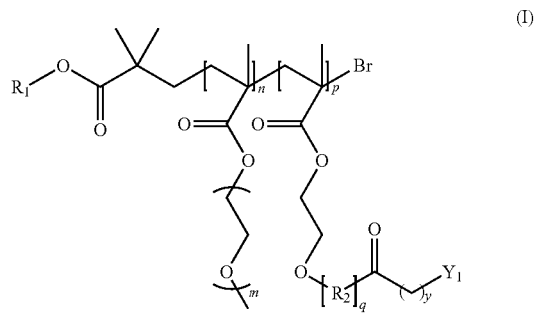

(I)

wherein:

$R_1$ is alkyl$_{(C1-18)}$, cycloalkyl$_{(C1-18)}$, aryl$_{(C1-18)}$, or a substituted version of any of these groups; or an alkyl$_{(C1-18)}$ substituted with a protected amine group;

$R_2$ is a group of the formula:

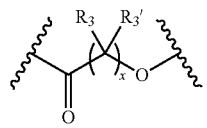

wherein:

$R_3$ and $R_3'$ are each independently hydrogen, alkyl$_{(C1-6)}$, or substituted alkyl$_{(C1-6)}$; and x is 1-10;
m is 5-40;
n is 10-40;
p is 5-40;
q is 1-20;
y is 1-10; and
$Y_1$ is carboxy, phosphonate, or hydroxysulfonyl;

or a pharmaceutically acceptable salt thereof.

10. The polymer of claim 9, wherein m is 5-25.

11. The polymer of claim 1Z wherein p is 5-25.

12. The polymer according to claim 9, wherein $R_3$ and $R_3'$ are hydrogen.

13. The polymer of claim 1, wherein the polymer has the structure:

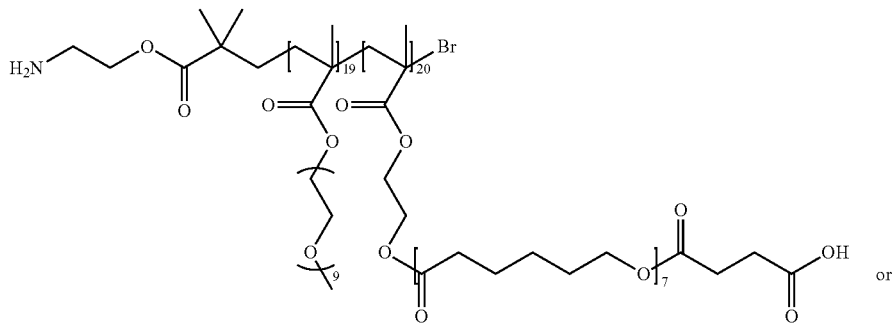

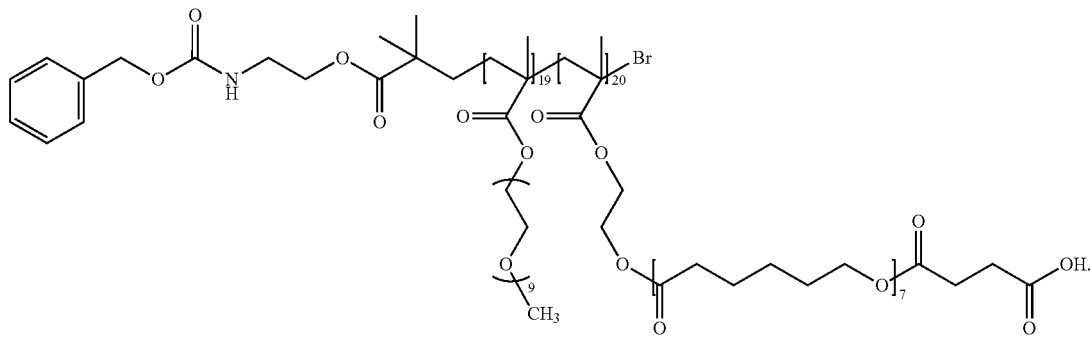

14. A composition comprising the polymer of claim 1, wherein the composition further comprises a second polymer of the formula:

(II)

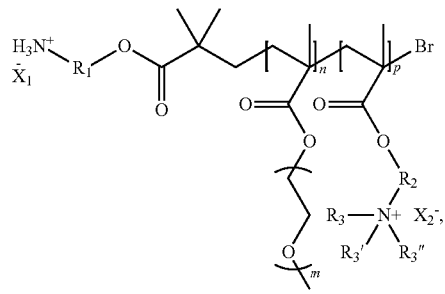

(III)

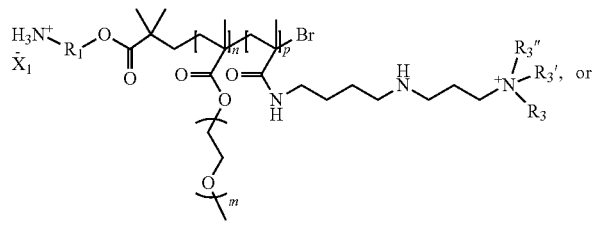

-continued

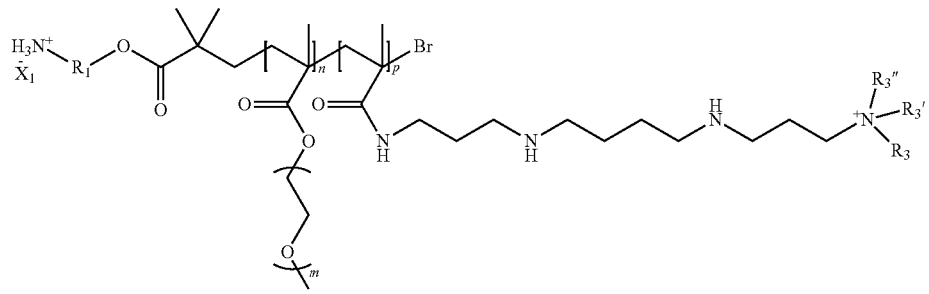

(IV)

wherein:

m is 5-40;

n is 10-40;

p is 5-30;

$R_1$ and $R_2$ are each independently alkanediyl$_{(C1-8)}$, arenediyl$_{(6-12)}$, or a substituted version of either of these groups;

$R_3$, $R_3'$, and, $R_3''$ are each independently alkyl$_{(C1-8)}$, aryl$_{(C3-12)}$, or a substituted version of any of these groups; and $X_1$ and $X_2$ are each independently a monovalent anion; or a pharmaceutically salt thereof.

15. The composition of claim 14, wherein $R_1$ or $R_2$ is ethylene.

16. The composition of claim 14, wherein $R_3$, $R_3'$, and $R_3''$ are each methyl.

17. The composition of claim 14, wherein $X_1$ or $X_2$ is a halide.

18. The composition of claim 14, wherein the second polymer has the structure:

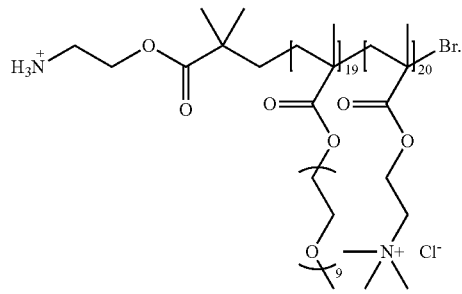

19. A pharmaceutical composition comprising:
(a) a micelle, liposome, or nanoparticle; and
(b) a therapeutic agent;
wherein the micelle, liposome, or nanoparticle comprises a first polymer of claim 1, and the micelle, liposome, or nanoparticle encapsulates the therapeutic agent.

20. The pharmaceutical composition of claim 19, wherein the therapeutic agent is paclitaxel or cyclopamine.

21. The pharmaceutical composition of claim 20, wherein the pharmaceutical composition comprises paclitaxel and cyclopamine.

22. A method of treating a disease in a mammalian subject comprising administering a therapeutically effective amount of a pharmaceutical composition of claim 19 to the subject.

* * * * *

UNITED STATES PATENT AND TRADEMARK OFFICE
CERTIFICATE OF CORRECTION

PATENT NO. : 11,026,889 B2  Page 1 of 1
APPLICATION NO. : 15/780799
DATED : June 8, 2021
INVENTOR(S) : Chun Li et al.

It is certified that error appears in the above-identified patent and that said Letters Patent is hereby corrected as shown below:

In the Claims

In Claim 11, Column 48, Line 12, delete "1Z" and insert --9,-- therefor.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*